United States Patent
Kwiecien et al.

(10) Patent No.: US 10,153,146 B2
(45) Date of Patent: Dec. 11, 2018

(54) HIGH MASS ACCURACY FILTERING FOR IMPROVED SPECTRAL MATCHING OF HIGH-RESOLUTION GAS CHROMATOGRAPHY-MASS SPECTROMETRY DATA AGAINST UNIT-RESOLUTION REFERENCE DATABASES

(71) Applicant: Wisconsin Alumni Research Foundation, Madison, WI (US)

(72) Inventors: Nicholas W. Kwiecien, Madison, WI (US); Derek J. Bailey, Madison, WI (US); Michael S. Westphall, Fitchburg, WI (US); Joshua J. Coon, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 270 days.

(21) Appl. No.: 14/671,199

(22) Filed: Mar. 27, 2015

(65) Prior Publication Data
US 2015/0340216 A1 Nov. 26, 2015

Related U.S. Application Data

(60) Provisional application No. 61/972,073, filed on Mar. 28, 2014.

(51) Int. Cl.
*H01J 49/00* (2006.01)
*G06K 9/00* (2006.01)
*G01N 30/72* (2006.01)

(52) U.S. Cl.
CPC ...... *H01J 49/0036* (2013.01); *G06K 9/00543* (2013.01); *G01N 30/72* (2013.01)

(58) Field of Classification Search
CPC .............. H01J 49/0036; H01J 49/0045; G06F 19/703; G06F 19/707; G06F 19/705; G06K 9/00543
(Continued)

(56) References Cited

U.S. PATENT DOCUMENTS 6,745,134 B2 * 6/2004 Kobayashi .............. G06F 19/16
250/292
6,917,037 B2 * 7/2005 Ootake ............... H01J 49/0036
250/281

(Continued)

FOREIGN PATENT DOCUMENTS

| EP | 2741224 | 6/2014 |
|---|---|---|
| WO | WO2000022649 | 4/2000 |
| WO | WO2012161696 | 11/2012 |

OTHER PUBLICATIONS

Allen et al. (2003) "High-throughput classification of yeast mutants for functional genomics using metabolic footprinting," Nat. Biotechnol. 21:692-6.

(Continued)

*Primary Examiner* — Brooke Purinton
(74) *Attorney, Agent, or Firm* — Leydig, Voit & Mayer, Ltd.

(57) ABSTRACT

The invention provides methods, systems and algorithms for identifying high-resolution mass spectra. In some embodiments, an analyte is ionized and analyzed using high-resolution mass spectrometry (MS) at high mass accuracy (such as ≤75 ppm or ≤30 ppm) and the obtained mass spectra are matched with one or more prospective candidate molecules or chemical formulas. The invention provide, for example, methods and systems wherein the possible fragments that can be generated from the candidate molecules or chemical formulas are determined as well as the masses of each of these fragments. The invention provide, for example, (Continued)

methods and systems wherein the high-resolution mass spectra are then compared with the calculated fragment masses for each of the candidate molecules or chemical formula, and the portion of the high-resolution mass spectra that corresponds or can be explained by the calculated fragment masses is determined.

30 Claims, 43 Drawing Sheets

(58) Field of Classification Search
USPC .............................................. 702/23, 24, 26
See application file for complete search history.

(56) References Cited

U.S. PATENT DOCUMENTS

| | | | | |
|---|---|---|---|---|
| 7,279,679 | B2 | 10/2007 | Old et al. | |
| 7,485,852 | B2* | 2/2009 | Yamashita | G01N 33/6848 250/281 |
| 7,595,484 | B2* | 9/2009 | Yokosuka | H01J 49/004 250/281 |
| 7,684,934 | B2* | 3/2010 | Shvartsburg | H01J 49/04 702/27 |
| 8,026,476 | B2* | 9/2011 | Yamaguchi | G01N 27/62 250/282 |
| 8,168,943 | B2* | 5/2012 | Schwartz | H01J 49/0031 250/281 |
| 8,180,576 | B2* | 5/2012 | Yamaguchi | G01N 27/62 250/281 |
| 8,884,218 | B2* | 11/2014 | Yamaguchi | H01J 49/004 702/22 |
| 9,230,785 | B2* | 1/2016 | Murase | H01J 49/004 |
| 2001/0007349 | A1* | 7/2001 | Nagai | H01J 49/0027 250/281 |
| 2002/0182649 | A1 | 12/2002 | Weinberger et al. | |
| 2004/0111228 | A1* | 6/2004 | Kobayashi | H01J 49/0036 702/81 |
| 2004/0181347 | A1* | 9/2004 | Yoshinari | H01J 49/0036 702/27 |
| 2005/0092910 | A1 | 5/2005 | Geromanos et al. | |
| 2008/0067344 | A1* | 3/2008 | Yamaguchi | H01J 49/0036 250/282 |
| 2008/0121793 | A1* | 5/2008 | Yamaguchi | H01J 49/0081 250/282 |
| 2010/0057372 | A1 | 3/2010 | Fagerquist et al. | |
| 2011/0244445 | A1* | 10/2011 | Moritz | G01N 33/6848 435/5 |
| 2012/0100623 | A1* | 4/2012 | Timar | C12Q 1/6872 436/94 |
| 2012/0191370 | A1* | 7/2012 | Roder | G06F 19/24 702/23 |
| 2012/0294885 | A1* | 11/2012 | David | C07D 471/04 424/184.1 |
| 2013/0282304 | A1* | 10/2013 | Kozawa | H01J 49/0036 702/27 |
| 2014/0142865 | A1* | 5/2014 | Wright | G06F 19/703 702/23 |
| 2014/0183353 | A1* | 7/2014 | Shimada | H01J 49/0036 250/282 |

OTHER PUBLICATIONS

Fiehn (2008) Extending the breadth of metabolite profiling by gas chromatography coupled to mass spectrometry. Trends Analyt. Chem. 27:261-269.

Fiehn et al. (2000) "Identification of Uncommon Plant Metabolites Based on Calculation of Elemental Compositions Using Gas Chromatography and Quadrupole Mass Spectrometry," Anal. Chem. 72:3573-3580.

Fiehn et al. (2000) "Metabolite profiling for plant functional genomics," Nat. Biotechnol. 1157-116.

Goodacre et al. (2004) "Metabolomics by numbers: acquiring and understanding global metabolite data," Trends Biotechnol. 22:245-52.

Hill et al. (2008) "Mass spectral metabonomics beyond elemental formula: chemical database querying by matching experimental with computational fragmentation spectra," Anal. Chem. 30:80. 5574-82.

Kataoka et al. (2000) "Applications of solid-phase microextraction in food analysis," J. Chrornatogr. A 880:35-62.

Kerber et al. (2001) "MOLGEN-MS: Evaluation of low resolution electron impact mass spectra with MS classification and exhaustive structure generation," Adv. Mass Spectrom. 15:939-940.

Kim et al. (2012) "A method of finding optimal weight factors for compound identification in gas chromatography-mass spectrometry," Bioinformatics. 28:1158-63.

Lewis et al. (1979) "High resolution gas chromatographic/real-time high resolution mass spectrometric identification of organic acids in human urine," Anal. Chem. 51:1275-1285.

Matsuda et al. (2009) "Assessment of metabolome annotation quality: a method for evaluating the false discovery rate of elemental composition searches," PLoS One. 5:4.7490.

Michalski et al. (2011) "Mass spectrometry-based proteomics using Q Exactive, a high-performance benchtop quadrupole Orbitrap mass spectrometer," Mol. Cell. Proteomics. 10:M111.011.015.

Olsen et al. (2009) "A dual pressure linear ion trap Orbitrap instrument with very 10 high sequencing speed," Mol. Cell. Proteomics. 8:2759-69.

Peterson et al. (2010) "Development and characterization of a GC-enabled QL T-Orbitrap for high resolution and high-mass accuracy GC/MS," Anal. Chem. 82:8618-28.

Peterson et al. (2014) "Development of a GC/Quadrupole-Orbitrap mass spectrometer, part II: new approaches for discovery metabolomics," Anal. Chern. 86:10044-51.

Peterson et al. (2014) "Development of a GC/Quadrupole-Orbitrap mass spectrometer, part I: design and characterization," Anal. Chern. 86:10036-43.20.

Second et al. (2009) "Dual-pressure linear ion trap mass spectrometer improving the analysis of complex protein mixtures," Anal. Chem. 81:7757-65.

Stein (1999) "An integrated method for spectrum extraction and compound identification from gas chromatography/mass spectrometry data," J. Am. Soc. Mass Spectrom. 0305.

Tareke et al. (2002) "Analysis of acrylamide, a carcinogen formed in heated foodstuffs," J. Agric. Food Chem. 4998-5006.

Westerhoff et al. (2005) "Fate of endocrine-disruptor, pharmaceutical, and personal care product chemicals during simulated drinking water treatment processes," Environ. Sci. Technol. 39:6649-6663.

Wolf et al. (2010) "In silica 25 fragmentation for computer assisted identification of metabolite mass spectra," BMC Bioinformatics, 11:148.

Yang et al. (2012) "Comprehensive mass spectrometric mapping of the hydroxylated amino acid residues of the a1 (V) collagen chain," J. Biol. Chem. 287:40598-610.

International Search Report with Written Opinion, dated Jun. 19, 2015, corresponding to International Patent Application No. PCT/US2015/023024.

* cited by examiner

Matching High-Res GC-MS Spectra Against Unit Resolution Reference Libraries

*Deconvolution*
- Raw Data is Grouped into Features
- Spectra Containing Only Peaks from the Same Parent are Assembled
- Unit-Resolution Copy of Each EI Spectrum is Created.

*Spectral Matching*
- Down-Converted EI Spectra are Matched Against a Unit-Res Database
- A Dot Product is Calculated for Every Spectral Comparison
- Top N Best Matches are Stored for each "Unit-Res" GC-Orbitrap Spectrum

*High-Res Filtering*
- For each Spectral Match All Non-Repeating Combinations of Atoms are Generated from each Candidate Parent Molecule
- Exact Mass Fragments are Matched to High-Resolution GC-Orbitrap Spectrum
- % Total Signal in High-Res Spectra Explained by Fragments is returned

Figure 2

1: See Spectral Matching Slide
R is the total number of Reference Spectrum in the Database $$C_2H_2 = [2,2]$$

[0,0]
⋮
[2,2]

| 1. [0,0] | 2. H [0,1] | 3. $H_2$ [0,2] |
|---|---|---|
| 4. C [1,0] | 5. CH [1,1] | 6. $CH_2$ [1,2] |
| 7. $C_2$ [2,0] | 8. $C_2H$ [2,1] | 9. $C_2H_2$ [2,2] |

Figure 7

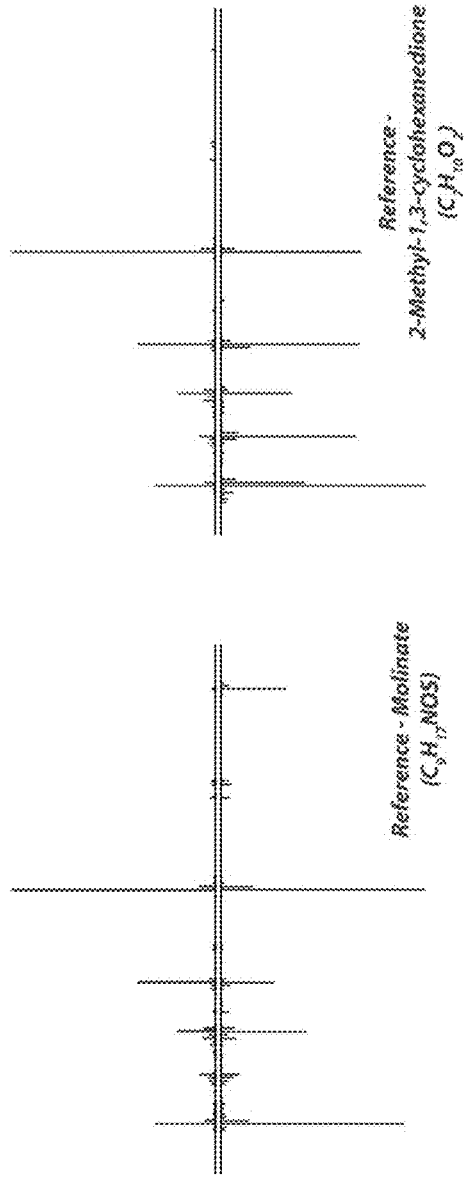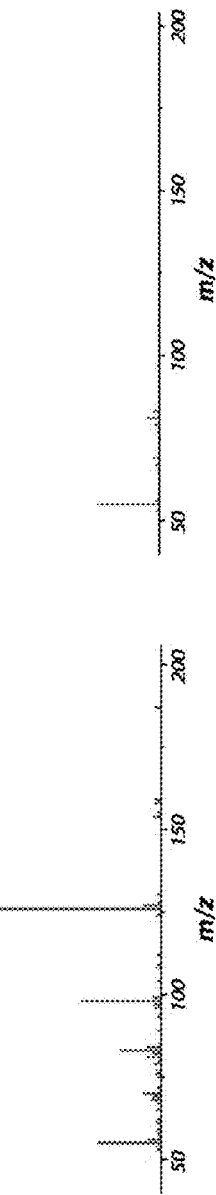
Figure 10

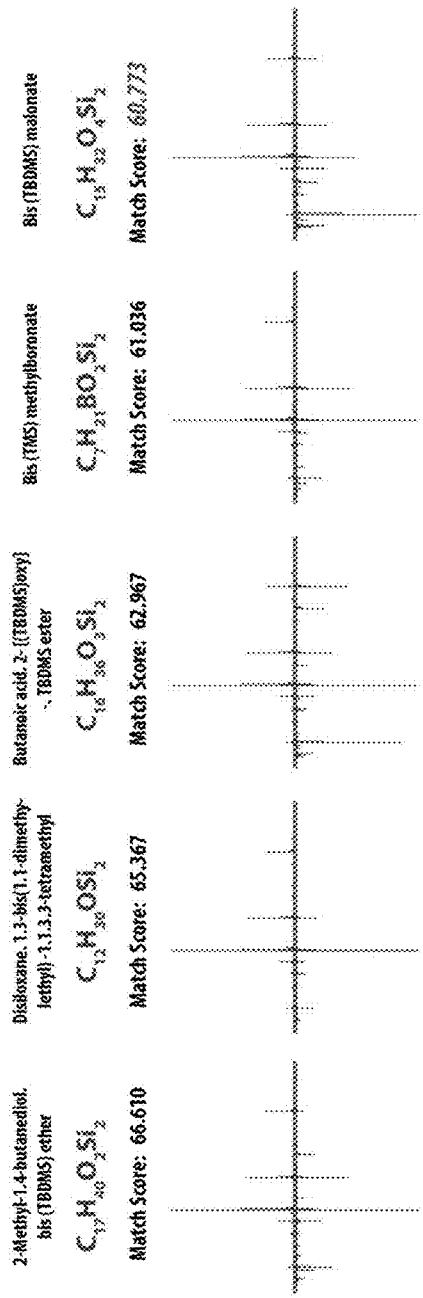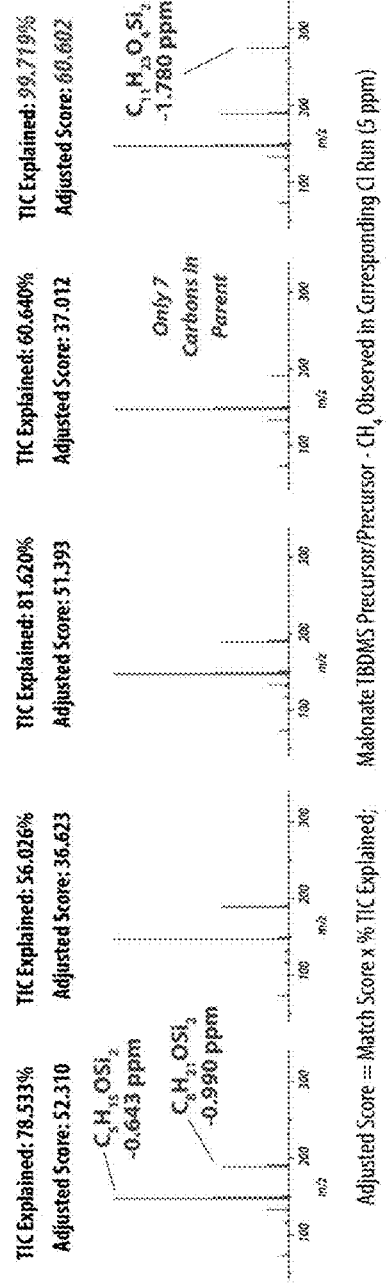
Figure 14

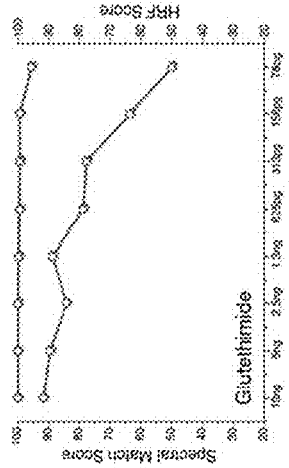
FIG. 24A Amobarbital
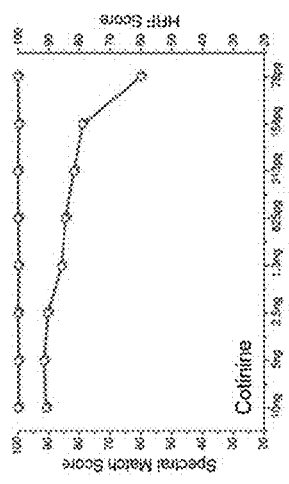
FIG. 24B Cotinine
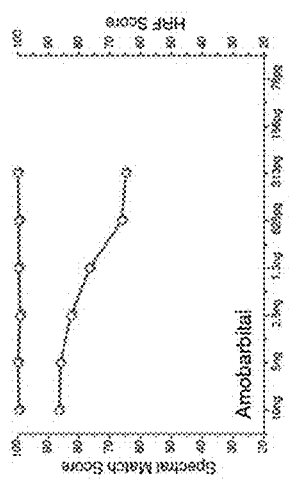
FIG. 24C Glutethimide
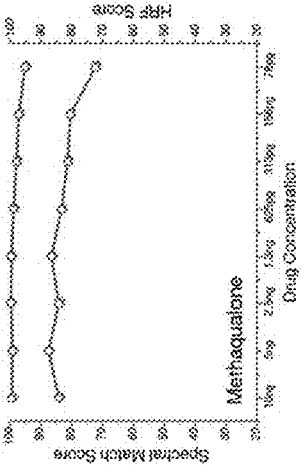
FIG. 24D Loratadine
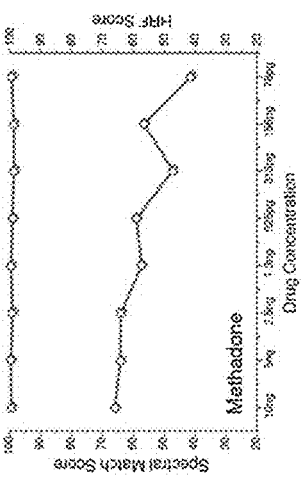
FIG. 24E Methadone
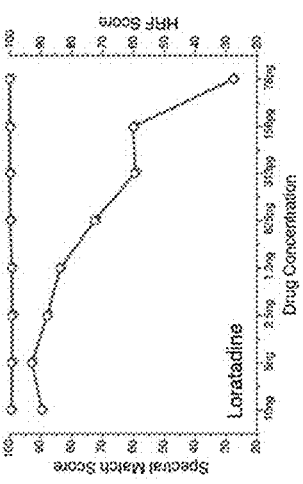
FIG. 24F Methaqualone
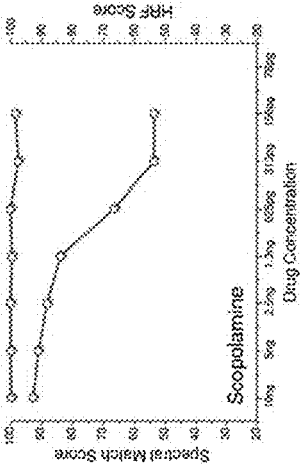
FIG. 24G Nicotine
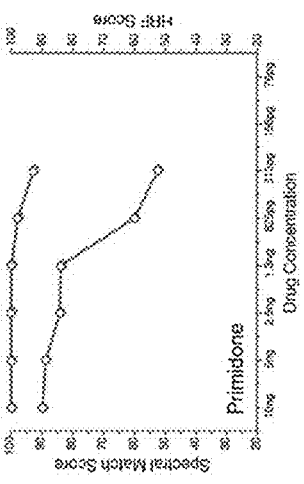
FIG. 24H Primidone
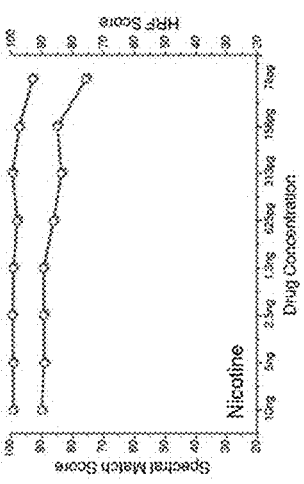
FIG. 24I Scopolamine

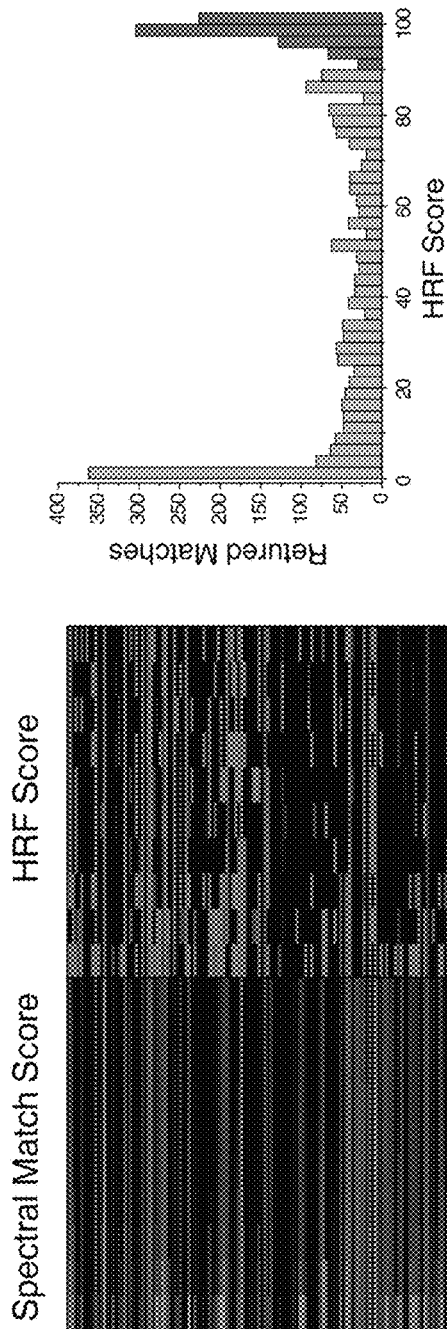
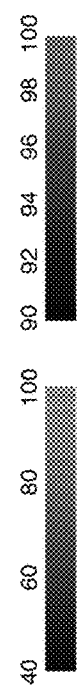
FIG. 27B
FIG. 27A

Supplementary Table 1. Shown here are results from all analyzed reference compounds complete with raw file name, retention time, HRF score, spectral match score, peak count, and the reference spectrum name as reported in NIST 12.

| Name | Raw File | Retention Time | HRF Score | Spectral Match Score | Peak Count | Proper Name (NIST 12 EI Database) |
|---|---|---|---|---|---|---|
| 2'-Deoxyadenosine | AM-3 | 13.353 | 100 | 80.23787 | 121 | 2'-Deoxyadenosine, N-trimethylsilyl-, bis(trimethylsilyl) ether |
| 6-Aminocaproic Acid | AM-4 | 5.958 | 99.85167 | 73.04963 | 114 | Hexanoic acid, 6-amino-, bis(trimethylsilyl) deriv. |
| Acetaminophen | AM-5 | 6.397 | 98.99406 | 85.06104 | 115 | Acetamide, N-(trimethylsilyl)-N-[4-[(trimethylsilyl)oxy]phenyl]- |
| Adenine | AM-5 | 7.27 | 98.48893 | 88.66699 | 90 | 9H-Purin-6-amine, N,9-bis(trimethylsilyl)- |
| Adenosine | AM-4 | 13.555 | 100 | 81.29393 | 117 | Adenosine-tetrakis(trimethylsilyl)- |
| Alachlor | Pest | 14.002 | 100 | 78.14022 | 124 | Alachlor |
| Alanine | AM-6 | 4.162 | 98.73187 | 84.82428 | 42 | l-Alanine, trimethylsilyl ester |
| Ametryn | Pest | 14.186 | 99.37576 | 83.82522 | 125 | Ametryn |
| Amobarbital | 10_Mix_2 | 6.78 | 97.61185 | 86.09109 | 91 | Amobarbital |
| Ascorbic Acid | AM-1 | 7.59 | 99.95632 | 81.42812 | 162 | L-Ascorbic acid, 2,3,5,6-tetrakis-O-(trimethylsilyl)- |
| Aspartic Acid | AM-7 | 6.031 | 100 | 87.35514 | 84 | L-Aspartic acid, N-(trimethylsilyl)-, bis(trimethylsilyl) ester |
| Atraton | Pest | 11.854 | 99.50053 | 85.15589 | 110 | Atraton |
| Atrazine | Pest | 12.125 | 99.71586 | 86.05622 | 108 | Atrazine |
| Beta-Alanine | AM-5 | 4.875 | 98.84262 | 73.69351 | 52 | .beta.-Alanine, N-(trimethylsilyl)-, trimethylsilyl ester |
| Beta-Sitosterol | AM-2 | 19.724 | 99.92321 | 85.28424 | 184 | .beta.-Sitosterol trimethylsilyl ether |
| Bromacil | Pest | 14.663 | 99.84644 | 84.28455 | 70 | Bromacil |
| Butachlor | Pest | 16.759 | 99.91863 | 80.29282 | 115 | Butachlor |
| Butylate | Pest | 7.604 | 98.86798 | 65.56806 | 50 | Carbamothioic acid, bis(2-methylpropyl)-, S-ethyl ester |
| Caffeine | 10_Mix_2 | 7.243 | 99.61229 | 85.29047 | 88 | Caffeine |
| Catechin | AM-1 | 16.591 | 99.92232 | 62.57484 | 111 | 2H-1-Benzopyran, 3,4-dihydro-2-[3,4-bis[(trimethylsilyl)oxy]phenyl]-3,5,7-tris[(trimethylsilyl)oxy]-, (2R-trans)- |
| Chlorpropham | Pest | 10.873 | 99.96756 | 88.86683 | 61 | Chlorpropham |
| Cotinine | 10_Mix_2 | 6.707 | 99.74813 | 90.64544 | 105 | Cotinine |
| Cyanazine | Pest | 15.077 | 99.91903 | 82.52818 | 134 | Cyanazine |
| Cycloate | Pest | 10.583 | 99.07497 | 75.41157 | 68 | Cycloate |
| Cysteine | AM-6 | 6.151 | 99.9446 | 86.59517 | 54 | L-Cysteine, N,S-bis(trimethylsilyl)-, trimethylsilyl ester |
| Cystine | AM-6 | 9.975 | 100 | 82.68418 | 76 | L-Cystine, N,N'-bis(trimethylsilyl)-, bis(trimethylsilyl) ester |
| Diphenamid | Pest | 15.507 | 95.06315 | 73.17383 | 48 | Diphenamid |
| Diphenhydramine | AM-4 | 7.394 | 99.86228 | 76.05572 | 51 | Acetamide, 2,2-diphenyl-N-(2-dimethylamino)ethyl- |

FIG. 29

| | | | | | |
|---|---|---|---|---|---|
| Dopamine | AM-2 | 7.059 | 99.68245 | 86.51747 | 119 | Silanamine, N-[2-[3,4-bis[(trimethylsilyl)oxy]phenyl]ethyl]-1,1,1-trimethyl- |
| EPTC | Pest | 6.557 | 98.66519 | 74.36759 | 44 | Carbamothioic acid, dipropyl-, S-ethyl ester |
| Estriol | AM-2 | 16.455 | 99.96204 | 69.27833 | 137 | Tri(trimethylsilyl) derivative of estriol |
| Estrone | AM-1 | 13.581 | 99.49286 | 84.59311 | 169 | Trimethylsilylestrone |
| Etridiazole | Pest | 7.911 | 100 | 86.52784 | 80 | Etridiazole |
| Fenarimol | Pest | 21.775 | 99.69995 | 78.49869 | 123 | Fenarimol |
| Ferulic Acid | AM-3 | 8.455 | 98.61093 | 82.55173 | 147 | Trimethylsilyl 3-methoxy-4-(trimethylsilyloxy)cinnamate |
| Flavone | AM-3 | 9.495 | 97.29626 | 89.69236 | 79 | Flavone |
| Fluridone | Pest | 24.263 | 97.01718 | 81.5551 | 123 | Fluridone |
| Fumaric Acid | AM-4 | 5.172 | 98.6845 | 53.11481 | 37 | 2-Butenedioic acid (Z)-, bis(trimethylsilyl) ester |
| Gamma Aminobutyric Acid | AM-5 | 6.082 | 100 | 64.91472 | 14 | Butanoic acid, 4-[(trimethylsilyl)amino]-, trimethylsilyl ester |
| Glucosamine | AM-5 | 7.435 | 100 | 85.60832 | 141 | Glucosamine per-TMS |
| Glucose | AM-2 | 7.31 | 100 | 86.02583 | 98 | Glucopyranose, 1,2,3,4,6-pentakis-O-(trimethylsilyl)-, D- |
| Glutamic Acid | AM-7 | 6.337 | 99.58506 | 86.86825 | 96 | Glutamic acid, N-(trimethylsilyl)-, bis(trimethylsilyl) ester, L- |
| Glutamine | AM-6 | 6.856 | 100 | 78.12936 | 96 | l-Glutamine, tris(trimethylsilyl) deriv. |
| Glutaric Acid | AM-5 | 5.507 | 99.88249 | 65.13565 | 54 | Pentanedioic acid, bis(trimethylsilyl) ester |
| Glutethimide | Standard9 | 7.362 | 99.55617 | 92.58142 | 110 | Glutethimide |
| Glyceric Acid | AM-1 | 5.387 | 100 | 80.20763 | 81 | Propanoic acid, 2,3-bis[(trimethylsilyl)oxy]-, trimethylsilyl ester |
| Glycine | AM-5 | 5.321 | 100 | 72.05176 | 33 | Glycine, N,N-bis(trimethylsilyl)-, trimethylsilyl ester |
| Hexazinone | Pest | 19.327 | 99.46783 | 82.67615 | 72 | 1,3,5-Triazine-2,4(1H,3H)-dione, 3-cyclohexyl-6-(dimethylamino)-1-methyl- |
| Histidine | AM-7 | 7.463 | 100 | 75.48915 | 63 | L-Histidine, N,1-bis(trimethylsilyl)-, trimethylsilyl ester |
| Homovanillic Acid | AM-2 | 6.855 | 99.54148 | 81.13459 | 81 | Trimethylsilyl [3-methoxy-4-(trimethylsilyloxy)phenyl]acetate |
| Inositol | AM-5 | 7.797 | 100 | 61.85832 | 135 | Myo-Inositol, pentakis-O-(trimethylsilyl)- |
| Isoleucine | AM-6 | 5.267 | 99.69393 | 86.31592 | 91 | L-Isoleucine, N-(trimethylsilyl)-, trimethylsilyl ester |
| Ketamine | 10_Mix_2 | 7.403 | 99.1702 | 91.45966 | 147 | Ketamine |
| L (+) Lactic Acid | AM-4 | 4.413 | 99.80252 | 73.85199 | 57 | D-(-)-Lactic acid, trimethylsilyl ether, trimethylsilyl ester |
| L-2 Aminobutyric Acid | AM-4 | 4.767 | 99.75521 | 85.93663 | 53 | l-2-Aminobutyric acid, N-trimethylsilyl-, trimethylsilyl ester |
| Loratadine | Standard8 | 18.822 | 99.26171 | 89.68975 | 153 | Loratadine |
| Lysine | AM-6 | 7.473 | 100 | 52.51087 | 90 | L-Lysine, N2,N6,N6-tris(trimethylsilyl)-, trimethylsilyl ester |
| Mandelic Acid | AM-4 | 5.898 | 99.69772 | 91.22946 | 66 | Benzeneacetic acid, .alpha.-[(trimethylsilyl)oxy]-, trimethylsilyl ester |

FIG. 29 Cont.

| | | | | |
|---|---|---|---|---|
| Mescaline | 10_Mix_2 | 8.426 | 99.78119 | 91.25275 | 77 | Acetamide, N-(3,4,5-trimethoxyphenethyl)- |
| Metaqualone | 10_Mix_2 | 9.267 | 98.63943 | 88.19924 | 129 | Methaqualone |
| Methadone | 10_Mix_2 | 9.039 | 99.18112 | 64.81793 | 115 | Methadone |
| Methamphetamine | Unextracted | 4.884 | 98.85648 | 66.2167 | 27 | Methamphetamine |
| Methylmalonic Acid | AM-4 | 4.879 | 99.76899 | 61.44021 | 38 | Propanedioic acid, methyl-, bis(trimethylsilyl) ester |
| Metolachlor | Pest | 14.924 | 100 | 87.14172 | 72 | Metolachlor |
| Metribuzin | Pest | 13.789 | 95.83894 | 78.23404 | 126 | Metribuzin |
| MGK-264 | Pest | 15.554 | 100 | 67.25826 | 95 | N-(2-Ethylhexyl)-5-norbornene-2,3-dicarboximide |
| Minoxidil | Standard2 | 8.374 | 99.86569 | 94.87978 | 118 | Desoxy-minoxidyl |
| Molinate | Pest | 9.232 | 98.57083 | 77.33713 | 48 | Molinate |
| Napropamide | Pest | 17.029 | 98.81199 | 80.58035 | 72 | Napropamide |
| Naproxen | AM-5 | 8.451 | 99.14971 | 88.82363 | 69 | 2-Naphthaleneacetic acid, 6-methoxy-,alpha,-methyl-, trimethylsilyl ester, (+)- |
| Nicotine | 10_Mix_2 | 5.533 | 99.30713 | 90.8779 | 103 | Pyridine, 3-(1-methyl-2-pyrrolidinyl)-, (S)- |
| Norflurazon | Pest | 19.035 | 99.73092 | 83.5459 | 109 | Norflurazon |
| Ornithine | AM-4 | 6.326 | 99.63999 | 80.92918 | 142 | Ornithine, tri-TMS |
| Orotic Acid | AM-5 | 6.74 | 100 | 42.59934 | 33 | 4-Pyrimidinecarboxylic acid, 2,6-bis(trimethylsiloxy)-, trimethylsilyl ester |
| Oxalic Acid | AM-5 | 4.463 | 98.7125 | 65.73171 | 30 | Ethanedioic acid, bis(trimethylsilyl) ester |
| Pebulate | Pest | 8.075 | 97.36806 | 74.74838 | 56 | Pebulate |
| Pipecolinic Acid | AM-4 | 5.538 | 99.5349 | 81.8888 | 75 | 2-Piperidinecarboxylic acid, 1-(trimethylsilyl)-, trimethylsilyl ester |
| Primidone | Standard 4 | 9.896 | 99.88732 | 92.33499 | 95 | Primidone |
| Proline | AM-7 | 5.296 | 99.53685 | 67.4245 | 64 | L-Proline, 1-(trimethylsilyl)-, trimethylsilyl ester |
| Prometon | Pest | 12.014 | 99.46725 | 83.18783 | 76 | Prometon |
| Prometryn | Pest | 14.267 | 99.02092 | 85.43111 | 113 | Prometryn |
| Propachlor | Pest | 10.153 | 99.42461 | 80.98082 | 65 | Acetamide, 2-chloro-N-(1-methylethyl)-N-phenyl- |
| Propazine | Pest | 12.224 | 99.65145 | 82.094 | 99 | Propazine |
| Propyzamide | Pest | 12.571 | 99.64317 | 78.40575 | 77 | Propyzamide |
| Pyroxidine | AM-4 | 7.361 | 100 | 86.25164 | 122 | Pyridine, 2-methyl-3-(trimethylsilyloxy)-4,5-bis-[(trimethylsilyloxy)methyl]- |
| Sarcosine | AM-3 | 4.645 | 99.01318 | 75.64516 | 57 | Bis(trimethylsilyl)sarcosine |
| Serine | AM-7 | 5.497 | 100 | 86.97745 | 83 | Serine, N,O-bis(trimethylsilyl)-, trimethylsilyl ester |
| Simazine | Pest | 11.999 | 100 | 77.02246 | 58 | Simazine |
| Simetryn | Pest | 14.077 | 99.65115 | 85.25555 | 130 | Simetryn |

FIG. 29 Cont.

| | | | | |
|---|---|---|---|---|
| Sinapic Acid | AM-1 | 9.56 | 99.20565 | 67.30941 | 24 | Cinnamic acid, 3,5-dimethoxy-4-(trimethylsiloxy)-, trimethylsilyl ester |
| Succinic Acid | AM-1 | 5.34 | 98.34062 | 69.62375 | 87 | Butanedioic acid, bis(trimethylsilyl) ester |
| Tebuthiuron | Pest | 8.924 | 100 | 79.94081 | 58 | Tebuthiuron |
| Terbacil | Pest | 12.928 | 100 | 83.72495 | 47 | Terbacil |
| Terbutryn | Pest | 14.574 | 99.40774 | 84.2506 | 132 | Terbutryn |
| Threonine | AM-7 | 5.587 | 100 | 90.16955 | 122 | N,O,O-Tris(trimethylsilyl)-L-threonine |
| trans-4-hydroxyproline | AM-6 | 6.057 | 100 | 90.00911 | 78 | L-Proline, 1-(trimethylsilyl)-4-[(trimethylsilyl)oxy]-, trimethylsilyl ester, trans- |
| Triadimefon | Pest | 15.239 | 99.95845 | 69.92398 | 84 | Triadimefon |
| Tricyclazole | Pest | 17.186 | 93.4973 | 79.30223 | 63 | Tricyclazole |
| Trifluralin | Pest | 11.024 | 100 | 66.04019 | 196 | Trifluralin |
| Tryptamine | AM-1 | 7.7 | 98.85996 | 80.35281 | 108 | 1H-Indole-3-ethanamine, N,1-bis(trimethylsilyl)- |
| Tryptophan | AM-7 | 9.323 | 99.9878 | 90.48896 | 72 | L-Tryptophan, N,1-bis(trimethylsilyl)-, trimethylsilyl ester |
| Tyrosine | AM-6 | 7.563 | 100 | 84.23964 | 97 | L-Tyrosine, N,O-bis(trimethylsilyl)-, trimethylsilyl ester |
| Uridine | AM-5 | 11.454 | 99.99264 | 74.19771 | 121 | Uridine, tetra(trimethylsilyl)- |
| Valine | AM-7 | 4.97 | 99.71247 | 89.14675 | 84 | L-Valine, N-(trimethylsilyl)-, trimethylsilyl ester |
| Vernolate | Pest | 7.865 | 98.48952 | 75.4259 | 56 | Carbamothioic acid, dipropyl-, S-propyl ester |

FIG. 29 Cont.

Supplementary Table 2.

| ID Number | Name | Chemical Formula | Monoisotopic Mass | HRF < | Parent Score |
|---|---|---|---|---|---|
| 1 | Methamphetamine | C10H15N | 149.1204 | | 38804 |
| 2 | Alanine (TMS) | C6H15NO2Si | 161.0872 | | 58714 |
| 3 | Nicotine | C10H14N2 | 162.1157 | | 45856 |
| 4 | Cotinine | C10H12N2O | 176.095 | | 48758 |
| 5 | Molinate | C9H17NOS | 187.1031 | | 52685 |
| 6 | Tricyclazole | C9H7N3S | 189.0361 | | 48720 |
| 7 | EPTC | C9H19NOS | 189.1187 | | 55743 |
| 8 | Minoxidil | C9H15N5 | 193.1327 | | 58223 |
| 9 | Caffeine | C8H10N4O2 | 194.0804 | | 57003 |
| 10 | Simazine | C7H12ClN5 | 201.0781 | | 59960 |
| 11 | Pebulate | C10H21NOS | 203.1344 | | 53944 |
| 12 | Vernolate | C10H21NOS | 203.1344 | | 55399 |
| 13 | Propachlor | C11H14ClNO | 211.0764 | | 49306 |
| 14 | Atraton | C9H17N5O | 211.1433 | | 58994 |
| 15 | Chlorpropham | C10H12ClNO2 | 213.0557 | | 57248 |
| 16 | Simetryn | C8H15N5S | 213.1048 | | 59825 |
| 17 | Metribuzin | C8H14N4OS | 214.0888 | | 55724 |
| 18 | Atrazine | C8H14ClN5 | 215.0938 | | 60114 |
| 19 | Cycloate | C11H21NOS | 215.1344 | | 53755 |
| 20 | Terbacil | C9H13ClN2O2 | 216.0666 | | 58040 |
| 21 | Glutethimide | C13H15NO2 | 217.1103 | | 46780 |
| 22 | Butylate | C11H23NOS | 217.15 | | 56103 |
| 23 | Primidone (TMS) | C12H14N2O2 | 218.1055 | | 25420 |
| 24 | Flavone | C15H10O2 | 222.0681 | | 37300 |
| 25 | Prometon | C10H19N5O | 225.159 | | 59327 |
| 26 | Amobarbital | C11H18N2O3 | 226.1317 | | 52802 |
| 27 | Ametryn | C9H17N5S | 227.1205 | | 60045 |
| 28 | Tebuthiuron | C9H16N4OS | 228.1045 | | 57803 |
| 29 | Propazine | C9H16ClN5 | 229.1094 | | 60220 |
| 30 | Beta-Alanine (TMS) | C9H23NO2Si2 | 233.1267 | | 58845 |
| 31 | Sarcosine (TMS) | C9H23NO2Si2 | 233.1267 | | 58980 |
| 32 | Oxalic Acid (TMS) | C8H18O4Si2 | 234.0744 | | 57475 |
| 33 | Lactic Acid (TMS) | C9H22O3Si2 | 234.1107 | | 58614 |
| 34 | Ketamine | C13H16ClNO | 237.092 | | 56362 |

FIG. 30

| | | | |
|---|---|---|---|
| 35 Diphenamid | C16H17NO | 239.131 | 37369 |
| 36 Cyanazine | C9H13ClN6 | 240.089 | 60253 |
| 37 Prometryn | C10H19N5S | 241.1361 | 60093 |
| 38 Terbutryn | C10H19N5S | 241.1361 | 60012 |
| 39 Etridiazole | C5H5Cl3N2OS | 245.9188 | 60503 |
| 40 L-2-Aminobutyric Acid | C10H25NO2Si2 | 247.1424 | 59537 |
| 41 Methaqualone | C16H14N2O | 250.1106 | 50116 |
| 42 Hexazinone | C12H20N4O2 | 252.1586 | 58238 |
| 43 Mescaline | C13H19NO4 | 253.1314 | 52518 |
| 44 Propyzamide | C12H11Cl2NO | 255.0218 | 58544 |
| 45 Proline (TMS) | C11H25NO2Si2 | 259.1424 | 59386 |
| 46 Bromacil | C9H13BrN2O2 | 260.016 | 59918 |
| 47 Fumaric Acid (TMS) | C10H20O4Si2 | 260.09 | 56775 |
| 48 Valine (TMS) | C11H27NO2Si2 | 261.158 | 59442 |
| 49 Methylmalonic Acid ( | C10H22O4Si2 | 262.1057 | 58757 |
| 50 Succinic Acid (TMS) | C10H22O4Si2 | 262.1057 | 58114 |
| 51 Alachlor | C14H20ClNO2 | 269.1183 | 57984 |
| 52 Napropamide | C17H21NO2 | 271.1572 | 52446 |
| 53 Pipecolinic Acid (TMS | C12H27NO2Si2 | 273.158 | 59364 |
| 54 6-Aminocaproic Acid | C12H29NO2Si2 | 275.1737 | 59818 |
| 55 Isoleucine (TMS) | C12H29NO2Si2 | 275.1737 | 59423 |
| 56 MGK-264 | C17H25NO2 | 275.1885 | 54814 |
| 57 Glutaric Acid (TMS) | C11H24O4Si2 | 276.1213 | 59062 |
| 58 Adenine (TMS) | C11H21N5Si2 | 279.1335 | 58826 |
| 59 Diphenhydramine | C18H22N2O | 282.1732 | 45835 |
| 60 Metolachlor | C15H22ClNO2 | 283.1339 | 59613 |
| 61 Glycine (TMS) | C11H29NO2Si3 | 291.1506 | 59405 |
| 62 Triadimefon | C14H16ClN3O2 | 293.0931 | 59909 |
| 63 Acetaminophen (TMS | C14H25NO2Si2 | 295.1424 | 58890 |
| 64 Mandelic Acid (TMS) | C14H24O3Si2 | 296.1264 | 58718 |
| 65 Naproxen (TMS) | C17H22O3Si | 302.1338 | 57397 |
| 66 Norflurazon | C12H9ClF3N3O | 303.0386 | 58917 |
| 67 Tryptamine (TMS) | C16H28N2Si2 | 304.1791 | 59131 |
| 68 Methadone | C21H27NO | 309.2093 | 54863 |
| 69 Butachlor | C17H26ClNO2 | 311.1652 | 58015 |
| 70 Gamma Aminobutyri | C13H33NO2Si3 | 319.1819 | 59603 |
| 71 Serine (TMS) | C12H31NO3Si3 | 321.1612 | 59945 |
| 72 Glyceric Acid (TMS) | C12H30O4Si3 | 322.1452 | 59559 |
| 73 Homovanillic Acid (T | C15H26O4Si2 | 326.137 | 58816 |
| 74 Fluridone | C19H14F3NO | 329.1027 | 57199 |
| 75 Fenarimol | C17H12Cl2N2O | 330.0327 | 58670 |
| 76 Trifluralin | C13H16F3N3O4 | 335.1093 | 60005 |
| 77 Threonine (TMS) | C13H33NO3Si3 | 335.1768 | 59934 |
| 78 Cysteine (TMS) | C12H31NO2SSi3 | 337.1383 | 60044 |
| 79 Ferulic Acid (TMS) | C16H26O4Si2 | 338.137 | 58658 |
| 80 Estrone (TMS) | C21H30O2Si | 342.2015 | 58774 |
| 81 Trans-4-Hydroxyproli | C14H33NO3Si3 | 347.1768 | 60138 |

FIG. 30 Cont.

| # | Compound | Formula | Mass | Value |
|---|---|---|---|---|
| 82 | Ornithine (TMS) | C14H36N2O2Si3 | 348.2085 | 60235 |
| 83 | Aspartic Acid (TMS) | C13H31NO4Si3 | 349.1561 | 60081 |
| 84 | Glutamine (TMS) | C14H34N2O3Si3 | 362.1877 | 60357 |
| 85 | Glutamic Acid (TMS) | C14H33NO4Si3 | 363.1717 | 59782 |
| 86 | Sinapic Acid (TMS) | C17H28O5Si2 | 368.1475 | 57349 |
| 87 | Dopamine (TMS) | C17H35NO2Si3 | 369.1976 | 59815 |
| 88 | Histidine (TMS) | C15H33N3O2Si3 | 371.1881 | 60263 |
| 89 | Orotic Acid (TMS) | C14H28N2O4Si3 | 372.1357 | 59701 |
| 90 | Loratadine | C22H23ClN2O2 | 382.1448 | 58320 |
| 91 | Pyroxidine (TMS) | C17H35NO3Si3 | 385.1925 | 60013 |
| 92 | Tyrosine (TMS) | C18H35NO3Si3 | 397.1925 | 59986 |
| 93 | Tryptophan (TMS) | C20H36N2O2Si3 | 420.2085 | 60117 |
| 94 | Lysine (TMS) | C18H46N2O2Si4 | 434.2636 | 60292 |
| 95 | Ascorbic Acid (TMS) | C18H40O6Si4 | 464.1902 | 60098 |
| 96 | 2'-Deoxyadenosine (TMS) | C19H37N5O3Si3 | 467.2204 | 60406 |
| 97 | Beta-Sitosterol (TMS) | C32H58OSi | 486.4257 | 60362 |
| 98 | Estriol (TMS) | C27H48O3Si3 | 504.2911 | 60141 |
| 99 | Cystine (TMS) | C18H44N2O4S2Si4 | 528.182 | 60182 |
| 100 | Uridine (TMS) | C21H44N2O6Si4 | 532.2276 | 60226 |
| 101 | Glucose (TMS) | C21H52O6Si5 | 540.261 | 59997 |
| 102 | Inositol (TMS) | C21H52O6Si5 | 540.261 | 59946 |
| 103 | Adenosine (TMS) | C22H45N5O4Si4 | 555.2549 | 60394 |
| 104 | Glucosamine (TMS) | C24H61NO5Si6 | 611.3165 | 60276 |
| 105 | Catechin (TMS) | C30H54O6Si5 | 650.2767 | 60278 |
| | Average | | 298.8377 | 56998.6476 |

FIG. 30 Cont.

| ID Number | HRF ? Pare | True Super | False Supe | Percent of | Avg. Additi | Median Additional Atc |
|---|---|---|---|---|---|---|
| 1 | 21756 | 20004 | 1752 | 95.7785 | 11.5228 | 11 |
| 2 | 1846 | 1705 | 141 | 91.3475 | 17.6241 | 16 |
| 3 | 14704 | 14081 | 623 | 95.9007 | 27.8042 | 25 |
| 4 | 11802 | 10994 | 808 | 95.8515 | 23.3837 | 22 |
| 5 | 7875 | 3271 | 4604 | 96.1847 | 29.7068 | 26 |
| 6 | 11840 | 3640 | 8200 | 92.2787 | 27.109 | 23 |
| 7 | 4817 | 2610 | 2207 | 96.3883 | 27.836 | 24 |
| 8 | 2337 | 1272 | 1065 | 94.3694 | 29.3765 | 25 |
| 9 | 3557 | 1999 | 1558 | 94.6834 | 28.1573 | 24 |
| 10 | 600 | 445 | 155 | 91.3548 | 29.0129 | 25 |
| 11 | 6616 | 2005 | 4611 | 93.5085 | 21.077 | 16 |
| 12 | 5161 | 2008 | 3153 | 93.3052 | 20.2851 | 14 |
| 13 | 11254 | 2869 | 8385 | 95.9826 | 24.3171 | 21 |
| 14 | 1566 | 1272 | 294 | 95.2594 | 28.6939 | 25 |
| 15 | 3312 | 2326 | 986 | 94.3634 | 17.3824 | 13 |
| 16 | 735 | 418 | 317 | 93.854 | 32.3849 | 29 |
| 17 | 4836 | 832 | 4004 | 91.6637 | 22.0844 | 18 |
| 18 | 446 | 346 | 100 | 93.4643 | 25.81 | 23 |
| 19 | 6805 | 1966 | 4839 | 93.5488 | 19.554 | 14 |
| 20 | 2520 | 1461 | 1059 | 91.5993 | 12.1681 | 10 |
| 21 | 13780 | 11879 | 1901 | 95.1825 | 15.9495 | 13 |
| 22 | 4457 | 1534 | 2923 | 93.4305 | 19.6914 | 14 |
| 23 | 35140 | 8596 | 26544 | 92.9682 | 22.3994 | 17 |
| 24 | 23260 | 19328 | 3932 | 92.4165 | 15.2411 | 13 |
| 25 | 1233 | 1022 | 211 | 95.2607 | 29.3507 | 26 |
| 26 | 7758 | 4579 | 3179 | 91.8019 | 12.2051 | 9 |
| 27 | 515 | 263 | 252 | 94.8413 | 31.0397 | 28 |
| 28 | 2757 | 674 | 2083 | 93.5979 | 14.1195 | 12 |
| 29 | 340 | 269 | 71 | 94.3662 | 27.3944 | 24 |
| 30 | 1715 | 998 | 717 | 89.3211 | 18.7169 | 16 |
| 31 | 1580 | 985 | 595 | 90.3747 | 19.5126 | 17 |
| 32 | 3085 | 1183 | 1902 | 90.2964 | 23.8312 | 19 |
| 33 | 1946 | 1606 | 340 | 94.3301 | 20.4647 | 19 |
| 34 | 4198 | 2001 | 2197 | 96.5507 | 26.6359 | 22 |

FIG. 30 Cont.

| | | | | | | |
|---|---|---|---|---|---|---|
| 35 | 23191 | 11476 | 11715 | 90.584 | 13.4525 | 9 |
| 36 | 307 | 167 | 140 | 92.734 | 26 | 22 |
| 37 | 467 | 235 | 232 | 95.1355 | 29.1853 | 26 |
| 38 | 548 | 237 | 311 | 94.8002 | 26.9936 | 24 |
| 39 | 57 | 53 | 4 | 94.1176 | 27.5 | 29 |
| 40 | 1023 | 807 | 216 | 93.7847 | 16.0463 | 14 |
| 41 | 10444 | 8436 | 2008 | 94.7392 | 22.4158 | 17 |
| 42 | 2322 | 1556 | 766 | 96.2931 | 23.4021 | 20 |
| 43 | 8042 | 4640 | 3402 | 95.4717 | 21.1822 | 16 |
| 44 | 2016 | 1142 | 874 | 94.8216 | 21.7654 | 17 |
| 45 | 1174 | 893 | 281 | 93.9328 | 16.4484 | 15 |
| 46 | 642 | 493 | 149 | 91.9215 | 9.8121 | 9 |
| 47 | 3785 | 1148 | 2637 | 89.227 | 21.1331 | 17 |
| 48 | 1118 | 843 | 275 | 93.6406 | 14.8473 | 13 |
| 49 | 1803 | 1052 | 751 | 92.5258 | 25.1225 | 22 |
| 50 | 2446 | 1110 | 1336 | 88.8946 | 21.1198 | 18 |
| 51 | 2576 | 730 | 1846 | 96.8609 | 24.0785 | 21 |
| 52 | 8114 | 6542 | 1572 | 95.3345 | 13.4135 | 11 |
| 53 | 1196 | 852 | 344 | 93.7962 | 15.8052 | 14 |
| 54 | 742 | 594 | 148 | 94.2274 | 16.6081 | 14 |
| 55 | 1137 | 795 | 342 | 93.3384 | 14.6316 | 13 |
| 56 | 5746 | 5135 | 611 | 96.1193 | 11.784 | 10 |
| 57 | 1498 | 1014 | 484 | 95.7821 | 22.6054 | 20 |
| 58 | 1734 | 69 | 1665 | 90.4166 | 27.5003 | 23 |
| 59 | 14725 | 4299 | 10426 | 84.7088 | 7.9011 | 6 |
| 60 | 947 | 514 | 433 | 95.888 | 11.7506 | 10 |
| 61 | 1155 | 464 | 691 | 89.8855 | 18.4732 | 16 |
| 62 | 651 | 444 | 207 | 95.9608 | 20.6957 | 20 |
| 63 | 1670 | 856 | 814 | 93.0618 | 17.9853 | 16 |
| 64 | 1842 | 1294 | 548 | 93.2694 | 14.8467 | 12 |
| 65 | 3163 | 1658 | 1505 | 95.4431 | 18.5907 | 16 |
| 66 | 1643 | 142 | 1501 | 92.7382 | 20.948 | 18 |
| 67 | 1429 | 389 | 1040 | 93.6819 | 19.0288 | 15 |
| 68 | 5697 | 3917 | 1780 | 95.1674 | 10.2607 | 9 |
| 69 | 2545 | 310 | 2235 | 97.1612 | 23.7154 | 20 |
| 70 | 957 | 420 | 537 | 90.689 | 15.5512 | 14 |
| 71 | 615 | 337 | 278 | 93.5396 | 16.4209 | 14 |
| 72 | 1001 | 592 | 409 | 96.3325 | 22.423 | 19 |
| 73 | 1744 | 875 | 869 | 94.3344 | 21.901 | 19 |
| 74 | 3361 | 896 | 2465 | 91.1605 | 25.9639 | 22 |
| 75 | 1890 | 409 | 1481 | 94.6042 | 18.7164 | 15 |
| 76 | 555 | 100 | 455 | 95.2156 | 18.6286 | 16 |
| 77 | 626 | 343 | 283 | 93.5062 | 15.1307 | 13 |
| 78 | 516 | 43 | 473 | 95.6321 | 24.3446 | 20 |
| 79 | 1902 | 833 | 1069 | 93.7208 | 20.5762 | 18 |
| 80 | 1786 | 1190 | 596 | 95.6687 | 17.1879 | 15 |
| 81 | 422 | 217 | 205 | 92.8455 | 14.7902 | 13 |

FIG. 30 Cont.

| | | | | | | |
|---|---|---|---|---|---|---|
| 82 | 325 | 160 | 165 | 94.992 | 16.6606 | 16 |
| 83 | 479 | 236 | 243 | 95.4653 | 20.5802 | 18 |
| 84 | 203 | 128 | 75 | 95.8571 | 18.9067 | 18 |
| 85 | 778 | 265 | 513 | 93.0214 | 19.4464 | 17 |
| 86 | 3211 | 516 | 2695 | 92.4176 | 21.7295 | 19 |
| 87 | 745 | 325 | 420 | 94.1092 | 13.6762 | 11 |
| 88 | 297 | 65 | 232 | 96.2284 | 21.8017 | 19 |
| 89 | 859 | 104 | 755 | 91.4427 | 20.3166 | 17 |
| 90 | 2240 | 210 | 2030 | 95.5911 | 23.8813 | 20 |
| 91 | 547 | 307 | 240 | 94.5833 | 13.25 | 11 |
| 92 | 574 | 280 | 294 | 95.3231 | 13.6224 | 11 |
| 93 | 443 | 111 | 332 | 95.9839 | 17.6175 | 14 |
| 94 | 268 | 37 | 231 | 95.9536 | 19.1255 | 16 |
| 95 | 462 | 153 | 309 | 94.5365 | 21.5049 | 18 |
| 96 | 154 | 20 | 134 | 95.1771 | 21.0448 | 19 |
| 97 | 198 | 140 | 58 | 97.2639 | 14.0517 | 13 |
| 98 | 419 | 188 | 231 | 95.6443 | 13.4069 | 12 |
| 99 | 378 | 4 | 374 | 89.6661 | 14.7326 | 12 |
| 100 | 334 | 20 | 314 | 87.1329 | 7.8822 | 5 |
| 101 | 563 | 58 | 505 | 89.2621 | 10.2832 | 7 |
| 102 | 614 | 58 | 556 | 89.8296 | 10.4011 | 7 |
| 103 | 166 | 8 | 158 | 91.0997 | 10.1646 | 7 |
| 104 | 284 | 10 | 274 | 82.922 | 4.6934 | 4 |
| 105 | 282 | 10 | 272 | 93.6416 | 8.8272 | 7 |
| 3561.3524 | 1946.81 | 1614.543 | 93.5741 | 19.506 | 16.581 | |

FIG. 30 Cont.

Supplementary Table 3. Shown here are the associated spectral match score, HRF score, and peak count for all extracted spectra in the drug spike-in dataset. All spectra considered contained at least 10 peaks.

| Drug Name | Concentration | Spectral Match | HRF Score | Peak Count |
|---|---|---|---|---|
| Nicotine | 10 ng | 89.82369 | 99.17881 | 101 |
| Nicotine | 5 ng | 89.21242 | 99.22686 | 95 |
| Nicotine | 2.5 ng | 89.2211 | 99.34258 | 97 |
| Nicotine | 1 ng | 89.2658 | 99.01598 | 82 |
| Nicotine | 625 pg | 86.08654 | 97.86442 | 68 |
| Nicotine | 313 pg | 83.82492 | 99.35862 | 52 |
| Nicotine | 162 pg | 85.98935 | 97.18288 | 66 |
| Nicotine | 80 pg | 75.55134 | 92.77129 | 34 |
| Cotinine | 10 ng | 90.87393 | 99.81463 | 96 |
| Cotinine | 5 ng | 91.49133 | 99.75887 | 98 |
| Cotinine | 2.5 ng | 90.26395 | 99.94532 | 91 |
| Cotinine | 1 ng | 85.73789 | 99.76351 | 66 |
| Cotinine | 625 pg | 84.45779 | 99.91503 | 57 |
| Cotinine | 313 pg | 81.61932 | 100 | 40 |
| Cotinine | 162 pg | 78.77733 | 99.79162 | 39 |
| Cotinine | 80 pg | 59.86455 | 100 | 23 |
| Amobarbital | 10 ng | 86.61869 | 99.69883 | 85 |
| Amobarbital | 5 ng | 86.22043 | 100 | 70 |
| Amobarbital | 2.5 ng | 82.61674 | 99.32243 | 44 |
| Amobarbital | 1 ng | 76.55431 | 99.67943 | 48 |
| Amobarbital | 625 pg | 66.17535 | 99.73096 | 35 |
| Amobarbital | 313 pg | 64.85207 | 100 | 18 |
| Amobarbital | 162 pg | No Spectrum | No Spectrum | No Spectrum |
| Amobarbital | 80 pg | No Spectrum | No Spectrum | No Spectrum |
| Gluethimide | 10 ng | 91.73291 | 100 | 89 |
| Gluethimide | 5 ng | 89.60455 | 99.93778 | 69 |
| Gluethimide | 2.5 ng | 84.1814 | 100 | 38 |
| Gluethimide | 1 ng | 88.73444 | 99.84825 | 59 |
| Gluethimide | 625 pg | 78.63416 | 99.54788 | 30 |
| Gluethimide | 313 pg | 77.581 | 99.3464 | 31 |
| Gluethimide | 162 pg | 63.58836 | 99.43759 | 17 |
| Gluethimide | 80 pg | 49.96783 | 95.58267 | 12 |
| Methadone | 10 ng | 66.05668 | 99.58029 | 100 |
| Methadone | 5 ng | 64.20798 | 99.68237 | 92 |
| Methadone | 2.5 ng | 64.03547 | 99.2299 | 88 |
| Methadone | 1 ng | 57.32097 | 99.69799 | 63 |
| Methadone | 625 pg | 59.02508 | 99.18545 | 70 |
| Methadone | 313 pg | 47.20419 | 98.70877 | 59 |
| Methadone | 162 pg | 56.5431 | 98.75955 | 54 |
| Methadone | 80 pg | 41.49079 | 99.38454 | 25 |
| Methaqualone | 10 ng | 84.13078 | 99.38832 | 92 |
| Methaqualone | 5 ng | 87.4992 | 99.24683 | 98 |
| Methaqualone | 2.5 ng | 84.18102 | 99.64644 | 89 |

FIG. 31

| | | | | |
|---|---|---|---|---|
| Methaqualone | 1 ng | 86.51924 | 99.51907 | 89 |
| Methaqualone | 625 pg | 83.29513 | 98.77386 | 82 |
| Methaqualone | 313 pg | 81.31826 | 97.85804 | 66 |
| Methaqualone | 162 pg | 80.40196 | 97.09529 | 84 |
| Methaqualone | 80 pg | 72.31447 | 95.20307 | 41 |
| Scopolamine | 10 ng | 92.70723 | 99.82007 | 87 |
| Scopolamine | 5 ng | 90.92564 | 100 | 79 |
| Scopolamine | 2.5 ng | 88.18741 | 100 | 61 |
| Scopolamine | 1 ng | 83.65214 | 99.53964 | 52 |
| Scopolamine | 625 pg | 66.42922 | 100 | 35 |
| Scopolamine | 313 pg | 53.5959 | 97.49234 | 17 |
| Scopolamine | 162 pg | 53.45593 | 98.32571 | 24 |
| Scopolamine | 80 pg | No Spectrum | No Spectrum | No Spectrum |
| Primidone | 10 ng | 89.72626 | 99.78106 | 66 |
| Primidone | 5 ng | 88.58776 | 99.78101 | 62 |
| Primidone | 2.5 ng | 84.03984 | 99.76632 | 53 |
| Primidone | 1 ng | 83.67805 | 99.74081 | 42 |
| Primidone | 625 pg | 59.92945 | 97.64044 | 24 |
| Primidone | 313 pg | 52.30685 | 92.53424 | 20 |
| Primidone | 162 pg | No Spectrum | No Spectrum | No Spectrum |
| Primidone | 80 pg | No Spectrum | No Spectrum | No Spectrum |
| Loratidine | 10 ng | 89.57203 | 99.53398 | 149 |
| Loratidine | 5 ng | 92.88445 | 99.413 | 151 |
| Loratidine | 2.5 ng | 87.91399 | 99.3452 | 128 |
| Loratidine | 1 ng | 83.65915 | 99.45562 | 86 |
| Loratidine | 625 pg | 72.5576 | 99.83844 | 53 |
| Loratidine | 313 pg | 59.45031 | 100 | 29 |
| Loratidine | 162 pg | 60.01962 | 100 | 34 |
| Loratidine | 80 pg | 32.68794 | 100 | 10 |

FIG. 31 Cont.

HIGH MASS ACCURACY FILTERING FOR IMPROVED SPECTRAL MATCHING OF HIGH-RESOLUTION GAS CHROMATOGRAPHY-MASS SPECTROMETRY DATA AGAINST UNIT-RESOLUTION REFERENCE DATABASES

CROSS-REFERENCE TO RELATED APPLICATIONS

This application claims the benefit of U.S. Provisional Application No. 61/972,073, filed Mar. 28, 2014, which is hereby incorporated by reference in its entirety to the extent not inconsistent herewith.

STATEMENT REGARDING FEDERALLY SPONSORED RESEARCH OR DEVELOPMENT

This invention was made with government support under GM107199 awarded by the National Institutes of Health. The government has certain rights in the invention.

BACKGROUND OF INVENTION

Gas chromatography mass spectrometry (GC-MS) experiments separate small molecules on a GC column coupled to an ionization source. After ionization, the molecules are then mass analyzed. One typical ionization methods is electron ionization (EI) which causes molecules to fragment in reproducible patterns which are useful for analyte identification. Typically, user-generated EI spectra are identified by spectral matching against databases of reference spectra, including several existing databases of EI spectra generated from pure compounds collected on unit-resolution mass spectrometers (i.e., ~1 Da reference libraries provided by NIST, Wiley, etc.).

However, this method can lead to ambiguity in assigned identifications of analytes due to the poor specificity of unit-resolution spectra. There are many cases where distinct compounds generate similar EI spectra, leading to a high number of false identifications. Furthermore, the degree of spectral similarity between observed and reference spectra, the metric used to assign identification confidence, is ambiguous and subject to human judgment.

Previously, researchers have constructed a high-resolution GC-Orbitrap mass spectrometer capable of collecting high-resolution EI spectra (see, for example, Peterson et al., "Development and characterization of a GC-enabled QLT-Orbitrap for High-resolution and high-mass accuracy GC/MS," Anal. Chem., 2010, 82(20):8618-28). However, currently available spectra libraries (such as provided by NIST and Wiley) do not contain high-resolution spectra and instead remain as unit-resolution libraries.

What is needed is a method of enabling high-resolution spectral matching using currently available unit-resolution reference libraries. These available databases contain hundreds of thousands of reference spectra which would be prohibitively costly to recreate using high-resolution GC-MS instruments. The invention presented herein provides a means to leverage high-resolution spectra to achieve superior spectral matching specificity with such existing resources. Using high-resolution accurate mass measurements would increase spectral match confidence without the need for high-resolution reference libraries.

Others have used predictive fragmentation models (i.e., theoretical high-resolution spectra generated by algorithms that carry out predictive in silico fragmentation) in an attempt to increase specificity in spectral matching. Using this approach, known molecular structures and bonding energies are used to develop algorithms that predict EI fragmentation. Very rarely, if ever, are these algorithms able to generate spectra which correlate exactly with experimentally measured spectra. Often the predictive spectra are extremely dissimilar to their measured analogs leading to an increased possibility of false identifications. An embodiment of the present method starts with experimentally observed patterns in measured reference data, maintaining important peak and intensity relationships that are not easily accounted for in predictive models.

The present invention provides methods and systems for analyzing data obtained from a high-resolution mass spectrometer using unit-resolution spectral data in combination with additional filtering and scoring steps. Moreover, the present invention enables high-resolution matching using currently available unit-resolution reference libraries. These available databases contain hundreds of thousands of reference spectra that would be cost prohibitive to recreate using high-resolution GC-MS instruments. Thus, the invention allows the use of newly obtained high-resolution spectra to achieve superior spectral matching specificity with existing resources.

The invention presented herein is a useful tool to increase compound identification using obtained high-resolution mass spectra, such as spectra obtained during GC-MS. In an embodiment, for example, the methods of the present invention start with experimentally observed patterns in measured reference data, which maintains important peak and intensity relationships that are not easily accounted for in predictive models. Accordingly, aspects of the methods and systems described herein are complementary, or superior, to spectral matching done against theoretical high-resolution spectra generated by certain conventional algorithms.

SUMMARY OF THE INVENTION

The invention provides methods, systems and algorithms for identifying high-resolution mass spectra. In some embodiments, an analyte is ionized and analyzed using high-resolution mass spectrometry (MS) at high mass accuracy (such as $\leq 75$ ppm or $\leq 30$ ppm) and the obtained mass spectra are matched with one or more prospective candidate molecules or chemical formulas. The invention provide, for example, methods and systems wherein the possible fragments that can be generated from the candidate molecules or chemical formulas are determined as well as the masses of each of these fragments. The invention provide, for example, methods and systems wherein the high-resolution mass spectra are then compared with the calculated fragment masses for each of the candidate molecules or chemical formula, and the portion of the high-resolution mass spectra that corresponds or can be explained by the calculated fragment masses is determined. The invention provide, for example, methods and systems wherein based on the amount of the high-resolution mass spectra that corresponds or can be explained by the calculated fragment masses, the analyte is identified as the candidate molecule or as having the chemical formula, or the candidate molecule or chemical formula is eliminated as a possible identification.

In one aspect of the invention, the obtained mass spectra of the analyte are matched with one or more candidate molecules using reference libraries or databases, including unit-resolution libraries and databases, which contain mass spectra of the candidate molecules. The high-resolution mass spectra can be matched to unit-resolution databases by converting the high-resolution spectra into lower resolution spectra, such as by rounding peak m/z values to the nearest whole integer. The returned spectral matches can still be ambiguous, but the additional steps of calculating the fragment masses for each candidate molecule and comparing the high-resolution mass spectra with the calculated fragment masses can now be employed to increase identification rate.

For example, the top compounds matched from the reference database can be stored, and for each putative identification all non-repeating combinations of atoms are generated from its molecular formula. After generating each set of fragments, and optionally filtering away impossible formulas, these chemical fragments are matched against the high-resolution spectrum at high mass accuracy. From here, it is determined what amount of the spectrum can be explained by each set of chemical fragments.

One embodiment of the invention provides a method of analyzing an analyte in a sample using mass spectrometry comprising:

(a) measuring a fragmentation spectrum for said analyte using a mass spectrometry technique providing a mass accuracy equal to or less than 75 ppm; wherein said fragmentation spectrum comprises a plurality of peaks corresponding to measured mass-to-charge ratios of fragment ions from said sample; wherein said fragmentation spectrum is characterized by a signal parameter corresponding to said peaks of said fragmentation spectrum;

(b) providing a candidate molecule for analysis of said fragmentation spectrum of said analyte;

(c) determining putative fragment masses for possible fragment ions from said candidate molecule; and (d) comparing the putative fragment masses of said candidate molecule to the measured mass-to-charge ratios from said fragmentation spectrum to determine a signal parameter similarity of the fragmentation spectrum that matches the putative fragment masses of said candidate molecule, thereby analyzing said analyte using mass spectrometry.

In an embodiment of this aspect, for example, the mass accuracy is equal to or less than 30 ppm and optionally for some embodiments equal to or less than 10 ppm. In an embodiment of this aspect, putative fragment masses for all possible fragment ions from said candidate molecule are determined.

In further embodiments, the putative fragment masses are determined for all possible fragment ions from the candidate molecule and compared to the measured mass-to-charge ratios. Additionally, the putative fragment masses can be determined for all non-repeating combinations of atoms of the molecular formula of the candidate molecule.

The signal parameter includes, but is not limited to, the number of peaks in a spectrum, the intensity or strength of the peaks, the total ion current (TIC) corresponding to the sum of the peaks, and the m/z values of the peaks. Accordingly, determining signal parameter similarity between the fragmentation spectrum and the putative fragment masses of the candidate molecules includes, but is not limited to, the number of successfully matched peaks, the percent of matched peaks, the sum of all matched peak m/z values times their individual intensities, and the percentage of the TIC for peaks that match. In one embodiment, the signal parameter is the total ion current (TIC) corresponding to the sum of the peaks of the fragmentation spectrum, and the signal parameter similarity is the percentage of the TIC of the fragmentation spectrum corresponding to peaks that match one or more the putative fragment masses of the candidate molecule.

In an embodiment, for each measured m/z peak in a spectrum, a defined mass tolerance centered around the peak's m/z value is created at a selected ppm tolerance, for example, to within 30 ppm, to within 15 ppm, to within 1 ppm, or in some embodiments to within less than 1 ppm (e.g., 0.5 ppm or 0.1 ppm). Putative fragment masses from a given candidate molecule are matched to peaks, for example, by comparing the putative masses to observed peaks in the fragmentation spectrum using a selected ppm tolerance. For example, any peak having a putative fragment falling within its defined mass tolerance is considered "matched." "Signal parameter similarity" is a parameter quantifying the peaks which have been successfully matched in a spectrum relative to those which have not been "matched" and, for example, may include the number of matched peaks, the percentage of matched peaks, the percentage of signal intensity corresponding to the matched peaks, etc.

Preferably for some embodiments, the mass spectrometry technique provides a mass accuracy equal to or less than 30 ppm, equal to or less than 20 ppm, equal to or less than 10 ppm, or equal to or less than 5 ppm. In one embodiment, a peak in the fragmentation spectrum corresponding to measured mass-to-charge ratios matches a putative fragment mass when it is within 30 ppm of the putative fragment mass, more preferably for some examples to within 20 ppm, more preferably for some examples to within 10 ppm, or more preferably for some examples to within 5 ppm. In one embodiment, the percentage of the TIC that matches the putative fragment masses corresponds peaks that match at least one putative fragment mass to within 30 ppm, more preferably for some examples to within 20 ppm, more preferably for some examples to within 10 ppm, or more preferably for some examples to within 5 ppm. In an embodiment, the signal parameter similarity is the number of peaks in the fragmentation spectrum that match the putative fragment masses for a candidate molecule. In an embodiment, the signal parameter similarity is the total ion current (TIC) of peaks in the fragmentation spectrum that match the putative fragment masses for a candidate molecule.

Optionally, the candidate molecule is selected via matching the fragmentation spectrum with one or more reference spectra in a reference spectra database, or where the candidate molecule corresponds to a target compound for analysis in the sample, or where the candidate molecule corresponds to one or more desired candidate chemical formulas.

One embodiment comprises calculating the spectral overlap between the fragmentation spectrum of the analyte and a reference spectrum of one or more candidate molecules. The reference spectrum can be a low resolution reference spectrum or a high-resolution reference spectrum. If the reference spectrum is a lower resolution spectrum, such as a unit-resolution spectrum, calculating the spectral overlap preferably comprises rounding all peak m/z values of the fragmentation spectrum to the nearest integer value.

Optionally, determining the spectral overlap between the fragmentation spectrum and the reference spectrum comprises generating a spectral overlap score, such as using a dot product calculation. The signal spectral overlap score and the signal parameter similarity can additionally be combined to provide an indication or numerical value of the likelihood that the analyte corresponds to the candidate molecule. For example, in one embodiment, the spectral overlap score and the percentage of the TIC of the fragmentation spectrum that matches the putative fragment masses are combined to generate a high-resolution filtered score for the candidate molecule with respect to the analyte. In an embodiment, the spectral overlap score and the percentage of the TIC of the fragmentation spectrum that matches the putative fragment masses are combined by multiplying the spectral overlap score and the percentage of the TIC of the fragmentation spectrum that matches the putative fragment masses.

In an embodiment, "spectral overlap score" is a parameter to quantify the similarity between two mass spectra. In an instance, for example these spectra are an experimentally derived GC-MS EI spectrum and a reference GC-MS EI spectrum. Any mathematical calculation which produces as a result some value which is representative of how similar two spectra are to one another can be used in the context of this invention. In one embodiment of this invention experimentally derived spectra are compared against a large number of reference GC-MS EI spectra. To identify those reference spectra which are most similar to the measured spectrum a spectral overlap score (e.g., a weighted dot product as defined herein) is calculated for all, and reference spectra with the highest scores are returned. Using chemical formulas from these returned candidates a corresponding high-resolution filtered score is calculated, for example, as described further below. These two scoring metrics can be considered independently, in conjunction with one another, or in conjunction with a number of other metrics to determine the soundness of a returned identification. The aforementioned metrics can be evaluated independently or combined mathematically to give a single, or multiple numerical representations of the quality of returned identification.

One embodiment of the invention comprises the step of providing a plurality of different candidate molecules for analysis. Putative fragment masses are independently determined for each of the candidate molecules and independently compared to the signal parameter from the fragmentation spectrum, thereby determining signal parameter similarity for each of the candidate molecules. Each of the different candidate molecules are characterized by a spectral overlap score greater than or equal to a specified threshold value to determine which candidate molecules are further analyzed with regard to signal parameter similarity with the fragmentation spectrum.

The methods of the present invention can be performed on a relatively purified analyte (i.e., having less than 10% containments) or mixtures containing an analyte. In one embodiment, a sample having an analyte is fractionated or purified prior to ionization or measuring the fragmentation spectrum. As a non-limiting example, the sample containing the analyte is an elution product of a chromatographic separation technique, such as part of a GC-MS technique or a LC-MS technique.

The present methods are versatile and, thus, applicable to a wide range of mass spectrometry techniques including single and multiple stage mass spectrometry analysis. In an embodiment, the method further comprises generating the fragment ions using one or more ionization or dissociation methods. In an embodiment, for example, the one or more ionization or dissociation methods are selected from the group consisting of electron ionization (EI), chemical ionization (CI), electrospray ionization (ESI), atmospheric pressure chemical ionization (APCI), and matrix-assisted laser desorption ionization (MALDI). In an embodiment, for example, the one or more ionization/dissociation methods are selected from the group consisting of collision induced dissociation (CID), surface induced dissociation (SID), laser induced dissociation (LID), neutral reaction dissociation, ion reaction dissociation, electron capture dissociation (ECD), and electron transfer dissociation (ETD). In an embodiment, for example, the fragmentation spectrum is generated using a GC-MS method with electron ionization (EI) or a LC-MS method with electron ionization (EI).

In an embodiment, for example, the fragmentation spectrum is generated using a multistage mass spectrometry method (e.g., $MS^x$, wherein x is greater than 1). In an embodiment, for example, the fragmentation spectrum is generated using a tandem mass spectrometry method (e.g. MS/MS). In an embodiment, the fragmentation spectrum is generated using a quadropole mass spectrometer or an ion trap mass spectrometry method. In an embodiment, for example, a method of the invention further comprises the steps of measuring an intact mass value for a precursor ion derived from the analyte, and evaluating whether the candidate molecule has a mass within a preselected range (e.g. 20%, 10%, or 5%) of the intact mass value. This aspect of the invention is useful for further evaluating a candidate molecule on the basis of measured mass to charge ratio or molecular mass.

Additional steps are optionally performed to improve efficiency or identification rate. For example, in one embodiment, a sample containing the analyte is first fractionated using known separation techniques, such as liquid or gas chromatography. Analytes from the chromatography step are then collected and ionized. One or more deconvolution steps are optionally performed to isolate fragment ions from the same parent molecule together. One embodiment of the present invention provides a deconvolution step comprising:

1) performing two or more fragmentation scans of said analyte;

2) grouping together fragment peaks which have similar m/z values observed in consecutive EI fragmentation scans, thereby generating a data feature, wherein peaks which do not have similar m/z value observed in consecutive scans are grouped in separate data features; and 3) grouping together data features having peaks which elute within the same time period, thereby generating a set of fragment peaks originating from the analyte.

Another embodiment of the invention provides a method of identifying the composition of an analyte in a comprising:

(a) measuring a fragmentation spectrum for said analyte using a mass spectrometry technique providing a mass accuracy equal to or less than 75 ppm; wherein said fragmentation spectrum comprises a plurality of peaks corresponding to measured mass-to-charge ratios of fragment ions from said sample; wherein said fragmentation spectrum is characterized by a signal parameter corresponding to said peaks of said fragmentation spectrum;

(b) providing a plurality of different candidate molecules for analysis of said fragmentation spectrum of said analyte;

(c) independently determining putative fragment masses for possible fragment ions for each of said candidate molecules; and (d) comparing the putative fragment masses for each of said candidate molecules to the measured mass-to-charge ratios from said fragmentation spectrum, thereby independently determining, for each of the candidate molecules, signal parameter similarity of the fragmentation spectrum that match the putative fragment masses of said candidate molecule; and (e) using the signal parameter similarity of the fragmentation spectrum that match the putative fragment masses for each of said candidate molecules to identify the composition of said analyte. In an embodiment of this aspect, for example, the mass accuracy is equal to or less than 30 ppm and optionally for some embodiments equal to or less than 10 ppm.

In one aspect, the invention provides a method for improving spectral matching of fragmentation spectra collected on high-resolution GC-MS instruments against databases of reference spectra collected on unit-resolution GC-MS instruments. Several large databases of electron ionization (EI) spectra generated from pure compounds collected on unit-resolution instruments are currently available. It is known that pure EI spectra contain primarily fragment peaks stemming from a single parent molecule. Based on this principle, observed peaks in a fragmentation spectrum of a known compound can be explained systematically. By generating some, or optionally all, non-repeating combinations of atoms from a precursor molecular formula, a set of potential fragments is created. In some embodiments, every observed peak in a fragmentation spectrum of this compound can be annotated by matching its m/z value with the exact masses of these potential fragments. The fragmentation spectra can also be collected using LC-MS and compared against LC-MS databases of reference spectra using the same process.

In an aspect of the preset methods, an additional filtering step greatly improves the specificity of matches by using high-resolution accurate-mass (HRAM) mass spectrometry. By first assigning putative chemical identifications to each high-resolution spectrum, whether or not each peak can be explained by an accurate fragment mass stemming from the assigned formula can be determined. In certain instances, this method greatly increases the specificity of assigned identifications and improves confidence in unknown identifications.

In an aspect, the invention provides mass spectrometer for carrying out any of the methods described herein. In an embodiment, for example, the invention provides a mass spectrometer for analyzing an analyte in a sample, the mass spectrometer comprising: (i) an ion source for generating fragment ions from the sample; (ii) a mass analyzer for detecting fragment ions from the sample, thereby generating a fragmentation spectrum comprising a plurality of peaks corresponding to measured mass-to-charge ratios of fragment ions from the sample; wherein the fragmentation spectrum is characterized by a signal parameter corresponding to the peaks of the fragmentation spectrum; the mass analyzer providing a mass accuracy equal to or less than 75 ppm; and (iii) an processor for: a) determining putative fragment masses for possible fragment ions from a candidate molecule; and b) comparing the putative fragment masses of the candidate molecule to the measured mass-to-charge ratios from the fragmentation spectrum to determine a signal parameter similarity of the fragmentation spectrum that matches the putative fragment masses of the candidate molecule, thereby analyzing the analyte. In an embodiment of this aspect, for example, the mass accuracy is equal to or less than 30 ppm and optionally for some embodiments equal to or less than 10 ppm. In an embodiment of this aspect, putative fragment masses for all possible fragment ions from the candidate molecule are determined by the processor.

A wide range of ion sources are useful in the present devices including one or more electron ionization (EI) systems, chemical ionization (CI) systems, electrospray ionization (ESI) systems, atmospheric pressure chemical ionization (APCI) systems, and matrix-assisted laser desorption ionization (MALDI) systems. In some embodiments, the ion source provides ionization and/or fragmentation by one or more ionization or dissociation methods are selected from the group consisting of collision induced dissociation (CID), surface induced dissociation (SID), laser induced dissociation (LID), neutral reaction dissociation, ion reaction dissociation, electron capture dissociation (ECD), and electron transfer dissociation (ETD). In an embodiment, the device further comprises a separation component for purifying the sample having the analyte prior to measuring the fragmentation spectrum. In an embodiment, for example, the system is a GC-MS system with electron ionization (EI) or a LC-MS system with electron ionization (EI). In an embodiment, the mass analyzer is a quadropole mass analyzer or ion trap mass analyzer.

In an aspect, the present invention may be integrated with existing software-based solutions for mass spectrometry-based analysis and identification of proteins, small molecules, metabolites, and other analytes.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 2 illustrates different steps performed in matching high-resolution GC-MS spectra against spectra from unit-resolution reference libraries in one embodiment of the present invention. In this embodiment, the obtained EI spectrum undergoes deconvolution, spectral matching, followed by high-resolution filtering.

FIG. 7 shows an integer array representation of ethyne ($C_2H_2$) which is [2,2]. The first index represents the number of carbons in the molecule and the second the number of hydrogens (2 and 2, respectively). Starting with a base integer array of [0,0] each index is iteratively incremented so that all possible combinations of atoms are created which represents all possible fragments. These fragments and their integer array representation are displayed. The numerical indices in the upper-left hand corner of each box indicates the order in which each fragment is generated using an algorithm of the present invention. This same process can be applied to substantially larger molecules.

FIG. 10 shows two spectral matches returned from a database search of a known spectrum of molinate (molinate and 2-methyl-1,3-cyclohexanedione, respectively). The experimentally derived spectrum is shown on top, and the corresponding reference spectra are shown on the bottom. High scores are returned in both instances with all prominent features matching in both spectra. Using the algorithm in one embodiment of the present invention, it was found that 99.63% of the observed TIC signal can be explained using the chemical formula of molinate ($C_9H_{17}NOS$) but only 19.30% of the observed signal using the chemical formula of 2-Methyl-1,3-cyclohexanedione ($C_7H_{10}O_2$). The peaks which were successfully matched with an exact mass fragment (within an allowed 15 ppm tolerance) from the specified formula are displayed.

FIG. 14 shows the top five spectral matches returned from a database search of malonate was derivatized with a tert-butyldimethylsilyl label (Bis (TBDMS) malonate) and the experimentally derived spectrum searched against the NIST12 unit resolution EI reference library. The top five best unit-resolution scoring spectral matches were returned with scores ranging from 66.610 (2-methyl-1,4-butanediol, bis (TBDMS) ether) to 60.773 (Bis (TBDMS) malonate). Using the high-resolution filtering algorithm, the chemical formula of Bis (TBDMS) malonate explained a larger percentage (99.719%) of the observed TIC in the spectrum than any of the other compounds. Prominent features which appear in one or more of the spectra are annotated with the corresponding chemical formula.

FIG. 16 highlights the plot point corresponding to etridiazole ($C_5H_5Cl_3N_2OS$). FIG. 17 highlights the plot points corresponding to supersets of $C_5H_5Cl_3N_2OS$, and FIG. 18 highlights the plot points corresponding to subsets of $C_5H_5Cl_3N_2OS$.

FIG. 21A: Peaks observed across consecutive scans are condensed into data features. Shown here are all features observed within a narrow time window of a standard GC gradient. FIG. 21B: Features are smoothed and grouped based on elution apex. The observed features are placed into four logical groups based on position of their chromatographic apex. All features within a group are assumed to arise from a singular precursor. FIG. 21C: Individual spectra are derived from feature groups based on average m/z and apex intensity and can then be submitted for spectral matching. FIG. 21D: A strong spectral match of an experimentally-derived spectrum of loratadine against the corresponding NIST reference spectrum. All subformulas from $C_{22}H_{23}ClN_2O_2$ are generated and sorted by exact formula mass less an electron. A variant containing a $^{37}Cl$ is generated for all fragments containing a $^{35}Cl$. FIG. 21E: Subformulas are matched to peaks in ascending order based on mass. For each matched fragment a variant containing appropriate heavy isotopes is created and placed into the list of subformulas in sorted-order. FIG. 21F: For the high-res spectrum of loratadine 99.2617% of the measured ion current can be annotated with a subformula of $C_{22}H_{23}ClN_2O_2$.

FIG. 22A: Spectral match and HRF score results are shown for the 105 spectra in the dataset. Each plotted point represents a correct assignment. HRF scores cluster together near the high end of the range while spectral match scores are more disperse. FIG. 22B: HRF scores for a spectrum of beta-sitosterol (TMS) using a60,560 different formulas are shown. The true parent ($C_{32}H_{58}OSi$) is shown in red. Sub- and supersets of $C_{32}H_{58}OSi$ are shown in green and blue respectively. No subformula is able to achieve a HRF score as high as the true parent indicating that these compounds lack the appropriate atomic composition to successfully annotate all observed signal. We would expect similar behavior from other spectra where an intact molecular ion is present. As anticipated, all supersets produce similarly high HRF scores. FIG. 22C: Cumulative distributions from the comparison of 60,560 unique formulas to all 105 spectra are shown in gray. A representative distribution found by combining all results is shown in blue. We find on average that only 3.206% of formulas can successfully achieve the median HRF score (99.700) from the data set.

FIG. 23A: GC-MS TIC chromatograms from the most concentrated (blue) and least concentrated (red) spiked samples are shown. At high concentration, intense chromatographic peaks are observed for all spiked drugs. These features largely disappear at low concentration. FIG. 23B: Deconvolved feature groups for the drug Glutethimide at high (blue) and low (red) concentrations. Background features are shown in gray. Presence of complex background matrix makes grouping more challenging due to the preponderance of observed signal. FIG. 23C: Spectral match and HRF scores for each drug analyzed at all concentrations where analyte abundance was sufficient to produce a spectrum. A minimum of six concentration data points are reported for each drug. Spectral match score begins to decline with reduced concentration; however, the HTF metric remains high throughout. FIG. 23D: Two spectra were isolated for each drug (one at the most concentrated point, the other at the least) and an HRF score was calculated for each using 55,229 unique formulas (0-500 Da) from the NIST database. Cumulative HRF results are shown for both the high (blue) and low (red) concentration along with a combined distribution for both populations. The curves indicate that the specificity of the HRF approach does not vary appreciably with a reduction in peak count.

FIGS. 24A-24I show individual analyses of drugs spiked into human urine at variable concentration. Shown here are the measured spectral match and HRF scores for all deconvolved spectra extracted from the urine spike-in data set. These data are the same as that shown in FIG. 23B. Corresponding spectral match and HRF score lines are plotted together for clarity. It is noted that at reduced concentrations observed spectral match score tends to decline while the HRF metric remains relatively high.

FIGS. 27A-27B show spectral matching/high-res filtering results from a human urine sample spiked with drug standards. The analysis of a human urine sample spiked with a number of drugs (10 ng/μL) yielded 272 spectra containing 10+ peaks. FIG. 27A: The 10 best spectral matches (left to right) for all 272 spectra (top to bottom) are shown in the green heat map. The intensity of each pixel reflects spectral similarity. The corresponding HRF score for all matches is shown in the blue heat map. Similarly, the intensity here reflects the percentage of ion current that can be annotated with an exact chemical formula. The selected ranges for spectral match and HRF score (40-100 and 90-100) were selected based on results from known standards reported in this study. We observed no instances where an HRF score less than 90 corresponded to a correct identification. In this regard the HRF metric is essentially a binary classifier up to this point. FIG. 27B: The distribution of all HRF scores above, and below 90 (blue and gray, respectively). We find that from all 2,720 returned spectral matches 72.2428% had an associated HRF score less than 90. This dimension of information can be used to discriminate against putative Identifications.

FIG. 29 (Supplementary Table 1) provides results from all analyzed reference compounds complete with raw file name, retention time, HRF score, spectral match score, peak count, and the reference spectrum name as reported.

FIG. 30 (Supplementary Table 2) illustrates the Global HRF analysis. Shown here is a summary of the returned HRF results when calculating scores for the 105 dataset spectra against 60,560 unique chemical formulas. Compounds are ranked by ascending monoisotopic mass. The raw number of formulas which produce a HRF score less than, or greater than or equal to the true parent are shown in columns labeled HRF<Parent Score and HRF>=Parent Score. Using the pool of formulas which yielded a HRF Score>=the true parent HRF score the number of true and false supersets were determined. A superset is a formula where all of the atoms in the true parent set are also contained. Non-supersets were those formulas which failed to meet this condition. For those non-supersets the average percentage of atoms shared with the true parent was calculated, along with the average and median number of additional atoms held by the formula in question. We find that these non-supersets which can achieve similarly high HRF scores as the true parent often share a large percentage of atoms with the correct precursor (93.574%) and contain a substantial number of additional atoms on average (19.506)

FIG. 31 (Supplementary Table 3) provides the associated spectral match score, HRF score, and peak count for all extracted spectra in the drug spike-in dataset. All spectra considered contained at least 10 peaks.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

Definitions

As used herein, "mass accuracy" is the ability of a mass spectrometer to accurately determine the mass-to-charge ratios of ions being measured, and is typically defined as the ratio of the mass-to-charge ratio (m/z) measurement error to the true mass-to-charge ratio (m/z). Commercial instrument manufacturers typically specify mass accuracy as relative errors in units of percentage (%) or parts-per-million (ppm). For example, the PPM error for a peak of given m/z may be calculated using the following relationship:

PPM Error=(Measured M/Z−Theoretical M/Z)/(Theoretical M/Z)*1×10$^6$.

Figure 28A:
FIG. 28A displays the top 8 spectral matches (based on a weighted dot product) to Cyanazine.
Figure 28B:
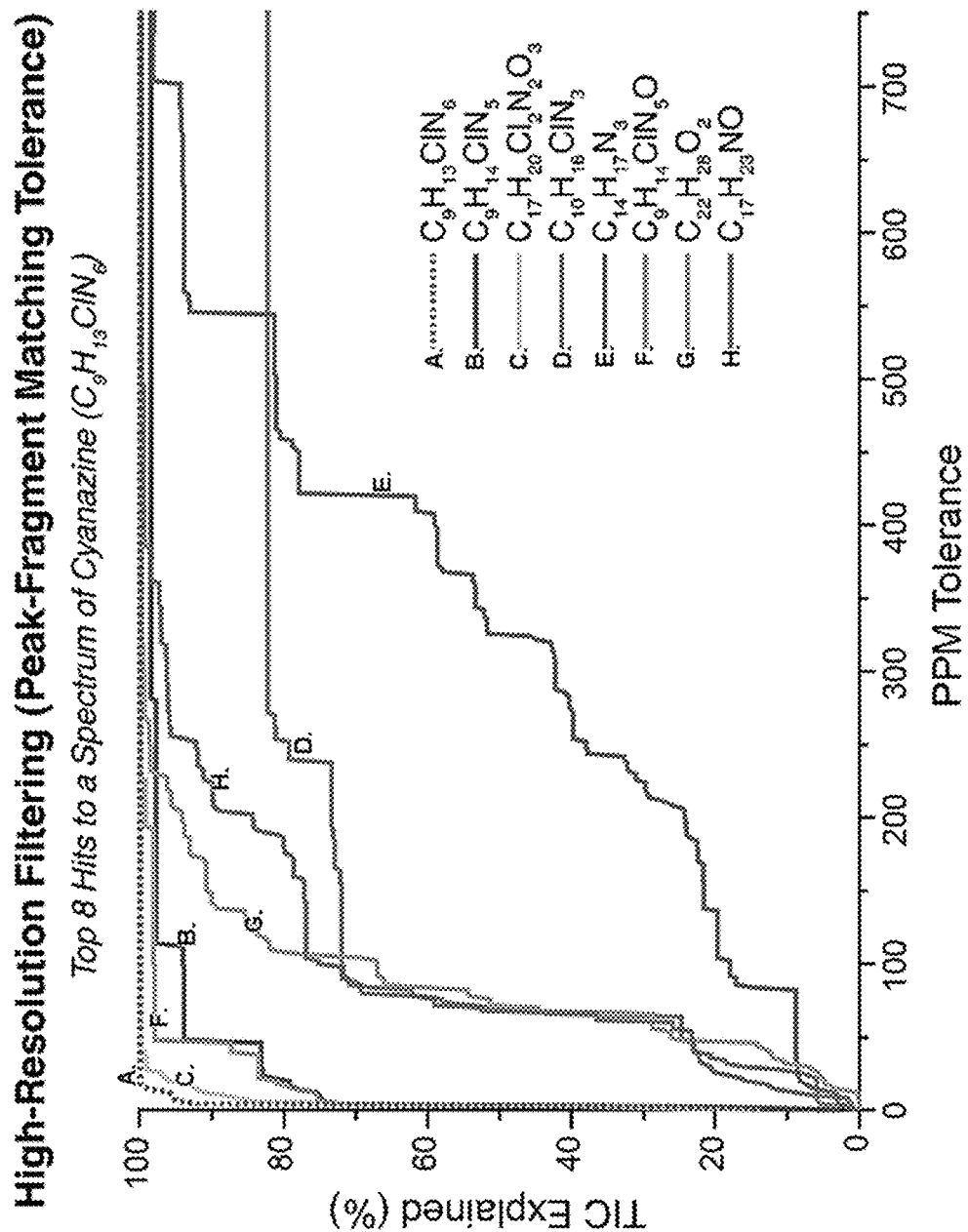
FIG. 28B shows the results of calculation of the percent TIC explained (HRF score) using a range of tolerances (PPM tolerances 0 to 750).

In some embodiments, the mass accuracy of the measurement and specificity of the high-resolution filtering are inversely proportional. This concept is illustrated in FIGS. 28A and 28B. FIG. 28A displays the top 8 spectral matches (based on a weighted dot product) to Cyanazine. The Collected Cyanazine spectra is in red (above the X-axis), the inverted blue traces (below the X-axis) are from the NIST library. For each of the 8 spectra, the percent TIC explained (HRF score) was calculated using a wide range of tolerances (PPM tolerances 0 to 750). The results of this calculation are shown in FIG. 28B. The goal is to have a small number, or optionally only one compound (chemical formula, preferably the current one), which will yield 100% TIC explained. When a PPM tolerance of 30 or less is used during the peak matching, we find that to be the case. By 75 PPM there are 2 compounds which provide 100% TIC explained, by 300 PPM there are 4. The wider mass tolerance used the less specific the HRF score. Nonetheless it still has value in narrowing the pool of candidates, which has substantial utility. This example is for a single compound. In some circumstances, the exact PPM requirement which provides the best selectivity may be compound specific. However, use of 30 PPM mass tolerance or less we get substantial selectivity for many compounds.

"Dot product calculation" refers to any mathematical calculation which measures the similarity between two GC-MS EI spectra and produces as a result some numerical value which is reflective of the similarity between the two.

"Ionization" refers to the formation of ions as a result of a chemical reaction, high temperature, electrical discharge, particle collision or radiation. Methods of ionizing a molecule to generate precursor ions for analysis using mass spectrometry include, but are not limited to, electron ionization (EI), chemical ionization (CI), electrospray ionization (ESI), atmospheric pressure chemical ionization (APCI), and matrix-assisted laser desorption ionization (MALDI). Such precursor ions can then be further fragmented and analyzed using tandem MS.

Many of the molecules discussed herein contain one or more ionizable groups. "Ionizable groups" include groups from which a proton can be removed (e.g., —COOH) or added (e.g., amines) and groups which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

"Parent molecule" refers to a single molecule or analyte which produces one or more ions during mass spectrometry. As used herein, the term "precursor ion" is used herein to refer to an ion which is produced during ionization stage of mass spectrometry analysis, including the $MS^1$ ionization stage of MS/MS analysis.

As used herein, the terms "product ion" and "secondary ion" are used interchangeably and refer to an ion which is produced during ionization and/or fragmentation process(es) during mass spectrometry analysis, including the $MS^2$ ionization stage of MS/MS analysis. The term "secondary product ion" as used herein refers to an ion which is the product of successive fragmentations.

As used herein, the term "fragmentation spectrum" refers to a mass spectrum consisting of analyte ions, fragment ions, precursor ions and/or product ions as generated during ionization, or a tandem mass spectrum resulting from dissociation of a selected precursor.

As used herein, the term "analyzing" refers to a process for determining a property of an analyte. Analyzing can determine, for example, physical properties of analytes, such as mass, mass to charge ratio, concentration, absolute abundance, relative abundance, or atomic or substituent composition. In the context of proteomic analysis, the term analyzing can refer to determining the composition (e.g., sequence) and/or abundance of a protein or peptide in a sample.

As used herein, the term "analyte" refers to a compound, mixture of compounds or other composition which is the subject of an analysis. Analytes include, but are not limited to, biomolecules, proteins, modified proteins, peptides, modified peptides, small molecules, pharmaceutical compounds, oligonucleotides, sugars, polymers, metabolites, hormones, lipids, and mixtures thereof.

As used herein, the term "mass spectrometry" (MS) refers to an analytical technique for the determination of the elemental composition, mass to charge ratio, absolute abundance and/or relative abundance of an analyte. Mass spectrometric techniques are useful for identifying the composition and/or abundance of analytes, such as biomolecules, proteins, modified proteins, peptides, modified peptides, small molecules, pharmaceutical compounds, oligonucleotides, sugars, polymers, metabolites, hormones, lipids, other chemical compounds and mixtures thereof. Mass spectrometry includes processes comprising ionizing analytes to generate charged species or species fragments, fragmentation of charged species or species fragments, such as product ions, and measurement of mass-to-charge ratios of charged species or species fragments, optionally including additional processes of isolation on the basis of mass to charge ratio, additional fragmentation processing, charge transfer processes, etc. Conducting a mass spectrometric analysis of an analyte results in the generation of mass spectrometry data for example, comprising the mass-to-charge ratios and corresponding intensity data for the analyte and/or analyte fragments. Mass spectrometry data corresponding to analyte ion and analyte ion fragments is commonly provided as intensities of as a function of mass-to-charge (m/z) units representing the mass-to-charge ratios of the analyte ions and/or analyte ion fragments. Mass spectrometry commonly allows intensities corresponding to difference analytes to be resolved in terms of different mass to charge ratios. In tandem mass spectrometry (MS/MS or MS$^2$), multiple sequences of mass spectrometry analysis are performed. For example, samples containing a mixture of chemical compounds, such as biomolecules, can be ionized and the resulting precursor ions separated according to their mass-to-charge ratio. Selected precursor ions can then be fragmented and further analyzed according to the mass-to-charge ratio of the fragments.

As used herein, the term "interference" refers to a species detected in an analysis which interferes with the detection of a species or analyte of interest. For example, interference can refer to detection of a biomolecule, small molecule pharmaceutical, protein, or protein fragment, which is not a biomolecule, small molecule pharmaceutical, protein, or protein fragment of interest and which interferes with the accurate detection or quantitation of the biomolecule, small molecule pharmaceutical, protein, or protein fragment of interest. Interference can be quantified as an interference ratio, such as a ratio of an amount of interference signal to an amount of analyte signal. In a mass spectral analysis, interference can be manifested as an interference peak which corresponds to detection of a species which is not an analyte of interest.

As described herein, "isolation" or an "isolation window" refers to a range of ions, such as precursor ions that is selectively separated and fragmented, manipulated or isolated.

As used herein, the term "species" refers to a particular molecule, compound, ion, anion, atom, electron or proton. Species include isotopically labeled analytes, isotopic tagging reagents, isotopically labeled amino acids and/or isotopically labeled peptide or proteins.

As used herein, the term "signal-to-noise ratio" refers to a measure which quantifies how much a signal has been corrupted by noise, or unwanted signal. It can also refer to the ratio of signal power to the noise power corrupting the signal. A ratio higher than 1:1 indicates more signal than noise and is desirable for some applications.

As used herein, the term "mass-to-charge ratio" refers to the ratio of the mass of a species to the charge state of a species. The term "m/z unit" refers to a measure of the mass to charge ratio. The Thomson unit (abbreviated as Th) is an example of an m/z unit and is defined as the absolute value of the ratio of the mass of an ion (in Daltons) to the charge of the ion (with respect to the elemental charge).

As used herein, the term "mass spectrometer" refers to a device which generates ions from a sample, separates the ions according to mass to charge ratio, and detects ions, such as product ions derived from isotopically labeled analytes, isotopic tagging reagents, isotopically labeled amino acids and/or isotopically labeled peptide or proteins. Mass spectrometers include single stage and multistage mass spectrometers. Multistage mass spectrometers include tandem mass spectrometers which fragment the mass-separated ions and separate the product ions by mass once.

"Mass spectrometer resolving power, often termed resolution, is a quantitative measure of how well m/z peaks in a mass spectrum are separated (i.e., resolved).

As used herein, the term "ion source" refers to a device component which produces ions from a sample, for example, during mass spectrometry analysis. Examples of ion sources useful in the present methods include, but are not limited to, electrospray ionization sources and matrix assisted laser desorption/ionization (MALDI) sources.

As used herein, the term "controller" refers to a device component which can be programmed to control a device or system, as is well known in the art. Controllers can, for example, be programmed to control mass spectrometer systems so as to carry out the methods as described herein. The invention includes mass spectrometers having a controller configured to carry out any of the methods described herein.

As used herein, the term "ion optic" refers to a device component which assists in the transport and manipulation of charged particles, for example, by the application of electric and/or magnetic fields. The electric or magnetic field can be static, alternating, or can contain both static and alternating components. Ion optical device components include, but are not limited to, ion deflectors which deflect ions, ion lenses which focus ions, and multipoles (such as quadruples) which confine ions to a specific space or trajectory. Ion optics include multipole RF device components which comprise multiple rods having both static and alternating electric and/or magnetic fields.

As used herein, the term "fractionated" or "fractionate" refers to the physical separation of a sample, as is well known in the art. A sample can be fractionated according to physical properties such as mass, length, or affinity for another compound, among others using chromatographic techniques as are well known in the art.

Fractionation can occur in a separation stage which acts to fractionate a sample of interest by one or more physical properties, as are well known in the art. Separation stages can employ, among other techniques, liquid and gas chromatographic techniques. Separation stages include, but are not limited to, liquid chromatography separation systems, gas chromatography separation systems, affinity chromatography separation systems, and capillary electrophoresis separation systems.

The terms "peptide" and "polypeptide" are used synonymously in the present description, and refer to a class of compounds composed of amino acid residues chemically bonded together by amide bonds (or peptide bonds). Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, phosphorylation, glycosylation, lipidation, prenylation, sulfonation, hydroxylation, acetylation, methylation, methionine oxidation, alkylation, acylation, carbamylation, iodination and the addition of cofactors. Peptides include proteins and further include compositions generated by degradation of proteins, for example by proteolyic digestion. Peptides and polypeptides can be generated by substantially complete digestion or by partial digestion of proteins. Polypeptides include, for example, polypeptides comprising 2 to 100 amino acid units, optionally for some embodiments 2 to 50 amino acid units and, optionally for some embodiments 2 to 20 amino acid units and, optionally for some embodiments 2 to 10 amino acid units.

"Fragment" refers to a portion of a molecule. Fragments may be singly or multiple charged ions. As used herein, the term "fragment ions" refers to a portion of a parent or precursor molecule that exists in an ionized form, such as formed during MS analysis and MS/MS analysis. Fragments may be derived from bond cleavage in a parent molecule, such as site specific cleavage of polypeptide bonds in a parent peptide. Fragments may also be generated from multiple cleavage events or steps. Fragments may be a truncated peptide, either carboxy-terminal, amino-terminal or both, of a parent peptide. A fragment may refer to products generated upon the cleavage of a polypeptide bond, a C—C bond, a C—N bond, a C—O bond or combination of these processes. Fragments may refer to products formed by processes whereby one or more side chains of amino acids are removed, or a modification is removed, or any combination of these processes. Fragments may include fragments formed under metastable conditions or result from the introduction of energy to the analyte or a precursor ion by a variety of dissociation and ionization methods including, but not limited to, collision induced dissociation (CID), surface induced dissociation (SID), laser induced dissociation (LID), electron capture dissociation (ECD), electron transfer dissociation (ETD), electron ionization (EI), chemical ionization (CI), electrospray ionization (ESI), neutral reaction dissociation, ion reaction dissociation, atmospheric pressure chemical ionization (APCI), and matrix-assisted laser desorption ionization (MALDI), or any combination of these methods or any equivalents known in the art of tandem mass spectrometry. Properties of fragments, such as molecular mass, may be characterized by analysis of a fragmentation mass spectrum.

Overview:

Gas chromatography-mass spectrometry (GC-MS) has been used for qualitative and quantitative small molecule analysis since its utility as an analytical technique was first demonstrated in the late 1960's. Since then there have been a number of incredible advances in mass spectrometry with regard to improved resolution, sensitivity, and speed of data collection. The introduction of Orbitrap mass analyzers is one such notable instance. The Orbitrap can achieve resolving powers of nearly 1,000,000, which was previously possible only on costly Fourier transform ion cyclotron resonance mass spectrometers (FTICR-MS). Despite the notable improvements that have been made in the ability to quickly acquire high-resolution spectra with sub-ppm level mass accuracy, very little has changed in the realm of GC-MS. Frequently, small molecule analysis is still carried out on unit-resolution mass spectrometers similar to what was used in GC-MS work 50 years ago. Sufficed to say, the extraordinary benefits of high-resolution mass spectra have yet to be applied to this field.

For example, in a typical GC-MS experiment small molecules are fractionated or separated on a front-end GC and then ionized using either chemical (CI) or electron ionization (EI) prior to MS analysis. CI enables measurement of intact precursor mass, while EI causes molecules to fragment in characteristic patterns. These fragmentation patterns are highly reproducible and useful for analyte identification. To assign identifications, user-generated spectra are extracted from raw data files and matched against databases of previously collected reference spectra. This method is fairly robust, but the lack of high-resolution data in these cases prevents the discrimination of candidate precursors on the basis of accurate mass. There are also many cases where dissimilar compounds generate similar fragmentation spectra, which can lead to an inordinately high number of false identifications, again, due to lack of high-resolution capabilities. Furthermore, the degree of overlap between observed and reference spectra, needed to qualify an identification as correct or incorrect, is ambiguous and subject to human judgment.

Figure 1:
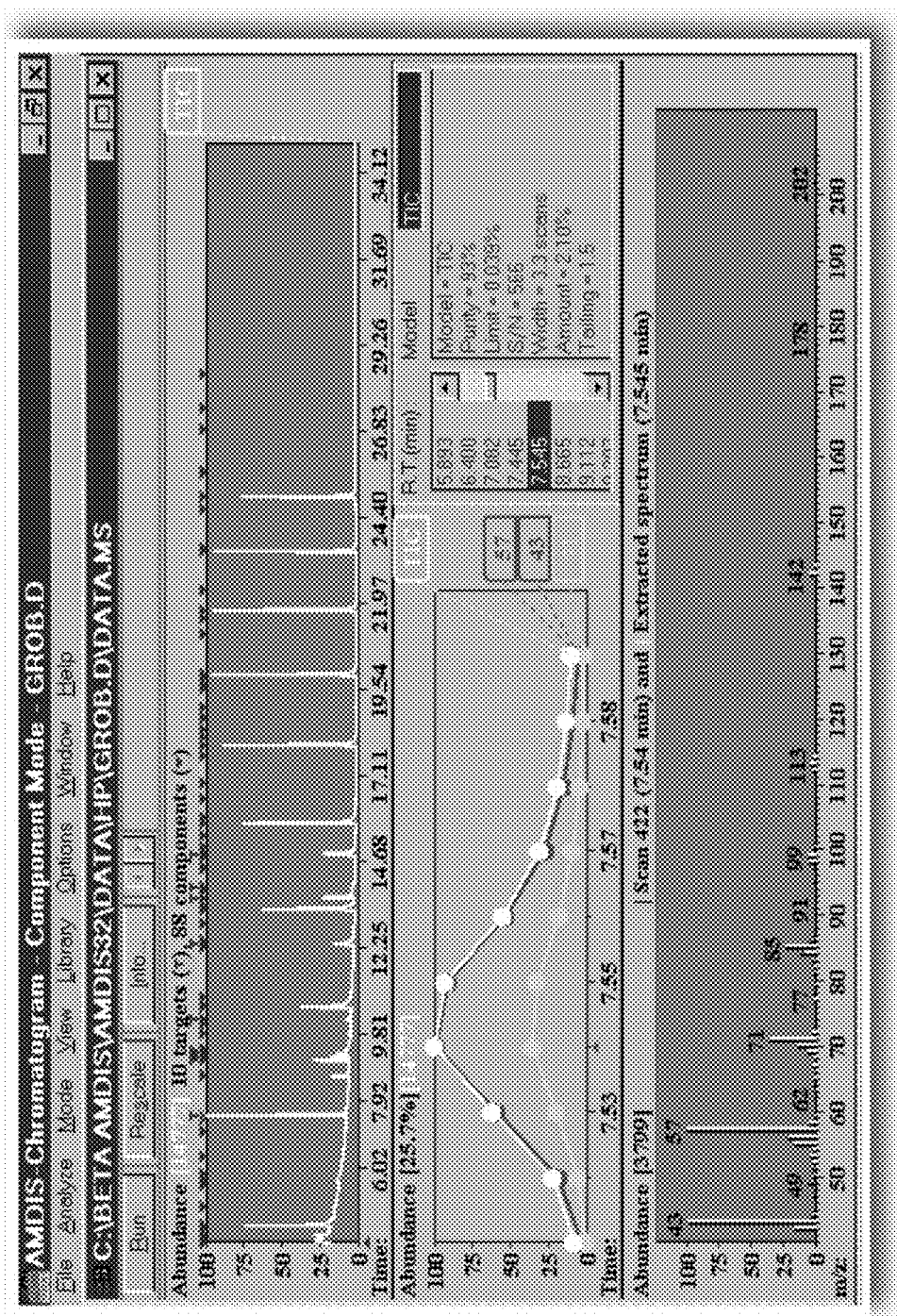
FIG. 1 shows a typical screen shot of the currently available Automated Mass Spectral Deconvolution and Identification System (AMDIS) computer program that extracts spectra for individual components in a MS data file and attempts to identify potential target compounds by matching these spectra against a reference library.

Ideally, it would be possible to compare collected mass spectral data to pre-existing high-resolution reference libraries in order to assign identifications. However, this is not a possibility given the amount of time and resources that were needed to compile reference libraries currently in existence. Additionally, the NIST and Wiley reference libraries contain pure EI spectra for hundreds of thousands of compounds and can still be of great use (FIG. 1).

As described herein, one aspect of the present invention provides methods and algorithms allowing high-resolution mass spectra of a sample to be accurately identified using pre-existing reference libraries, including unit-resolution databases. These high-resolution mass spectra can be matched to unit-resolution databases, such as by rounding peak m/z values to the nearest whole integer. The returned spectral matches can still be ambiguous but additional filtering can now be employed to increase identification rate. For example, the top N matched compounds can be stored, and for each putative identification all non-repeating combinations of atoms are generated from its molecular formula. This set of combinations represents a set of possible chemical fragments. After generating each set of fragments, and filtering away impossible formulas, these chemical fragments are matched against the high-resolution spectrum at high mass accuracy (such as $\leq 75$ ppm, $\leq 30$ ppm, $\leq 20$ ppm or $\leq 10$ ppm). From here, it is determined what percentage of the spectrum can be explained by each set of chemical fragments. Optionally, the sample is fractionated using a separation technique, such as liquid and gas chromatography, prior to the high-resolution mass spectra being collected.

Alternatively, the present invention also provides methods and algorithms allowing high-resolution mass spectra of a sample to be compared to the spectra of one or more candidate molecules, or to known chemical formulas, which may not necessarily be part of a reference library.

The invention is further detailed in the following Examples, which are offered by way of illustration and are not intended to limit the scope of the invention in any manner.

Example 1: High Mass Accuracy Filtering for Improved Spectral Matching of High-Resolution Gas Chromatography-Mass Spectrometry Data Against Unit-Resolution Reference Databases The algorithm and methods described herein presume that every fragment in a pure mass spectrum stems from the same parent molecule. Based on this concept, it can be concluded that every fragment observed in said spectrum is made up of some combination of atoms from the parent molecule. Therefore, if an accurate mass spectrum of a compound is collected, every high-res peak should be able to be annotated with an exact chemical formula containing some subset of atoms contained in the parent molecular formula. Using this idea, candidate identifications can first be assigned to high-resolution spectra of pure compounds based on similarity to low-resolution reference spectra. Having a candidate molecular formula then allows the user to attempt to explain every observed high-res peak with some fragment containing only the atoms which are present in the parent formula. Theoretically, if a correct match is present, every peak (or almost every peak) should be able to be explained and the parent molecule identified.

In one embodiment illustrated in FIG. 2, the method includes a deconvolution step used in conjunction with a spectral matching step and a high-resolution filtering step. After GC separation, a sample is ionized and high-resolution mass spectra are obtained. The deconvolution step groups raw mass spectra data into related features so that spectra containing only peaks from the same parent molecule are grouped together. A unit-resolution copy of each EI spectrum is created and matched against a unit-resolution database. A scoring system, such as a dot product scoring system, is calculated for each spectral comparison and the top spectral matches are stored. For each stored spectral match, all non-repeating combinations of atoms are generated for each candidate parent molecule associated with the matched spectra, and the exact mass fragments of the potential atom combinations are matched to the obtained high-resolution spectra. The amount of the high-resolution spectra explained by the mass fragments of the potential atom combinations is then calculated and provided.

Algorithm Design

The following description of the high-resolution spectral matching algorithm includes all steps which are necessary to take raw data collected on a HRAM GC-MS system and produce confident identifications. Note that all high-resolution data collected to this point has been on a novel GC-Orbitrap built by the Coon Research Group (University of Wisconsin-Madison).

Figure 3A:
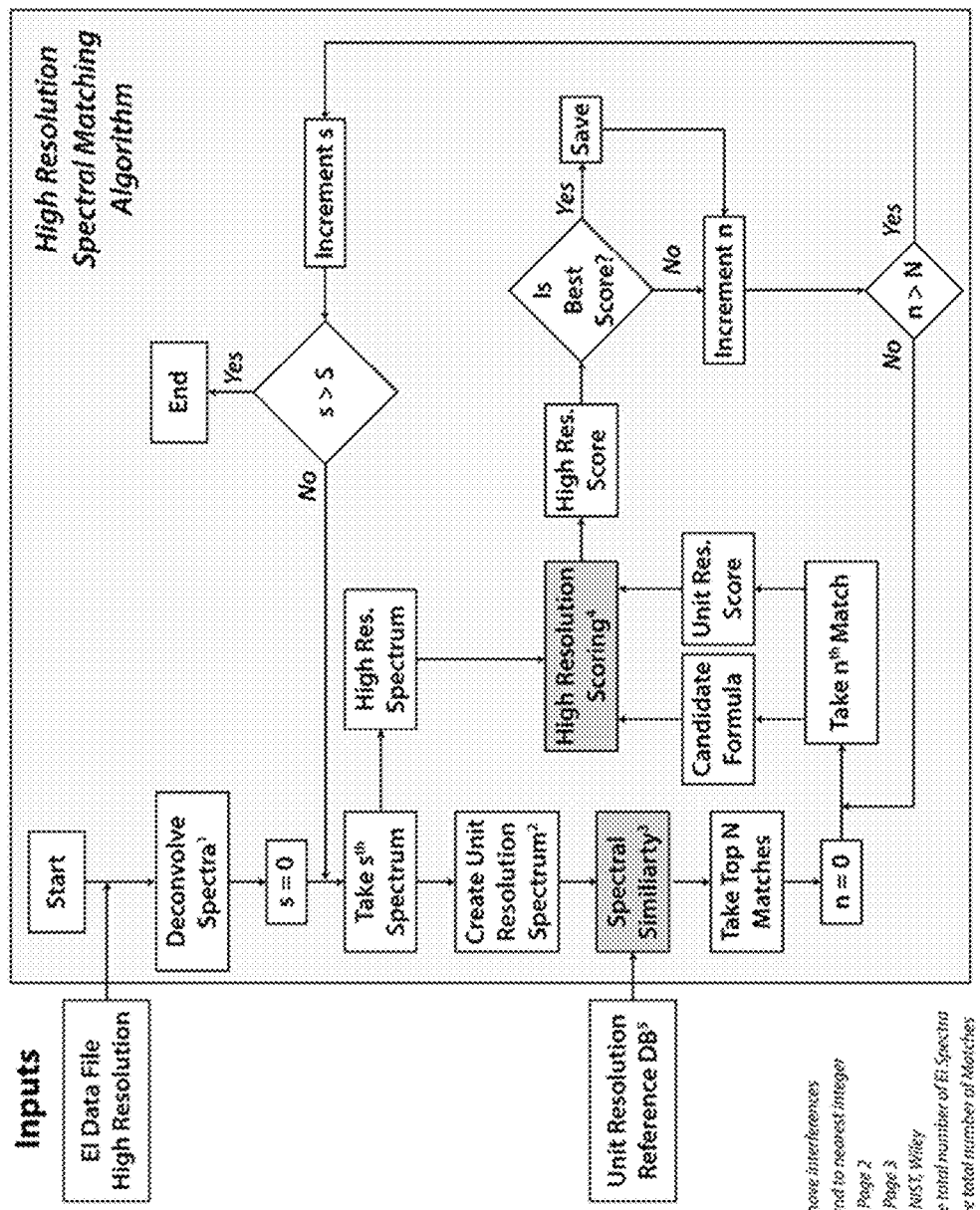
FIGS. 3A, 3B and 3C show a standard workflow for a high-resolution spectral matching algorithm in one embodiment of the invention, including the high-resolution spectral matching algorithm (FIG. 3A), spectral similarity algorithm (FIG. 3B), and high-resolution scoring algorithm (FIG. 3C). Steps from data collection and processing through identification of unknown molecules are shown in this embodiment.
Figure 3B:
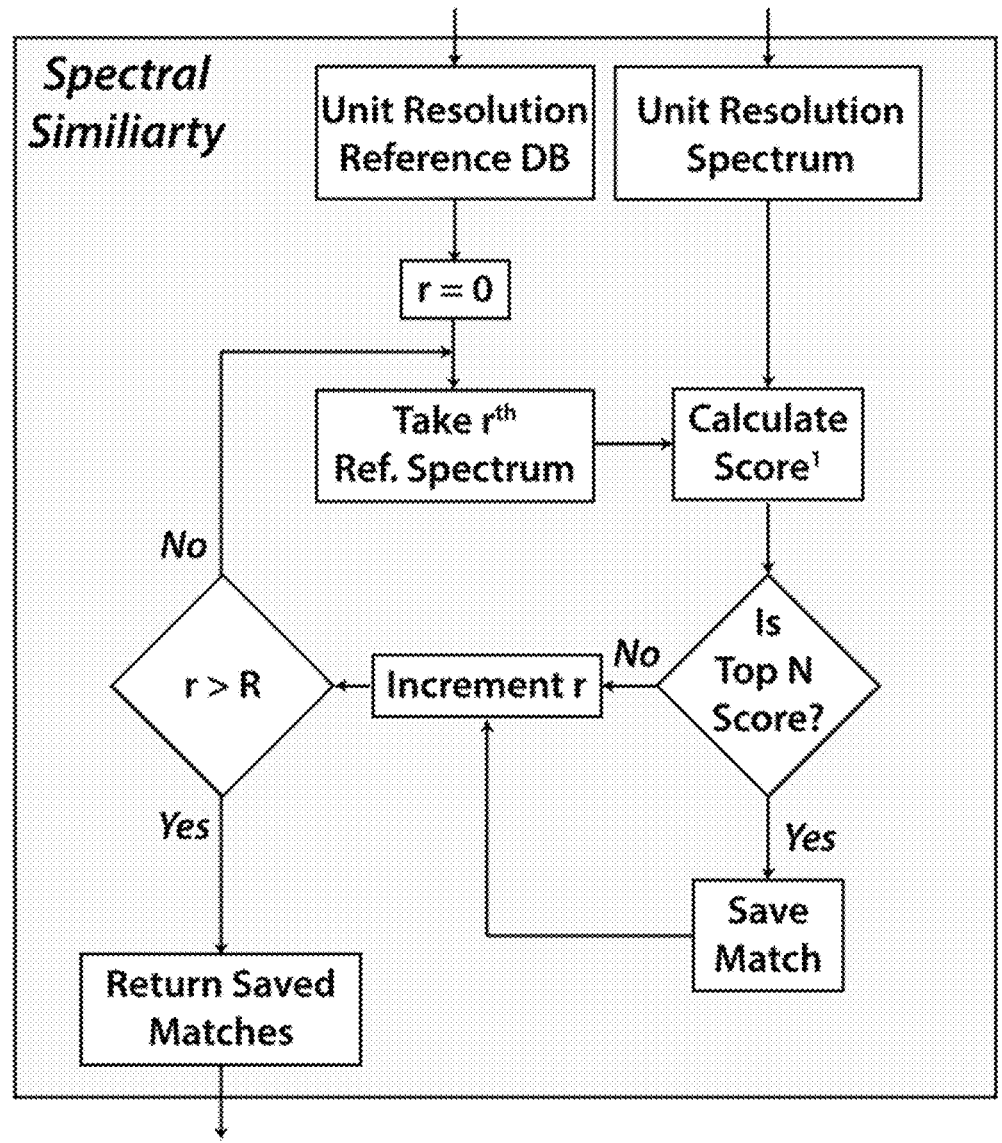
Figure 3C:
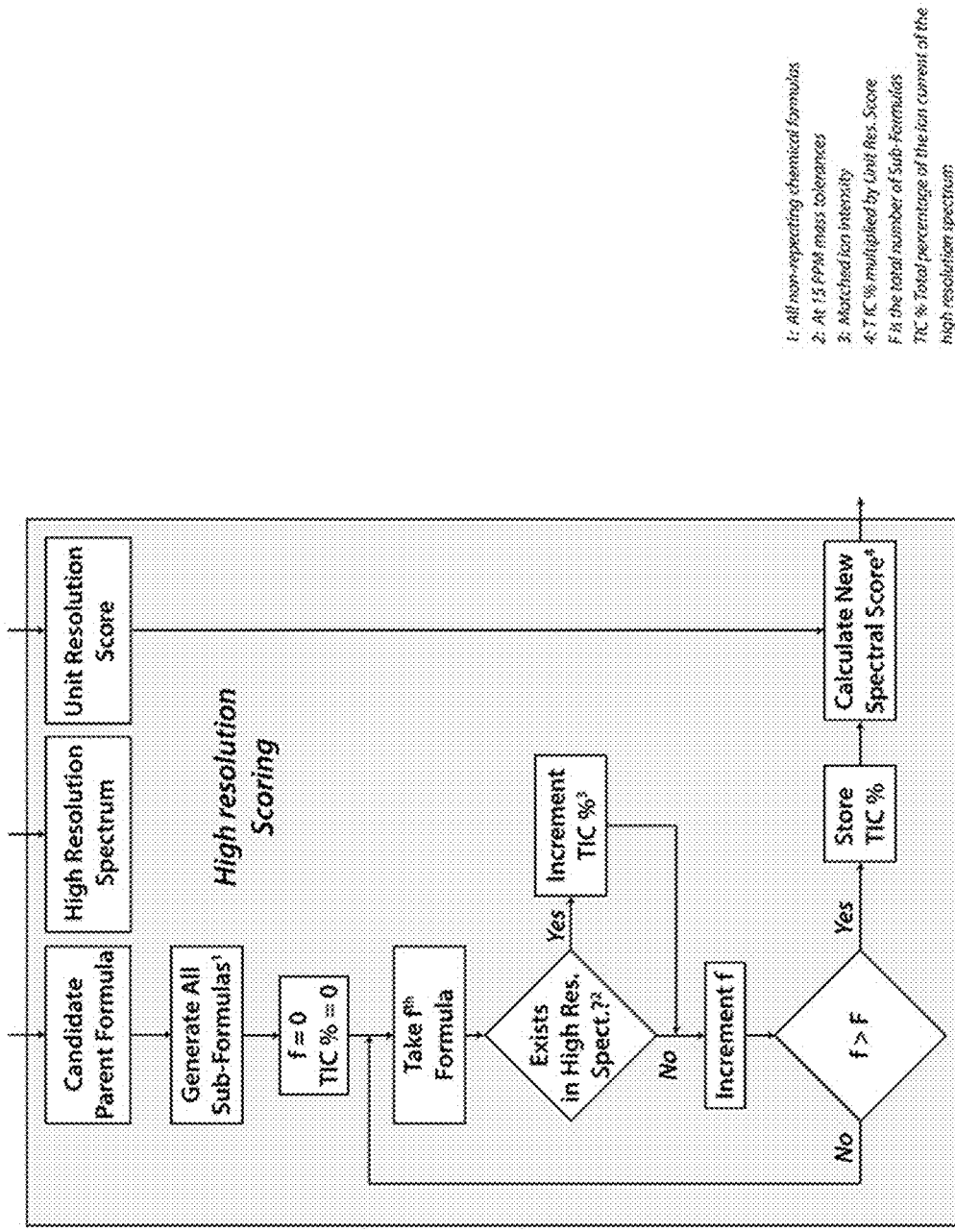

The standard workflow for assigning a putative identification to a compound analyzed using GC-MS is to collect a pure fragmentation spectrum generated using electron impact ionization and then compare that against a database of reference EI spectra. The algorithm described here greatly improves upon this standard workflow. The measured data is simultaneously utilized and leveraged with the high mass accuracy provided by high-resolution mass spectrometers (which is nearly impossible to replicate in silico). As mentioned above, the three parts of the algorithm which will be discussed in detail are Deconvolution, Spectral Matching, and High-Resolution Filtering, with the high-resolution filtering step being the most novel and powerful step. The standard workflow for processing data using the algorithm is shown in FIGS. 3A-3C.

Deconvolution

In the analysis of complex mixtures of volatile compounds front end gas chromatographic separation is critical. Although GC is both very robust and reproducible it can often fail to separate individual compounds from one another, particularly in the presence of a background matrix. Given that all reference spectra have been collected using pure compounds (which are mostly free of contaminants), it is important to compare spectra containing only fragments from a given parent molecule. Because of this requirement back-end, deconvolution to extract "pure" spectra is often necessary. One of the principle challenges in spectral deconvolution of a complex mixture is to pull out all compounds in the sample without missing anything. This is challenging as it is not always obvious when something eluted during a gradient, notably in the case of lowly abundant species. The deconvolution algorithm was written such that every peak in every spectrum collected during a GC-MS run is considered and no compounds will be missed.

The first step of the algorithm combines all peaks in a raw data file into features. A feature is an object comprised of peaks which have the same m/z value that are observed in consecutive scans. The algorithm takes all peaks present in the first scan of the run and checks to see if there is a corresponding peak in the second scan (a small mass tolerance of ~20 ppm is allowed). If a peak is observed in both scans it is assumed that are in fact the same species and then they are grouped into a feature. The next scan is then checked for the same peak, and then the next, continually adding each peak found to the feature while it is present. Once a scan is found where the peak is not present, the feature is considered to be "complete" and it is moved to a new list. This process is repeated for every scan in the raw file. The algorithm was written in a way that the check for each peak in subsequent scans is extremely quick. This speed component is critical as one of the overarching goals for the algorithm is that it executes very quickly to facilitate rapid data analysis.

Figure 4:
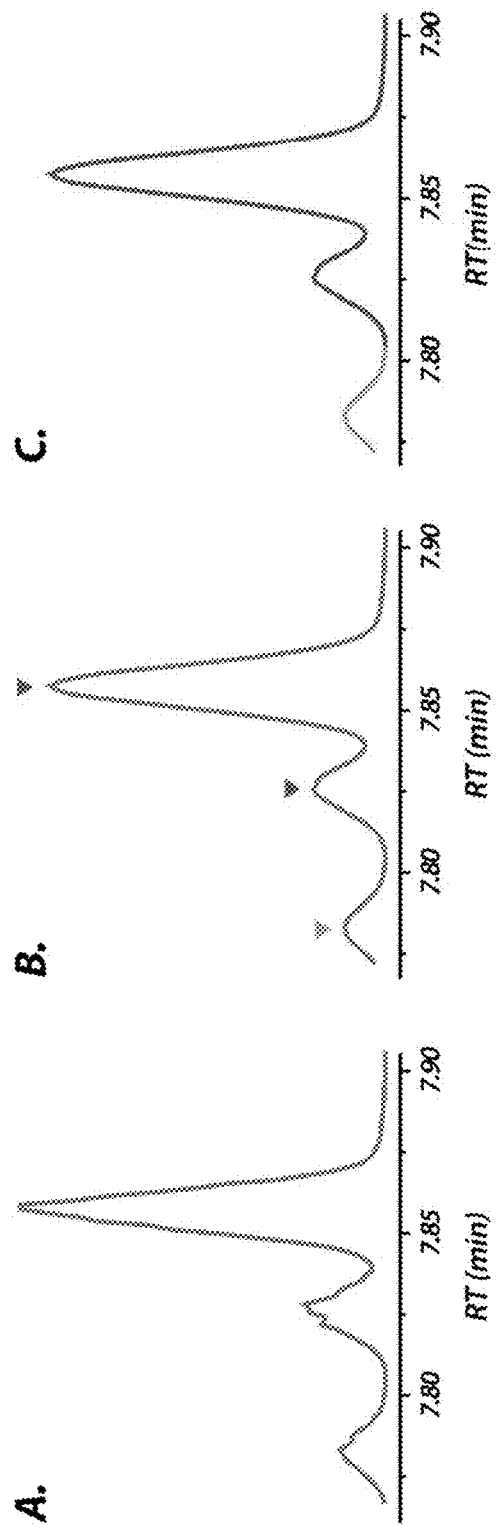
FIG. 4 shows a tri-modal feature in one embodiment, where the tri-modal feature is presumed to be a common fragment to three separate precursors eluting near one another in a GC gradient (A). The feature is smoothed using a 9-pt boxcar average and local maxima are detected at time points indicated by triangles displayed above the smoothed feature (B). Local minima are found between these maxima and the feature is split into three separate pieces each corresponding to a different parent molecule (C).

The ideal case for a feature is that as soon as the peak appears its signal rises to some apex and then continually falls until it is no longer present. However, since many small molecules generate the same fragments this is not always the case. Often, molecules which elute close to one another will have shared fragments whose signal does not drop to 0 between their elutions. Features where the signal rises, falls, rises again, falls again, etc. are frequently observed. To account for this, a peak-picking algorithm was written which detects local maxima and minima based on how quickly a feature's signal rises (slope upwards) and falls (slope downwards). Using this peak-picking process, it was possible to separate out common fragments stemming from separate parent molecules into different features (FIG. 4).

After grouping individual peaks into features, those features which elute close to on another need to be grouped together based on the assumption that they are fragments stemming from the same parent. Before this grouping step, a check of all the features which have been pulled out of the raw data is performed to remove noise. It is presumed that signal from every fragment will rise and fall in a characteristic manner such that it should reach some apex during its elution. This is an important characteristic of analyte signal which can be used to distinguish it from signal due to noise. To help make these patterns easier to observe, the data is smoothed using a 9-point boxcar average. This smoothing step makes the general rise/fall trends of fragment elution more obvious. Because noise is generally constant throughout a run, it is expected that any features comprised of noise peaks would not exhibit this peak-like shape. Rather, most noise signal should remain fairly constant after smoothing. To filter away noise, every feature is checked to see if it reaches an intensity that is greater than twice its minimum signal. This threshold was set as it showed to effectively remove features stemming from noise.

Fragments from a parent molecule will elute at the same time. Because of this, it is expected that the signal from a parent molecule's fragments would rise and fall in a manner consistent with the amount of parent eluting in time. The goal now is to group all fragments from the same parent together for every compound present in the mixture. Two grouping steps are carried out. The first step is more general wherein all features which were observed within a certain time window are placed together into Major Groups. This window is set to be longer than it would take for a molecule to elute from a column (typically about 5 seconds although this varies based on abundance and time into the GC gradient). Note that it is possible for the same feature to be put into multiple groups. This step is important for reducing the problem size passed to the next grouping step. After this initial grouping is carried out, all features in every Major Group are rank ordered based on maximum intensity of the feature.

Another grouping step is then performed which creates Minor Groups containing only those fragments from a particular parent. Starting with the apex of the most intense feature in the Major Group, the time range during which the feature has an intensity >95% of its apex intensity is determined. It is assumed that any other feature which reaches an apex within this time window is also a fragment from the same parent molecule. A new Minor Group is created which all such fragments will be added to. The algorithm then moves to the next most intense feature in the Major Group and checks if it has an apex in this window, if so it is added to the Minor Group and marked as having been included. If not, the algorithm moves to the next most intense feature and performs the same check. This process is repeated until every feature in the Major Group has been checked. The algorithm then moves back to the top of the list and finds the most intense feature which has NOT yet been added to a Minor Group. The algorithm finds the same 95% apex time window and repeats the same process. This is done until every feature in the Major Group has been added to a Minor Group. Minor Groups containing fewer than 5 peaks are assumed to contain insufficient information to produce a correct identification and are subsequently discarded.

Figure 5:
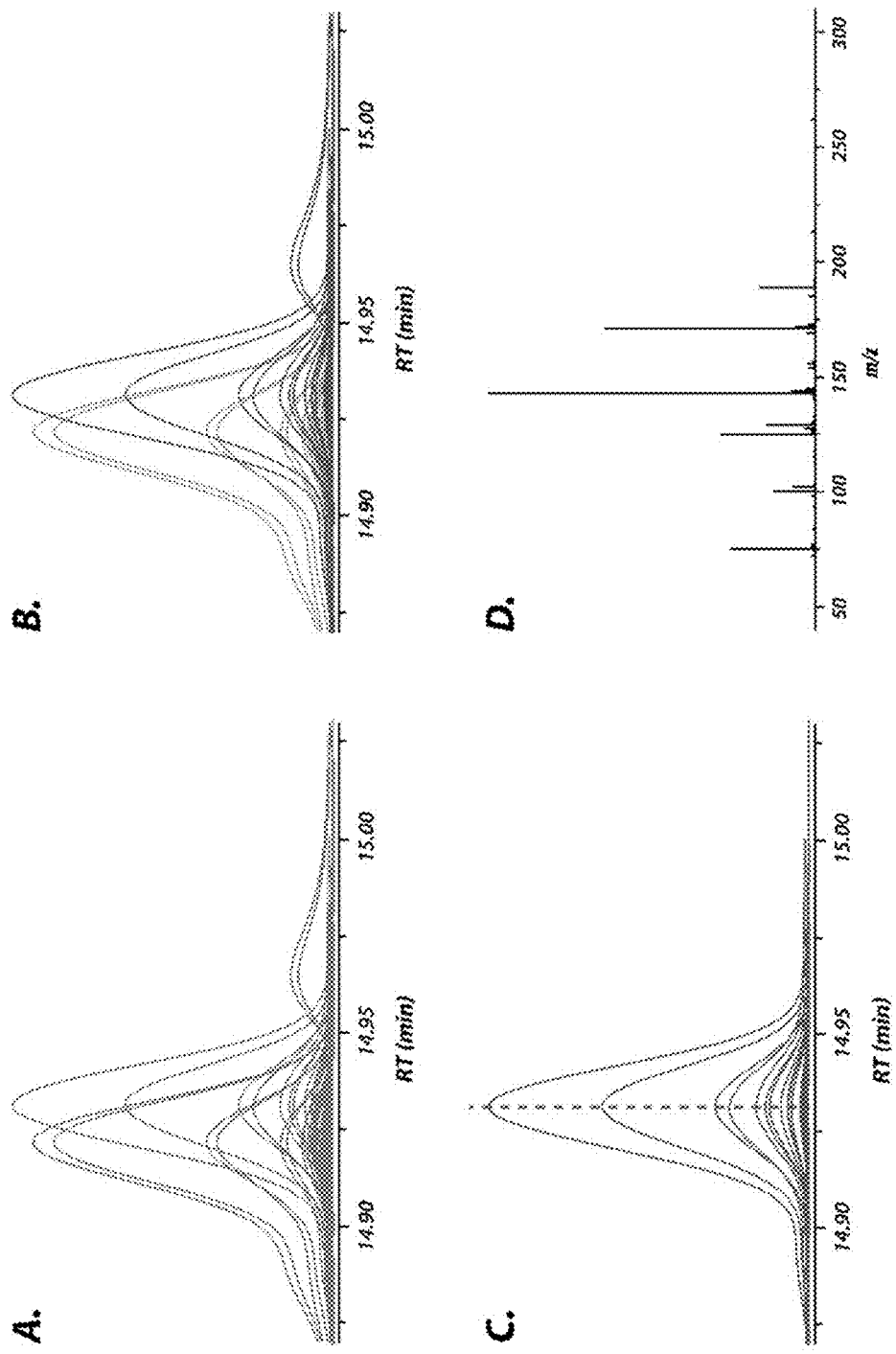
FIG. 5 illustrates the deconvolution step in one embodiment of the invention having a major group containing a number of smoothed features eluting near one another in time (A). The algorithm groups these features into three minor groups according to elution apex (B). Each separate minor group can be indicated by a unique color or line. From these minor groups the intensity of each feature is calculated at the apex indicated by the dashed line (C) and a "pure" mass spectrum constructed for each group (D) which can then be down-converted to unit-resolution spectrum and used for spectral matching.

At this point in the algorithm, a set of Minor Groups containing only fragments which stem from the same parent molecule has been produced. This process has effectively removed noise, and separated fragments from other co-eluting species. Every single peak in the raw data file has been considered so it is practically impossible to have missed any compounds which have eluted, save for those which are exceedingly lowly abundant and would not produce confident identifications. To convert these Minor Groups into "pure" EI spectra, new spectra objects are created which contain peaks corresponding to the m/z values of all features in the Minor Group with their intensity at the apex time point of the group. FIG. 5 shows all feature grouping steps (A-C) and subsequent extraction of a "pure" spectrum (D).

Spectral Matching

The typical means for determining compound identification using EI GC-MS is to compare an extracted spectrum against a set of reference spectra and calculate spectral overlap. The reference spectrum with the highest overlap is assumed to be a correct match. Several schemes for determining spectral overlap exist. The simplest method of doing so would be to calculate the absolute difference between two spectra. To do this, one would determine which peaks were present in both the experimental and reference spectra and subtract their intensities from one another. The reference spectrum which results in the smallest amount of unexplained intensity would be considered the correct match. This approach gives equal weight to all peaks in the spectrum which is ill-advised as larger peaks are significantly more diagnostic in assigning identifications. Consider a molecule which produces a fragment at 300 m/z. There are fewer molecules in existence which can theoretically produce a fragment at 300 m/z than there are which can produce a fragment at 200 m/z. To account for this, a dot product calculation to measure spectral overlap is used. This strategy for measuring spectral similarity gives more weight to larger m/z peaks. Using a traditional dot product, spectral similarity is primarily dictated by the largest peaks in the spectrum. For instance, if there is one dominant peak present in the spectrum and several smaller peaks at different m/z values, a high-scoring match may be returned even if only the largest peak is matched. A more appropriate strategy would be to use a weighted dot product which gives less importance to the largest peaks in the spectrum and consequently more weight to the smaller peaks which may be more diagnostic. Alternative schemes for measuring spectral overlap are available; however the described calculation was used for algorithm development purposes.

Using the "pure" high-res EI spectrum extracted using the deconvolution algorithm, a down-converted pseudo-unit-resolution EI spectrum is created where all peak m/z values are rounded to the nearest integer value. This spectrum is then compared against the entire user-specified database, a weighted dot product for each spectral comparison is calculated, and the top N highest scoring matches are stored. To compare an average spectrum against the entire NIST database (~213,000 spectra) and calculate a weighted dot product for each takes ~1.5 seconds. One of the benefits provided by this algorithm is its speed of execution. Using the NIST MS Search algorithm, comparison of a single spectrum against <10,000 spectra takes approximately the same amount of time. It was decided that search space should be opened as much as possible to increase the chance that an extracted spectrum gets compared against its true reference spectrum, pending that it is present in the database. At this point in the algorithm, a set of candidate identifications is produced complete with associated chemical formulas for each deconvolved high-resolution spectrum. From here, the high-resolution/accurate mass measurements can be leveraged to greatly increase the confidence in assigned identifications and discriminate against false hits.

Figure 6:
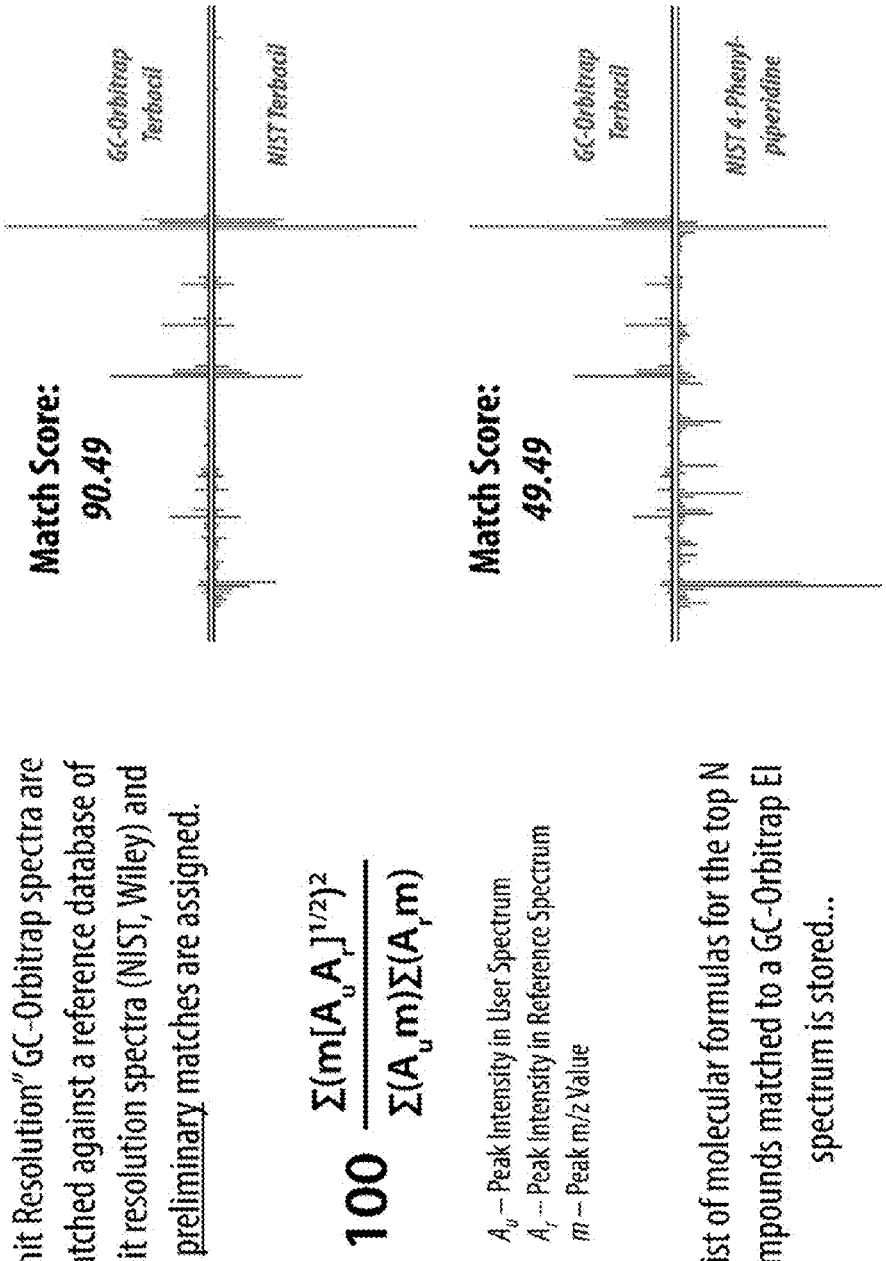
FIG. 6 shows a unit-resolution spectral match between experimentally obtained spectrum for terbacil compared with unit-resolution reference spectra of terbacil and 4-phenyl-piperidine (obtained from NIST reference libraries) in one embodiment of the invention. An initial match score of 90.49 is obtained when the experimental spectrum of terbacil is compared with the reference spectrum for terbacil, while a match score of 49.49 is obtained when the experimental spectrum for terbacil is compared with the reference spectrum for 4-phenyl-piperidine.

FIG. 6 shows experimentally obtained spectrum (user spectrum) for terbacil matched with unit-resolution reference spectra of terbacil and 4-phenyl-piperidine (obtained from NIST reference libraries). Using the following formula, $$100 \frac{\sum (m[A_u A_r]^{1/2})^2}{\sum (A_u m) \sum (A_r m)}$$

$A_g$ – Peak Intensity in User Spectrum
$A_r$ – Peak Intensity in Reference Spectrum
$m$ – Peak $m/z$ Value an initial match score of 90.49 is obtained when the experimental spectrum of terbacil is compared with the reference spectrum for terbacil, while a match score of 49.49 is obtained when the experimental spectrum for terbacil is compared with the reference spectrum for 4-phenyl-piperidine.

High-Resolution Filtering

As was stated previously, this algorithm operates on the principle that every single fragment peak in a pure fragmentation spectrum of a compound contains some subset of the atoms from the parent molecular structure. Now, if a true match is in fact included in this list of candidate matches, it would be expect that every peak observed could be explained using the exact mass of some fragment from the molecule. The percent of signal from accurate mass peaks (total ion current or TIC) that can be annotated with an exact mass fragment can be used as a metric for determining whether or not a correct match was made.

Several algorithms exist which attempt to take a known molecular structure and predict what fragments will be produced based on known bond energies as well as how atoms are connected in space. These algorithms frequently fail to accurately predict all observed fragments which would prohibit implementation of our proposed workflow for assigning identifications. Instead, the present algorithm generates a set of chemical formulas which contains every possible fragment that a candidate molecule could produce. This is done by constructing all non-repeating combinations of atoms in the parent molecular formula. While this approach will generate several impossible formulas, such formulas are simply looked over since only those fragments which have an exact mass falling within a narrow m/z tolerance around an observed peak (approximately 15 ppm) will be utilized. This approach is guaranteed to generate all observed fragments and does not require any a priori knowledge of how the molecule will fragment, or how it will rearrange before fragmentation. However, a fundamental limitation of rule-based fragmentation schemes is that not all possible molecular rearrangements which can occur in the gas-phase, under high vacuum in a mass spectrometer are known. Discovery of every possible rearrangement is unlikely to happen in the near future (if ever) which is a significant detriment to rule-based fragmentation algorithms.

To generate all possible fragments, an array of integers representing each matched chemical formula is first created. In this scheme each index in the array represents a particular atom and the number stored in that index is equal to the count of that atom in the molecule. This process starts with an empty array where zeros are stored for each atom and recursively increments the number stored in each index until the original atom count is reached. This is approach is shown below for the simple case of ethyne ($C_2H_2$) in FIG. 7, where the possible combinations would be H, $H_2$, C, $C_2$, CH, $C_2H$, $CH_2$, and $C_2H_2$. It can be seen that every possible combination of formulas (fragments) is produced using this implementation. Now, using the exact masses of each fragment in this set, it can be determined whether the accurate masses of each peak observed in the high-resolution spectrum can be explained. A benefit of using this approach for rapid annotation of observed peaks is that it can potentially discover new gas-phase chemical rearrangements based on product fragments generated from the electron impact ionization process.

Using the information gathered here to discriminate against false matches is extraordinarily easy. If none (or even very few) of the peaks observed in a high-resolution EI spectrum can be explained using exact mass fragments from a potential candidate, it can be concluded with high-confidence that said molecule did not produce the spectrum which was collected. This process of discriminating against candidate matches has to this point been impossible by matching unit-resolution spectra against unit-resolution reference libraries due to the absence of accurate mass measurements.

Conversely, the process of validating a spectral match as correct is made much easier. If every peak in an experimentally-derived high-res GC-MS spectrum can be explained, it can be certain that some molecule containing this set of atoms must have produced the peaks which were observed. However, there exist many compounds which contain the same set of atoms although their arrangement in space is very different. If there is a large degree of spectral overlap between the experimental and reference spectrum and all observed peaks can be explained, the confidence that the correct compound has been matched is greatly increased. To combine these two components into a single numerical representation of this confidence, that algorithm returns the product of spectral similarity (measured from 0 to 100 where 100 is complete spectral overlap) and the percent of the TIC that can be explained by exact mass fragments (see for example, FIG. 8).

It is acknowledged that in some cases molecules which contain the same parent chemical formula and are arranged in a similar manner (stereoisomers for instance) produce similar spectra. Using only these two pieces of information still likely cannot definitively assign a correct identification. However, additional dimensions of information (retention indices in GC separation) and methods of analysis (NMR, etc.) may be used to determine what compound has been analyzed. In cases such as these, the present algorithm groups all top matches together and returns the group as a hit to the user.

Preliminary Data

Figure 8:
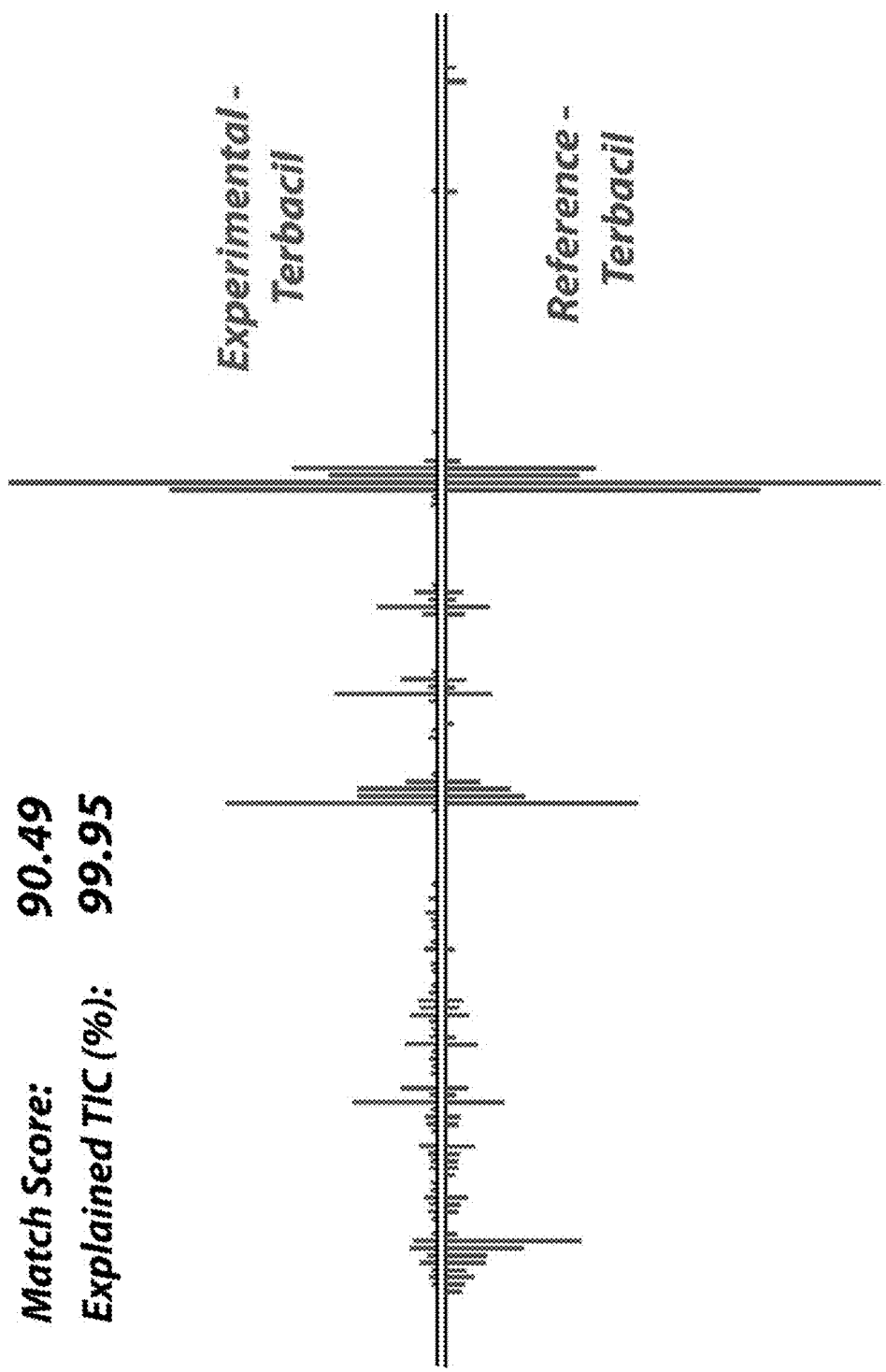
FIG. 8 shows a unit-resolution spectral match returned from a database search of a known spectrum of terbacil in one embodiment of the invention. The experimentally collected spectrum is displayed in on the top and the reference spectrum on the bottom. A high-degree of spectral overlap is noted and a spectral match score of 90.49 is returned. Using a high-resolution filtering algorithm of the present invention, 99.95% of the total ion current (TIC) signal can be explained when the theoretical fragments of terbacil are matched to the observed high-resolution peaks.
Figure 9:
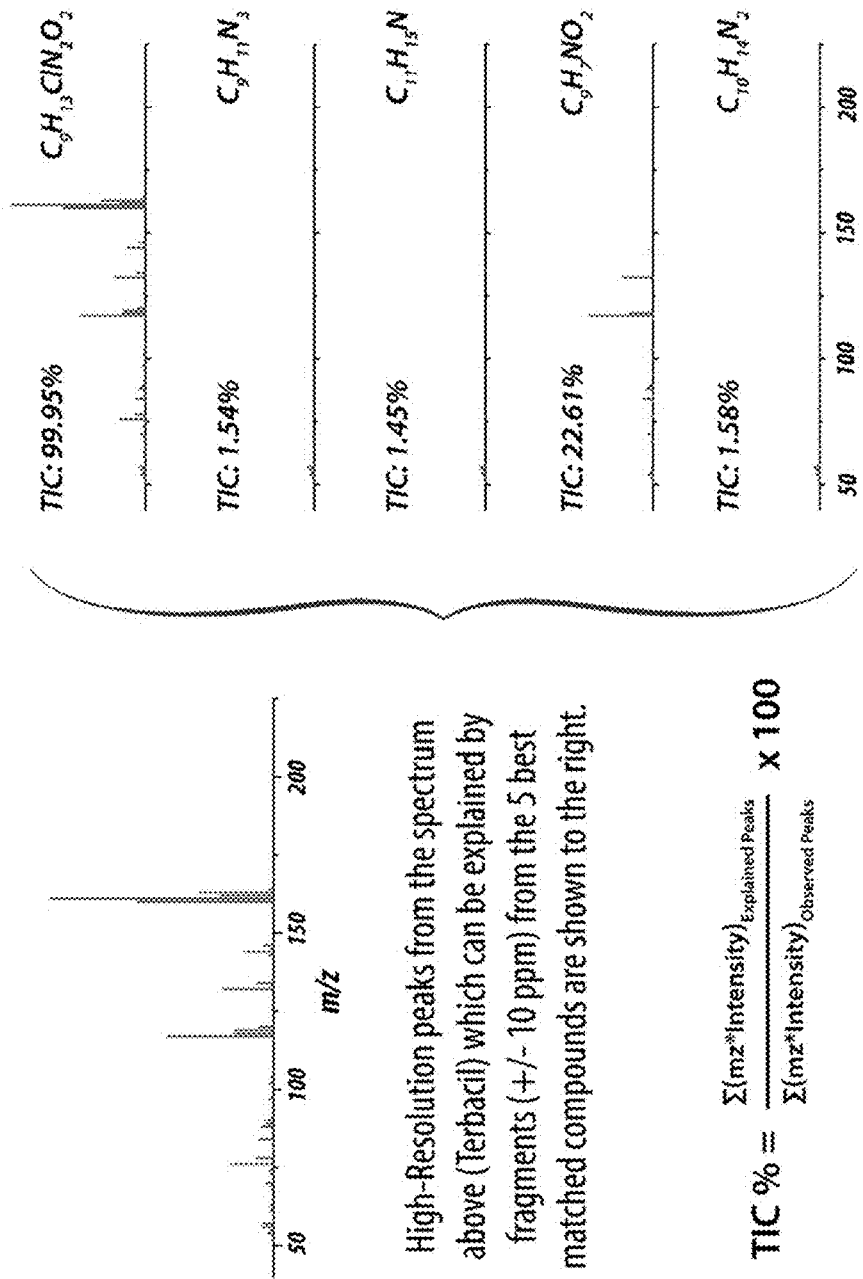
FIG. 9 illustrates a high-resolution filtering stage. The theoretical fragments that would be produced that the top compounds from the spectral matching step are generated and compared with the observed high-resolution peaks of terbacil. As a result, 99.95% of the total ion current (TIC) can be explained when the theoretical fragments of terbacil are matched to the observed high-resolution peaks.

For initial validation of the algorithm, a sample mixture containing known pesticides suitable for analysis with GC-MS was analyzed. The following examples highlight the efficiency of the present algorithm and how it can be used to increase the confidence in assigned identifications and discriminate against false hits with high fidelity. The analysis of terbacil generated the following spectrum which was matched correctly to a reference spectrum of terbacil in the NIST 12 MS Library. The spectrum was matched with a score of 90.49 and we were able to explain 99.95% of the TIC in the high-resolution spectrum (FIG. 8 and FIG. 9). Any unmatched signal was attributed to mass errors outside of the narrow allowable mass tolerance, or to peaks which were spuriously included in the deconvolution step. This is an ideal case in which a large degree of spectral overlap was observed and almost all of the peaks in the high-resolution spectrum can be explained.

It is noted that instances where the algorithm is efficient in discriminating against hits where the low-res match scores between the top hits are relatively close (similar reference spectra were matched). For example, in the case of molinate the top two hits (Molinate and 2-Methyl-1,3-cyclohexanedione respectively) have low-res match scores of 82.41 and 75.16. Visual interpretation of the unit-resolution spectra suggests that either compound could potentially be a correct match as the dominant peaks in both reference spectra are matched. However after carrying out the high-resolution filtering step, it was found that only 19.30% of TIC could be explained using the chemical formula from 2-Methyl-1,3-cyclohexanedione, whereas 99.63% of the observed signal using molinate's chemical formula can be explained (FIG. 10). This is example highlights the utility of the algorithm in reducing the ambiguity between similar spectral matches. It would have been impossible to discriminate against these two hits solely by matching the low-resolution reference and experimental spectra, however the present method is able to conclusively rule out 2-Methyl-1,3-cyclohexanedione as a correct match using the algorithm.

Figure 11:
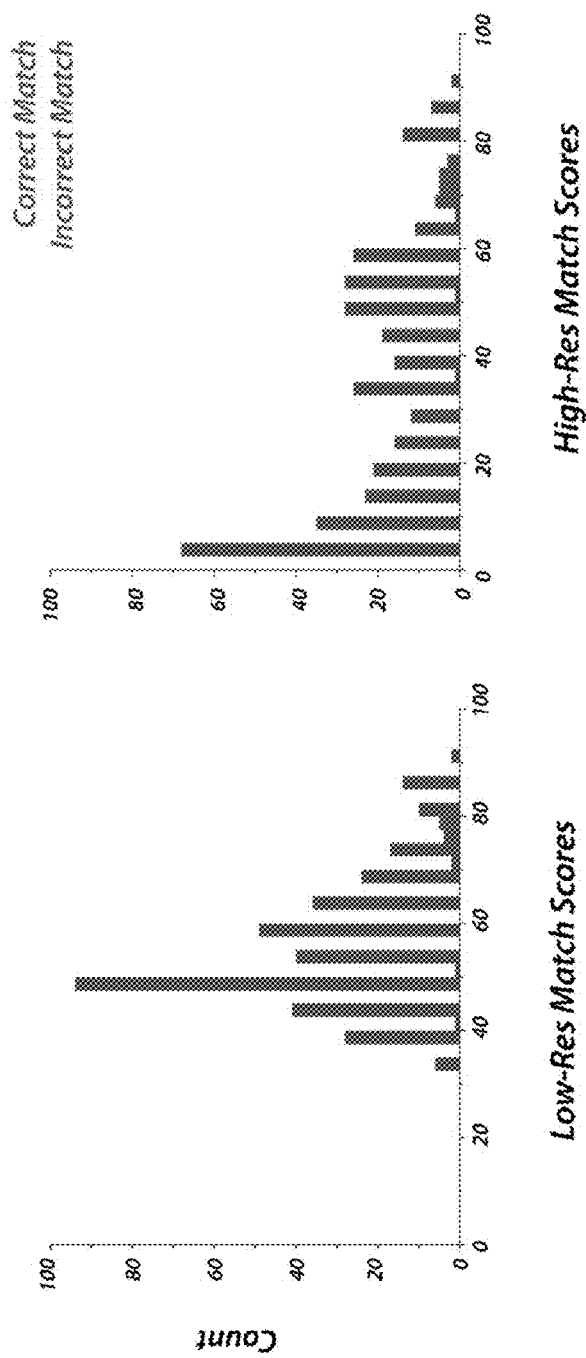
FIG. 11 shows the top ten returned spectral match scores for a set of 34 known pesticides when matching against a unit-resolution reference database containing ~213,000 spectra (NIST12). The score for each correct match is shown in red, while the scores for false hits are shown in blue. After applying the high-resolution filter and calculating high-res match scores, it was seen that the distribution of incorrect scores skews downwards with the largest population of scores falling to nearly 0. This result highlights the efficiency of the algorithm in one embodiment of the present invention in discriminating against false matches.

The algorithm also performed well in the analysis of a larger dataset (34 known pesticides). Shown in FIG. 11 are the match scores for the top 10 hits of all known compounds with the scores for the correct matches and incorrect matches shown. After carrying out the high-resolution filtering step, it is seen that many of the incorrect scores drop significantly with the largest population of scores dropping to near 0. This result highlights the utility of the algorithm in selecting against false matches. An analyst using GC-MS as a tool for small molecule analysis would benefit using this algorithm as one can gain a great deal of confidence in returned spectral matches without any additional experimentation.

Additional Applications for the High-Resolution Filtering Algorithm

It is predicted that the fragment generation algorithm can be extended beyond confirming spectral matches assigned to high-res EI spectra collected using GC-MS. Currently available reference libraries do not necessarily contain reference spectra for every compound which can be observed using GC-MS. This approach of High-Resolution Filtering can potentially be expanded to discovery of compounds which are not present in databases. In instances where an experimental spectrum cannot be matched to a reference spectrum with high overlap, a user can begin to search for chemical formulas which can be used to annotate all observed peaks. One approach to do so is to analyze the same sample using chemical ionization which generates spectra containing an intact precursor. From this intact precursor, an accurate mass measurement is obtained that can be matched back to a chemical formula.

This process of chemical formula matching can be done by comparing observed precursor mass against a database of known chemical formulas or by generating all possible chemical formulas containing certain atoms. If one of these chemical formulas with matching exact mass can be used to explain all peaks in an observed spectrum, either that molecule or a molecule with a larger chemical formula (containing all atoms and then some) could be concluded to have produced the spectrum with high confidence. From there, a user could begin to derive the molecular structure of the molecule. Such a process is potentially incredibly valuable to facilitating high-throughput discovery-based analysis of small molecules. Additionally, as was previously suggested, using the algorithm to rapidly annotate observed spectral peaks may be highly informative to discovering novel gas-phase rearrangements and fragmentation pathways.

Example 2: Putative Identification of Norflurazon

One aspect of the invention provides a novel strategy for improving spectral matching of EI fragmentation spectra collected on high-resolution GC-MS instruments using existing databases of reference spectra collected on unit-resolution GC-MS instruments. These high-resolution EI spectra can be matched to the unit-resolution databases by rounding peak m/z values to the nearest whole integer. The returned spectral matches can still be ambiguous, but additional filtering employed increases the identification rate.

Taking the high-resolution spectra, the top N matched compounds are stored, and for each putative identification all non-repeating combinations of atoms are generated from its molecular formula. This set of combinations represents a set of possible fragments. After generating each set of fragments and filtering away impossible formulas the remaining fragments are matched against the high-resolution spectrum at high mass accuracy (i.e., <20 ppm). From this it was determined what percentage of the total ion current (TIC) can be explained by each set of chemical fragments. The method is fully automated by returning a final "high-resolution filtered score" that is the product of the low-resolution dot product match score (0-100) and a weighted percentage of the total measured ion current that can be explained by fragments from a particular matched compound.

Figure 12:
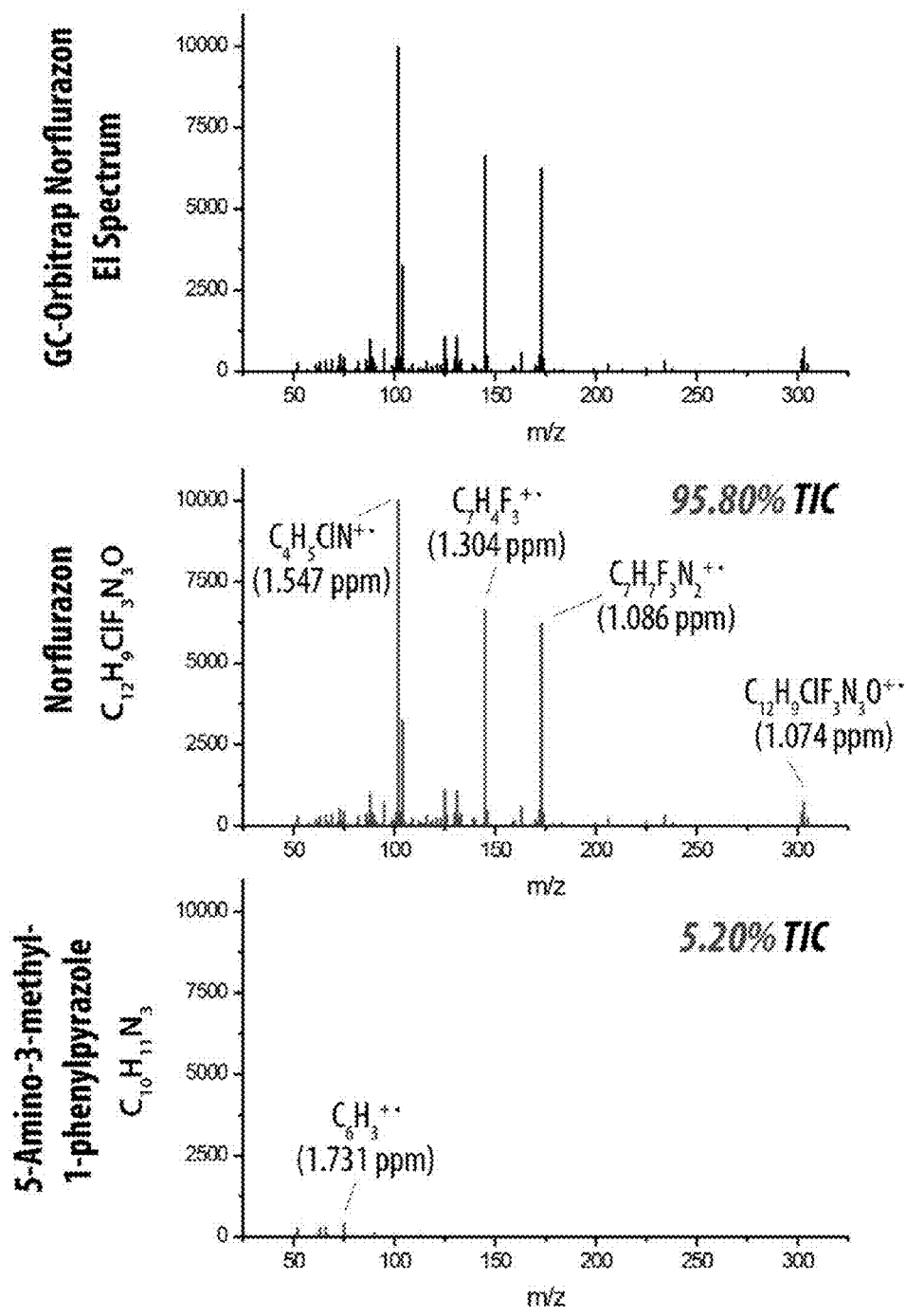
FIG. 12 shows an example of using high-resolution filtering to determine plausibility of a putative identification. A known standard of norflurazon was sampled using the GC-Orbitrap mass spectrometer. The resulting EI spectrum was matched against a database of ~21,000 unit-resolution reference spectra (NIST) and the two best scoring compounds, norflurazon ($C_{12}H_9ClF_3N_3O$) and 5-amino-3-methyl-1-phenylpyrazole ($C_{10}H_{11}N_3$) had match scores of 76.34 and 76.11 respectively. After generating all possible combinations of fragments for both compounds, and filtering away any peaks which did not have a matching fragment within +/−10 ppm the two red spectra remained. For norflurazon 95.80% of the TIC could be explained with an average ppm error of −0.062 (σ=3.214 ppm), while only 5.20% of the TIC for 5-amino-1-methyl-3-phenylpyrazole was explained. Based on this result, the second hit can be effectively ruled out as a candidate match, which could not have been done without accurate mass information.

This technique is illustrated in FIG. 12, which shows an example of using high-resolution filtering to determine plausibility of a putative identification. A known standard of norflurazon was sampled using a GC-Orbitrap mass spectrometer. The resulting EI spectrum was matched against a database of ~21,000 unit-resolution reference spectra (obtained from NIST) and the two best scoring compounds, Norflurazon ($C_{12}H_9ClF_3N_3O$) and 5-Amino-3-methyl-1-phenylpyrazole ($C_{10}H_{11}N_3$) had match scores of 76.34 and 76.11 respectively. After generating all possible combinations of fragments for both compounds, and filtering away any peaks which did not have a matching fragment within +/−10 ppm two spectra remained. For norflurazon 95.80% of the TIC could be explained with an average ppm error of −0.062 ($\sigma$=3.214 ppm), while only 5.20% of the TIC for 5-Amino-1-methyl-3-phenylpyrazole was explained. Based on this result, the second hit can be effectively ruled out as a candidate match, which could not have been done without accurate mass information.

Figure 13:
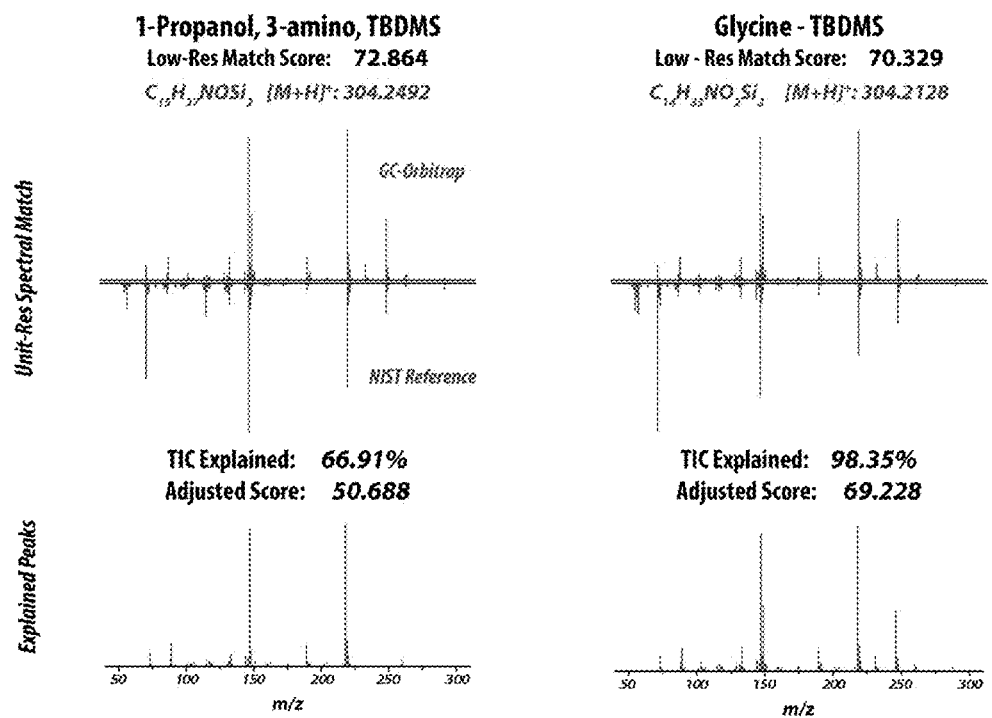
FIG. 13 shows the top two spectral matches (1-propanol, 3-amino, TBDMS and glycine-TBDMS) returned from a database search of glycine-TBDMS. The experimentally derived spectrum is shown on top, and the corresponding NIST reference spectra are shown on the bottom. Using the algorithm in one embodiment of the present invention, it was found that 98.35% of the observed TIC signal can be explained using the chemical formula of glycine-TBDMS ($C_{14}H_{33}NO_2Si_2$) but only 66.91% of the observed signal using the chemical formula of 1-propanol, 3-amino, TBDMS ($C_{15}H_{37}NOSi_2$).

Example 3: Using High-Resolution Filtering to Distinguish Between Two Similar Compounds A sample of glycine was derivatized using a tert-butyldimethylsilyl label and the experimentally derived spectrum searched against the NIST12 unit resolution EI reference library. The top two unit-res spectral matches returned were to 1-propanol, 3-amino, TBDMS and glycine-TBDMS with scores of 72.864 and 70.329 respectively (see FIG. 13). It is worth noting that the unit resolution reference spectra of the two compounds contain nearly all of the same prominent features. Using the standard mechanism of comparing unit-resolution reference spectra to identify EI spectra in this instance would have likely led to the wrong identification since 1-propanol, 3-amino, TBDMS had a higher spectral matching score. However, when the high-resolution filtering approach was used as described herein, it was found that only 66.91% of the observed TIC could be explained in the high-resolution EI spectrum with the chemical formula of 1-propanol, 3-amino, TBDMS ($C_{15}H_{37}NOSi_2$).

In contrast, 98.35% of observed TIC can be explained using the chemical formula of glycine-TBDMS ($C_{14}H_{33}NO_2Si_2$). After rescoring the matches to take into account the explained TIC, the spectrum for glycine-TBDMS (which was previously the second best scoring spectral match) was moved to the top of the list. This identification was confirmed by observation of an intact precursor in a corresponding CI run of the same sample within 5 ppm.

Example 4: Using High-Resolution Filtering to Distinguish Between Multiple Similar Compounds A sample of malonate was derivatized with a tert-butyldimethylsilyl label (Bis (TBDMS) malonate) and the experimentally derived spectrum searched against the NIST12 unit resolution EI reference library. The top five best scoring spectral matches were returned (see FIG. 14) with scores ranging from 66.610 (2-methyl-1,4-butanediol, bis (TBDMS) ether) to 60.773 (Bis (TBDMS) malonate). All reference spectra contained similar prominent features and distinguishing the correct spectrum on the basis of spectral overlap is nearly impossible. In fact, the correct compound, Bis (TBDMS) malonate, had the lowest spectral matching score of the five returned spectra.

However, after using the high-resolution filtering algorithm, the chemical formula of Bis (TBDMS) malonate explained a larger percentage (99.719%) of the observed TIC in the spectrum than any of the other compounds (see FIG. 14). After rescoring the spectral matches to include this explained TIC component, the correct spectral match moves to the top of the list. Without use of the algorithm it would have been nearly impossible to distinguish the correct answer from the list of similar scoring spectral matches. This identification was confirmed by observation of an intact precursor in a corresponding CI run of the same sample within 5 ppm.

It was also noticed that several of the prominent features in the experimentally derived spectrum could be explained by a fragment from the chemical formula of all five best scoring spectral matches. The largest feature which can be explained by all spectral matches is annotated with the formula $C_5H_{15}OSi_2$. This makes sense as each matched chemical formula contains at least five carbons (C), fifteen hydrogens (H), one oxygen (O) and two silicons (Si). The next most intense peak can be explained using the chemical formulas of four out of our top five spectral matches. This fragment is annotated with the formula $C_8H_{21}OSi_2$. In this instance, the only parent formula which cannot theoretically produce a fragment with this mass is Bis (TMS) methylboronate which only has seven carbon molecules in its structure. Finally, there is a prominent feature in the experimentally-derived EI spectrum of Bis (TBDMS) malonate which can only be explained by its chemical formula. This feature is annotated with the formula $C_{11}H_{23}O_4Si_2$. It makes sense that the mass of this peak cannot be explained by the other chemical formulas as Bis (TBDMS) malonate is the only chemical formula of the group which contains four oxygen atoms.

Example 5: Chemical Formula Elucidation without a Reference Spectrum

Figure 15:
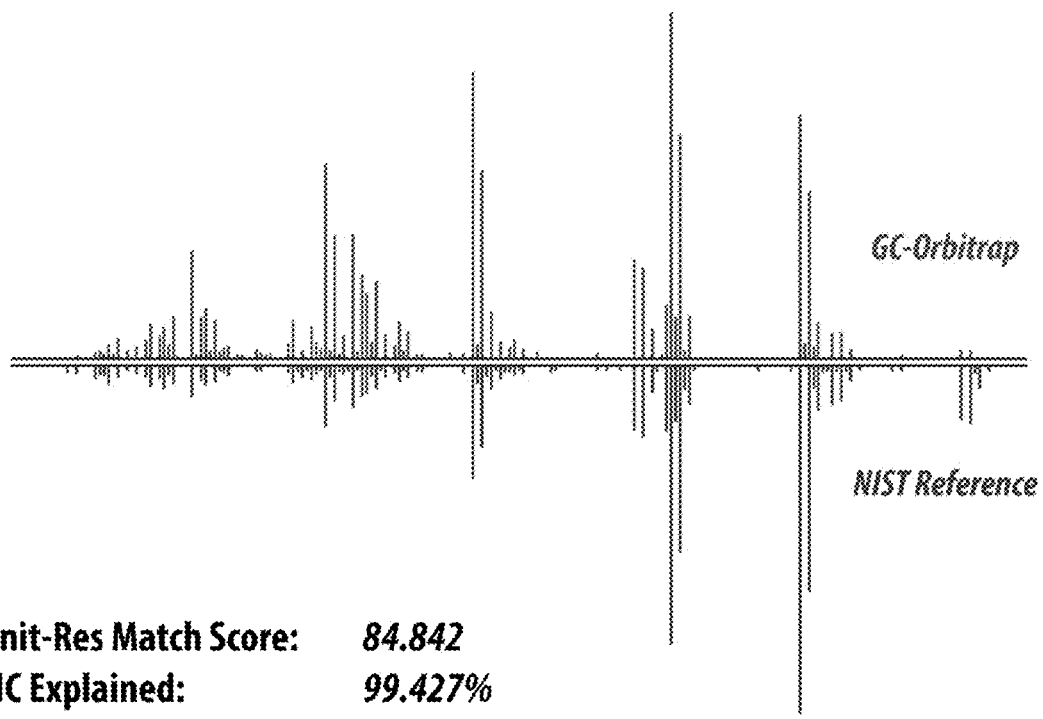
FIG. 15 shows an obtained experimental spectrum of etridiazole compared with the NIST reference spectrum.

A known standard of etridiazole was analyzed and the experimentally derived EI spectrum searched against the NIST12 unit resolution EI reference library. The reference spectrum to etridiazole was returned with high spectral overlap (84.842) and high TIC percentage explained (99.427%) (see FIG. 15). This result suggested that the experimentally derived spectrum was very high quality. This spectrum was then used to determine whether the minimum chemical formula needed to explain the vast majority of the observed TIC in the experimental spectrum could be identified.

Figure 16:
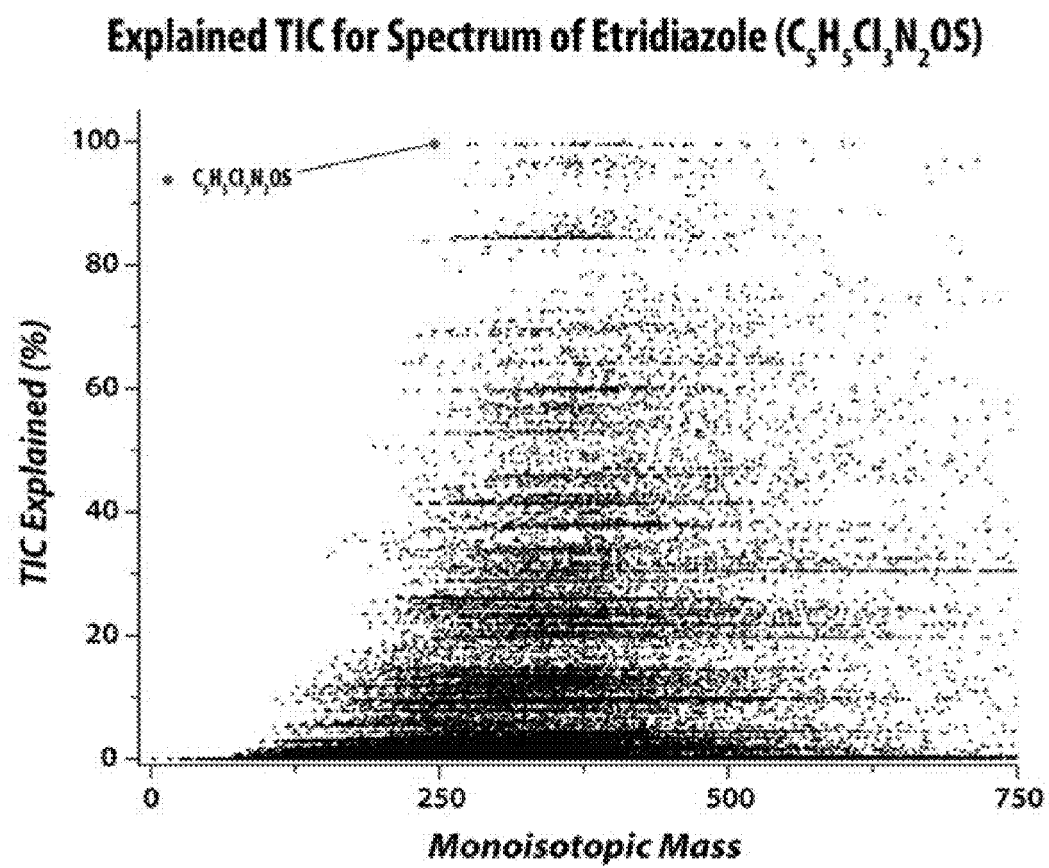
FIGS. 16-18 show the percentage of TIC signal that could be explained for the experimentally derived spectrum of FIG. 15 by each unique chemical formula plotted against its monoisotopic mass.
Figure 17:
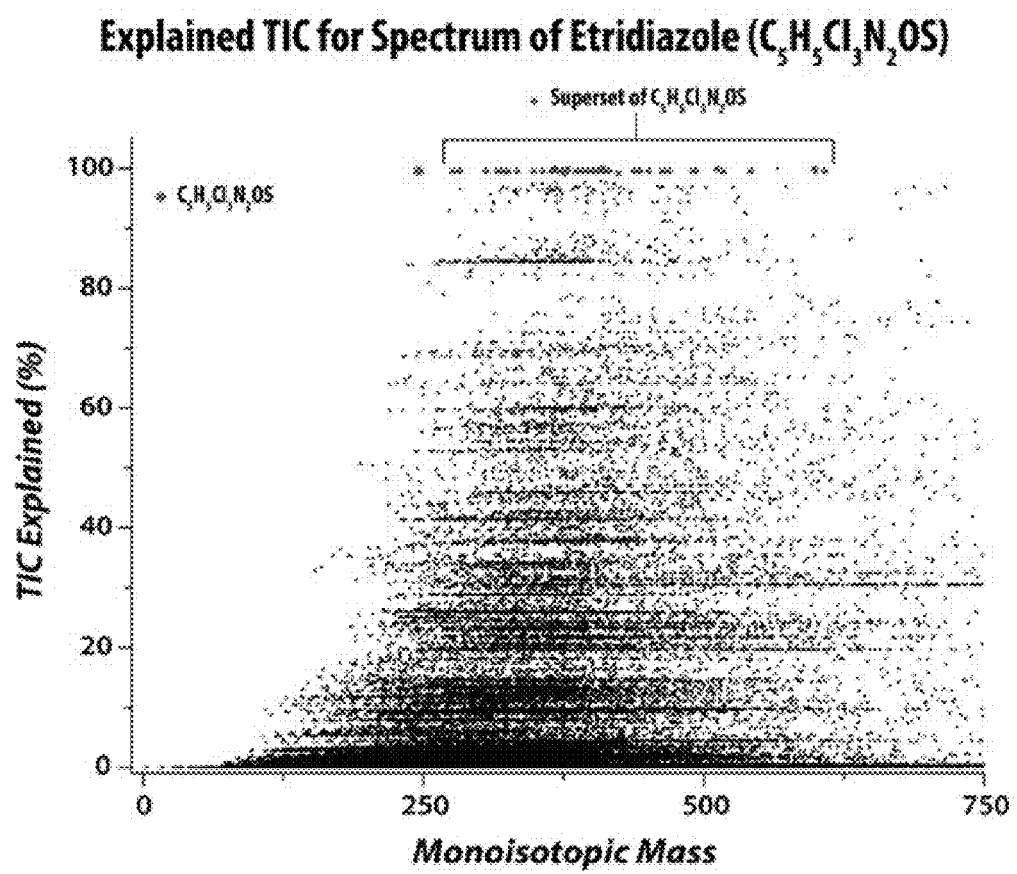
Figure 18:
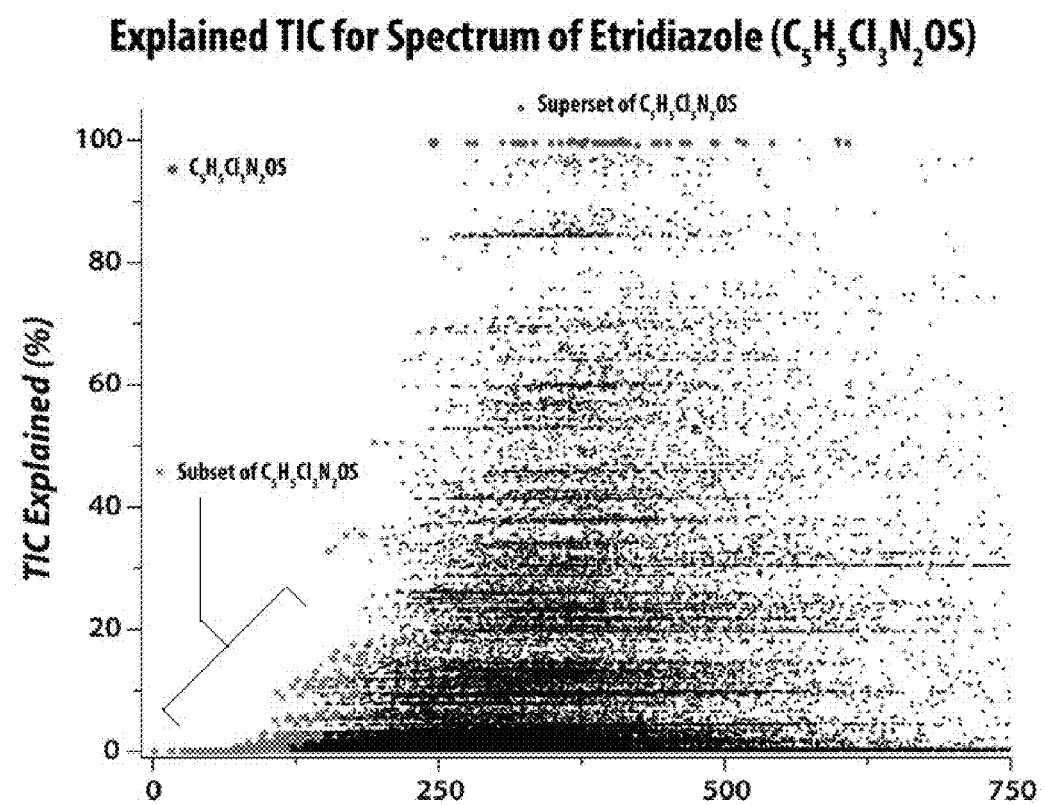

The percentage of TIC signal that could be explained for the experimentally derived EI spectrum of etridiazole by every unique chemical formula in the NIST12 reference database was calculated. Shown in FIG. 16 is the percentage of TIC that can be explained by each unique chemical formula plotted against its monoisotopic mass. It is notable that very few compounds can explain a large percentage (>=90%) of the TIC. The point corresponding to the chemical formula of etridiazole ($C_5H_5Cl_3N_2OS$) was plotted and identified. This point corresponds to the smallest formula that can be used to explain an exceedingly large percentage of the observed TIC in the EI spectrum. Also plotted were the supersets (FIG. 17) and subsets (FIG. 18) of $C_5H_5Cl_3N_2OS$, and it was noted that almost every chemical formula which can explain the greatest percentage of the observed TIC contains the base set of atoms $C_5H_5Cl_3N_2OS$.

Using this approach, it could have been determined that it was very likely that a molecule with at least $C_5H_5Cl_3N_2OS$ produced the observed fragmentation spectrum. Measurement of an intact precursor in a corresponding CI run would help to confirm the hypothesis that a molecule with at least this base set of atoms did in fact produce the observed spectrum. This approach of chemical formula elucidation can potentially be extended to discovery-based analysis of compounds which do not have a reference spectrum present in a library. This approach provides a user with a presumed chemical formula for a molecule, along with an annotated EI spectrum. From here the user can begin to elucidate the structure of their analyte.

Figure 19:
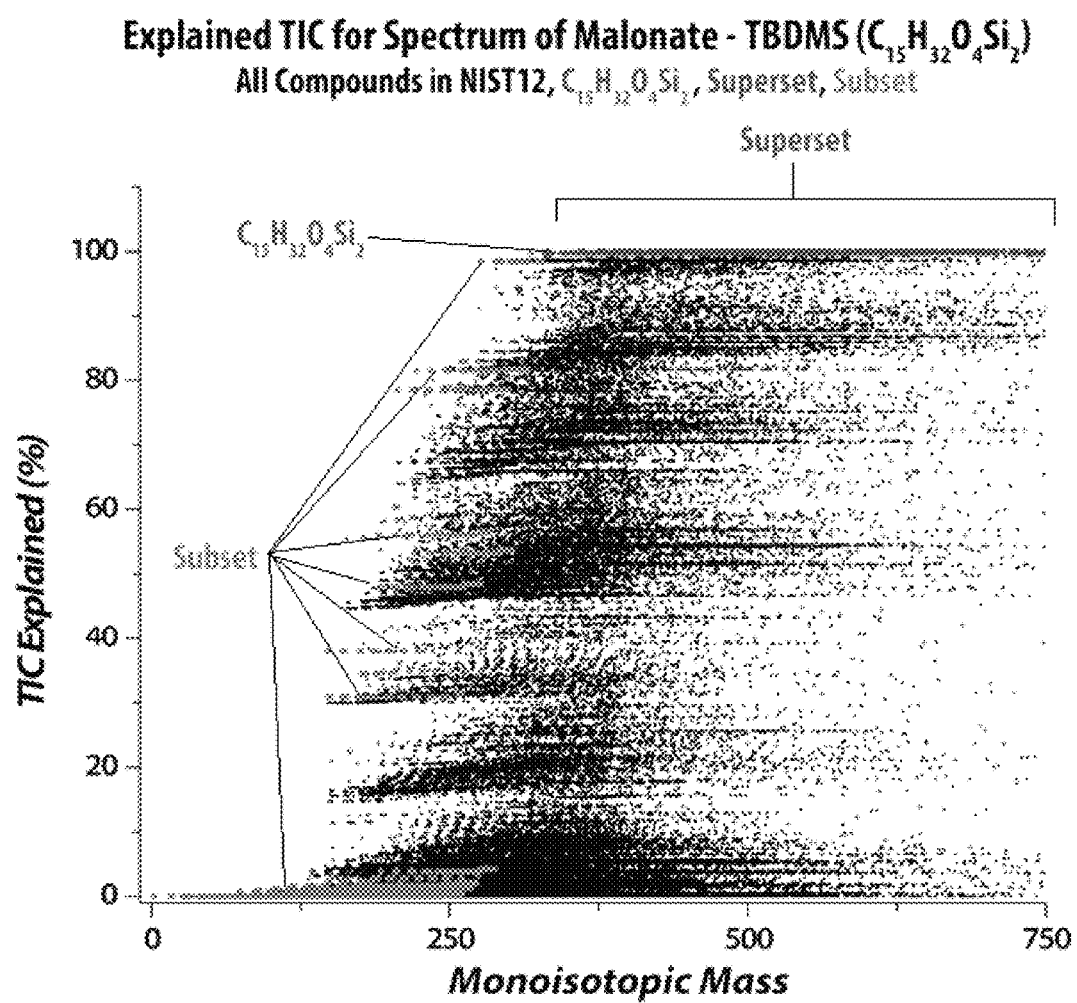
FIG. 19 shows the percentage of TIC signal that could be explained for the experimentally derived spectrum of malonate-TBDMS by each unique chemical formula plotted against its monoisotopic mass. Highlighted are the plot points corresponding to malonate-TBDMS ($C_{15}H_{32}O_4Si_2$) and the supersets and subsets of $C_{15}H_{32}O_4Si_2$.
Figure 20:
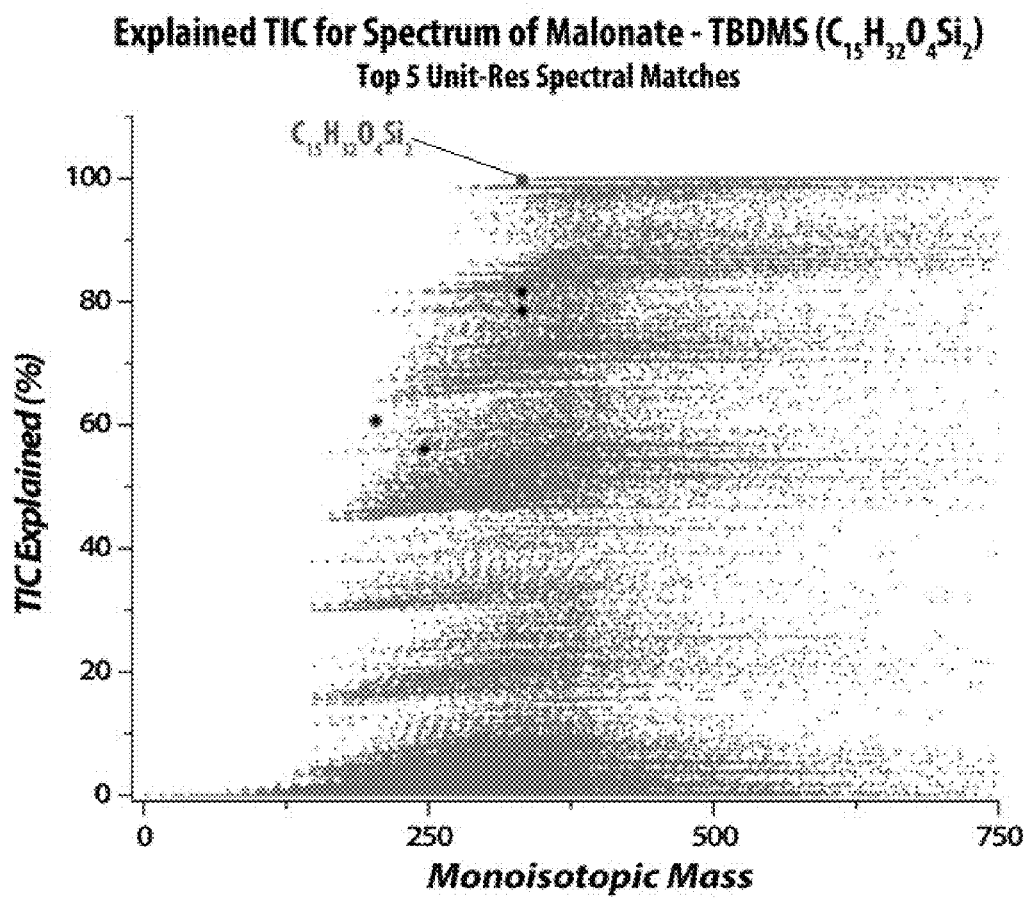
FIG. 20 shows the percentage of TIC signal from FIG. 19 with the plot points corresponding to the top five spectral matches to malonate-TBDMS highlighted.

The same analysis as described above was performed for the experimentally derived spectrum of Bis (TBDMS) malonate. FIG. 19 shows the percentage of TIC that can be explained by each unique chemical formula plotted against its monoisotopic mass and also plots the supersets and subsets of $C_{15}H_{32}O_4Si_2$. Again, very few compounds are able to explain a large majority of the observed TIC. FIG. 20 shows the percentage of TIC Explained for the top 5 best spectral matches to Bis (TBDMS) malonate (see FIG. 14), with the chemical formula of Bis (TBDMS) malonate ($C_{15}H_{32}O_4Si_2$) being the topmost large dot. This example again highlights the utility in using percentage of observed signal that can be explained as a metric to score spectral matches of high-resolution reference spectra against unit resolution reference spectra.

Example 6: Accurate Mass for Improved Small Molecule Identification Via GC/MS

Obtaining confident identifications for small molecules and metabolites analyzed by GC/MS has proven exceptionally challenging. In this Example we describe a combinatorial approach using high-resolution filtering to determine the plausibility of putative identifications by exploiting accurate mass measurements. The present method provides orthogonal information to traditional spectral matching and retention indexing. Furthermore, it affords all the benefits of increased MS resolution while simultaneously extending the utility of the expansive unit resolution GC/MS reference libraries currently available.

Gas chromatography-mass spectrometry (GC/MS) has long been considered one of the premiere analytical tools for qualitative and quantitative analysis of volatile small molecules[1-3]. Highly reproducible chromatographic separations combined with conserved fragmentation of analyzed molecules lend this technique to both targeted and discovery-based assays. One of the prominent areas where GC/MS has shown utility is in metabolite profiling[4,5]. Metabolomics is quickly emerging as a field of interest for both systems biologists and clinical researchers. Given that the metabolome is furthest downstream from genotype to phenotype many believe that metabolic profiling has the potential to reveal biomarkers and/or characteristic metabolite profiles[6,7]. It is believed that these features can facilitate early diagnosis/prognosis of disease and other conditions. Moreover, metabolite screens are highly desirable in the clinical setting as they are often ranked among the least invasive biological assays. As this field continues to grow there is critical need for the development of advanced tools and technologies to enable deeper profiling in shorter time spans.

In traditional discovery experiments, volatile analytes are separated by GC and ionized using electron ionization (EI) prior to mass analysis. EI is a "hard" ionization technique and causes molecules to fragment in characteristic patterns. Spectra containing fragments from individual analytes (which may or may not include an intact molecular ion) are extracted and then compared to databases of unit-resolution reference spectra[8]. Matches with sufficiently high spectral similarity are often presumed to be correct identifications. Correctly identifying the bulk of observed features in a GC/MS experiment has proven to be a formidable challenge[9,10]. It is not uncommon for the majority of these features to remain unidentified. For those compounds where presumed identifications have been assigned, subsequent validation often necessitates that an analyst run a pure reference standard to corroborate both spectral similarity and analyte retention. This process can be laborious particularly if there exists a large number of putative identifications for a single compound. As such, any auxiliary information which can be used to discriminate between, or guide towards candidate precursors is highly valuable.

For decades unit resolution GC/MS instruments were the norm and the largest publically available reference libraries are comprised of spectra acquired on these systems[11,12]. In recent years, high-resolution instruments have hit the market yet data analysis tools have remained largely unchanged[13-16]. There is great potential in available accurate mass that remains to be capitalized on. For comparison, the introduction of high-resolution mass spectrometers marked a transformation for LC-MS/MS-based proteomics. The predictive nature of peptide fragmentation was advantageous here. Many of the developed peptide-spectral matching algorithms were readily adapted to reduce allowed mass tolerances and achieve a concomitant reduction in search space and increase in precursor/product ion matching specificity. Conversely, small molecule fragmentation patterns are much less predictable. Generation of theoretical EI spectra in silico has proven to be exceptionally challenging and to date algorithms which attempt this task have only shown modest success[17-19]. As an alternative approach, the methods of the present example look to the expansive EI reference databases currently in place. The disparity in available mass accuracy here precludes the ability to directly compare measured exact masses against their reference counterparts. However, these reference spectra are information rich with regards to fragmentation profile and intensity patterns. Furthermore, these libraries would be prohibitively costly to recreate using newer instruments, at least in the near future. We rectify that we can still utilize these libraries for identifying candidate precursors while simultaneously exploiting available mass accuracy.

In this Example, we describe a novel approach for leveraging accurate mass information to increase the specificity of small molecule identifications. The described high-resolution filtering (HRF) approach utilizes a combinatorial process to measure the plausibility of assigned identifications by calculating the percentage of signal in a GC-MS spectrum that can be annotated with an exact chemical formula stemming from a presumed precursor. One embodiment of this strategy uses traditional spectral matching against unit resolution reference libraries to gather candidate identifications. This method effectively provides the best of both worlds by enabling discrimination between precursors on the basis of both measured fragmentation profiles and accurate mass. An alternative model relies on a user-specified chemical formula which can be used to determine the soundness of a presumed identification. This is a convenient alternative for users analyzing novel compounds where a suitable reference spectrum is unavailable. The approach described herein enables GC/MS users to capitalize on accurate mass measurements and unlocks an additional dimension of information which is orthogonal to that provided by spectral matching.

An underlying aspect behind the HRF strategy is that every fragment derived from a particular parent contains a subset of atoms from said precursor. We assert that every peak in a pure high-resolution GC/MS spectrum can be annotated using a combination of atoms from the true parent. Given a high-res GC/MS spectrum and a putative identification, all non-repeating combinations of atoms from the assigned chemical formula are generated and then matched to peaks using exact mass. No approximations as to what formulas can and cannot exist are made. While some of the combinations produced are chemically impossible, the list inherently contains all formulas for fragments which could possibly be observed. Here we demonstrate that the current implementation is viable and highly specific towards correct parent assignments.

Figure 21A:
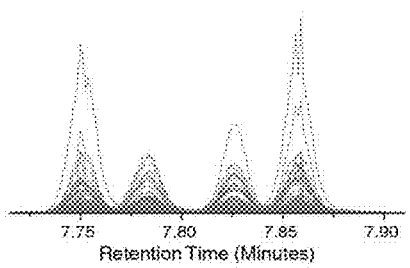
FIGS. 21A-21F show high-resolution filtering workflow with spectral matching.
Figure 21B:
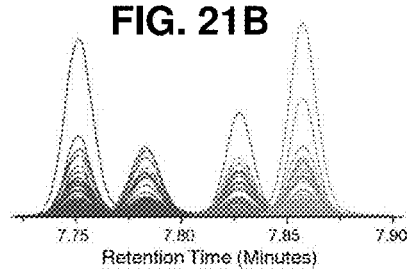
Figure 21C:
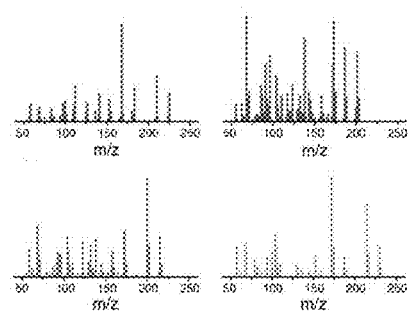
Figure 21D:
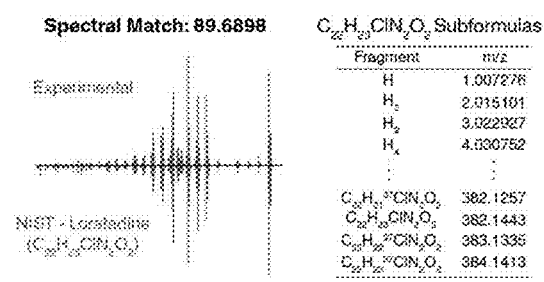
Figure 21E:
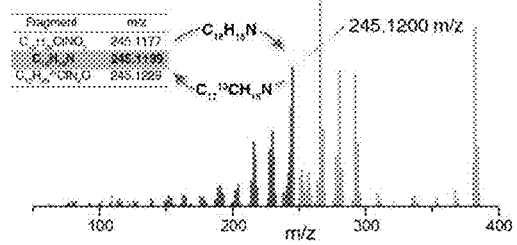
Figure 21F:
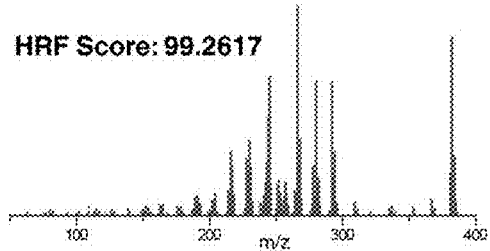
Figure 22A:
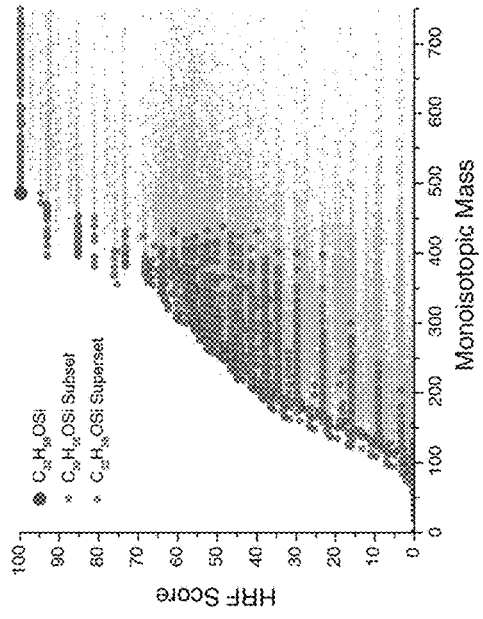
FIGS. 22A-22C show high-resolution filtering results.

We tested the present approach using a dataset of high-resolution GC-Orbitrap spectra collected from 105 pure reference standards covering many classes of small molecules (metabolites, pesticides, drugs of abuse, etc.). Individual spectra were extracted from raw data files using an in-house deconvolution algorithm designed to group together those fragments stemming from a singular precursor. Extracted spectra were submitted for spectral matching against the entirety of the NIST 12 EI Database (~213,000 spectra). A weighted dot product measuring spectral similarity to each compared reference spectrum was calculated and the best scoring matches were returned (FIGS. 21A-21D). Considering only correct hits, for the 105 spectra submitted a median spectral match score of 81.889 with a standard deviation of 9.587 was achieved. Following spectral matching, all returned matches were subjected to our HRF approach. Using the chemical formulas associated with returned spectral matches, the percentage of signal that could be annotated using the exact mass of a subformula from each was returned (FIGS. 21E-21F). Again considering only correct hits, we report a median HRF score of 99.700 with a standard deviation of 1.022 (FIG. 22A and FIG. 29 (Supplementary Table 1)).

FIG. 29 (Supplementary Table 1) provides results from all analyzed reference compounds complete with raw file name, retention time, HRF score, spectral match score, peak count, and the reference spectrum name as reported.

Figure 22B:
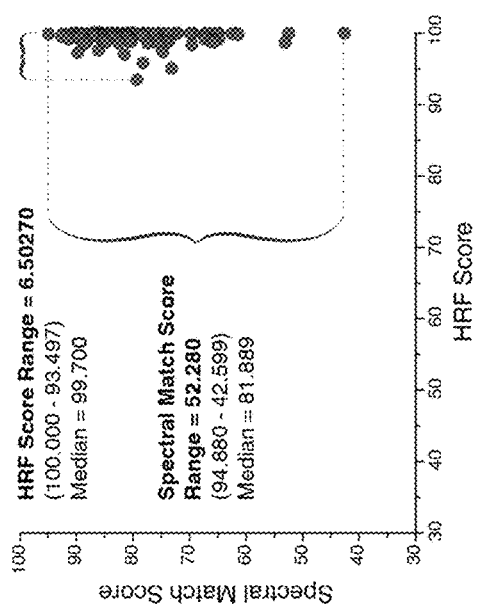

These promising results demonstrate that the methods of this aspect of the invention is highly indicative that a feasible chemical composition has been deduced. However, it prompts the question as to whether similar results could be obtained from random chemical formulas. To test the specificity of the method all spectra in the dataset were subjected to the HRF process using 60,560 unique formulas from the NIST database. Representative results from a spectrum of trimethylsilyl-derivatized beta-sitosterol ($C_{32}H_{58}OSi$) are shown (FIG. 22B). It is noted that the true parent is the smallest formula that can produce a maximal HRF score. The annotated subsets lack the proper combination of atoms to achieve a similarly high score. As expected, all supersets of $C_{32}H_{58}OSi$ produce similarly high scores. This is expected as all subformulas from the true parent will also be included in the subformula sets generated by these superset precursors. We note that in some cases very large formulas which are not true supersets but share a large percentage of atoms with the correct parent can also produce high scores (FIG. 30 (Supplementary Table 2)).

FIG. 30 (Supplementary Table 2) illustrates the Global HRF analysis. Shown here is a summary of the returned HRF results when calculating scores for the 105 dataset spectra against 60,560 unique chemical formulas. Compounds are ranked by ascending monoisotopic mass. The raw number of formulas which produce a HRF score less than, or greater than or equal to the true parent are shown in columns labeled HRF<Parent Score and HRF>=Parent Score. Using the pool of formulas which yielded a HRF Score>=the true parent HRF score the number of true and false supersets were determined. A superset is a formula where all of the atoms in the true parent set are also contained. Non-supersets were those formulas which failed to meet this condition. For those non-supersets the average percentage of atoms shared with the true parent was calculated, along with the average and median number of additional atoms held by the formula in question. We find that these non-supersets which can achieve similarly high HRF scores as the true parent often share a large percentage of atoms with the correct precursor (93.574%) and contain a substantial number of additional atoms on average (19.506).

Figure 22C:
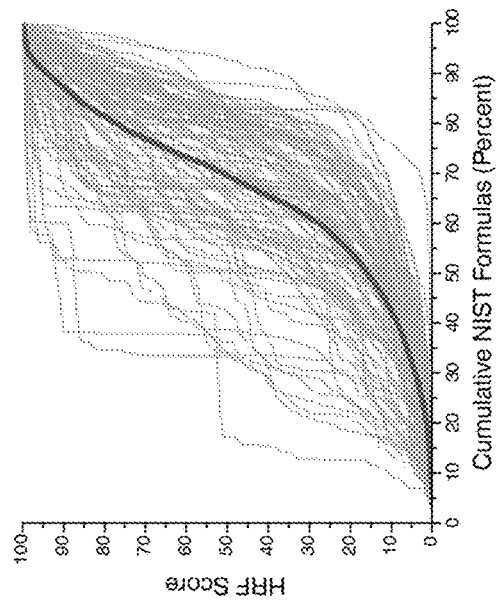
Figure 26:
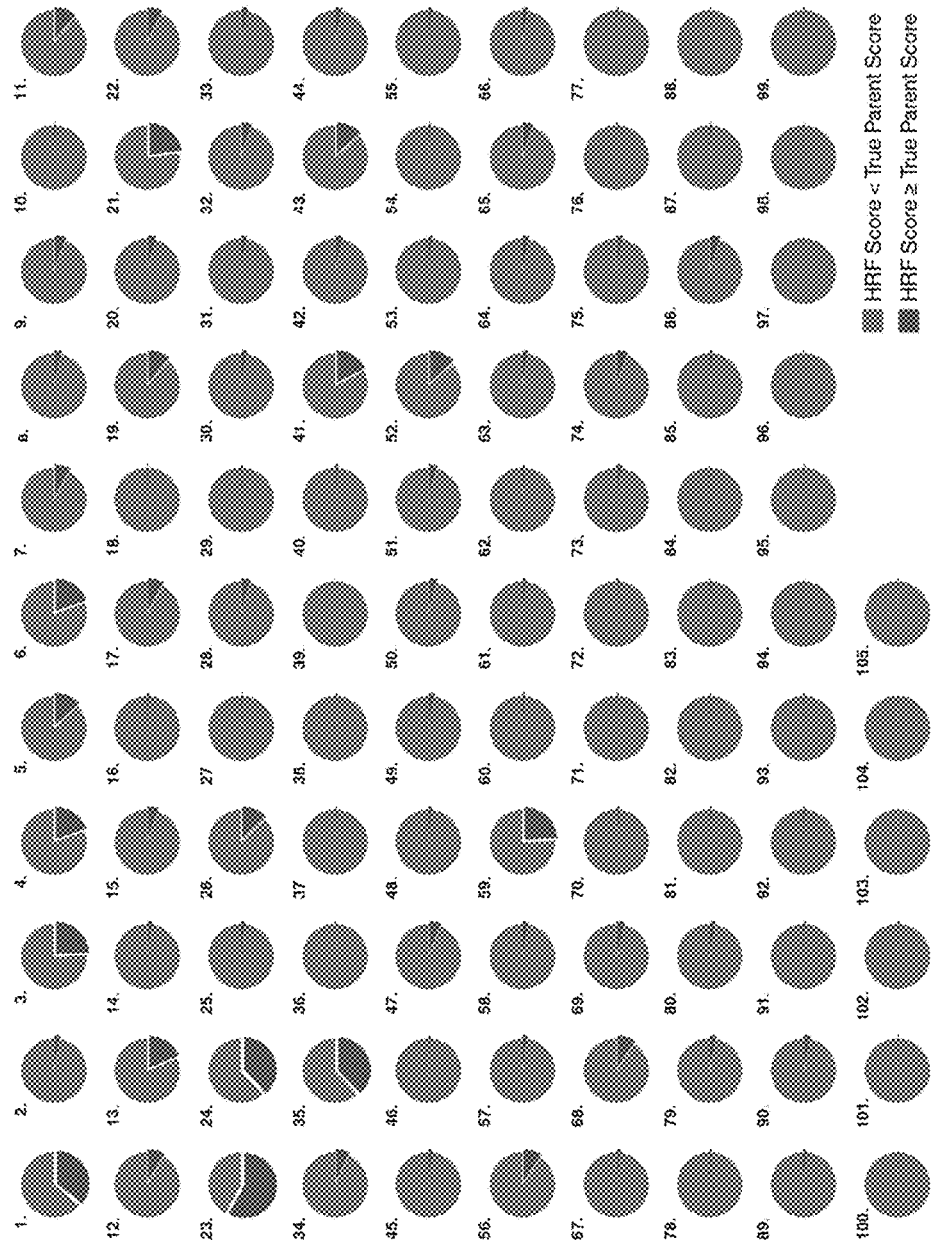
FIG. 26 shows global high-resolution filtering results. For all 105 reference spectra analyzed in this study 60,560 HRF scores were calculated using a unique chemical formula from the NIST 12 EI reference library. Shown here are the results of that analysis for all reference spectra (1-105) ordered by increasing monoisotopic mass. The calculated scores are separated into two categories; formulas yielding HRF scores less than the true parent score (blue), and formulas yielding HRF scores greater than or equal to the true parent score (red). More detailed results are shown in FIG. 30 (Supplementary Table 2). We note that for the majority of considered spectra a very small percentage of formulas can produce a similarly high (or higher score) with few exceptions. Cursory analysis of the cases where a large percentage of formulas can produce high-quality results (1, 23, 24, 35) indicates that such compounds tend to have more simplistic formulas ($C_{10}H_{15}N$, $C_{12}H_{14}N_2O_2$, $C_{15}H_{10}O_2$, $C_{16}H_{17}NO$, respectively). We note that these compounds are comprised exclusively of the four most common organic elements, namely carbon, hydrogen, nitrogen, and oxygen. For compounds with increased chemical complexity the method exhibits increased specificity, as anticipated.

To provide a global view of the method's specificity we show cumulative distributions of HRF scores to all 105 spectra in the dataset along with a representative distribution from the combination of all returned HRF scores (FIGS. 22C and 26). The approximation of this analysis is that all formulas considered have an equal chance of being selected as a putative parent for an acquired spectrum. It is likely that this is not the case and that there will be discrimination in candidate parent selection from spectral matching or a priori information held by the analyst. Nonetheless, based on this representative distribution we would expect that on average ~86.9% of considered formulas will return a HRF score 90 and that only 3.560% of formulas will produce a score greater than or equal to the median calculated HRF score (99.700). For some embodiments, the specificity of the method may be dependent on the complexity of the analyte in question. Increases in elemental complexity and atom count will often result in spectra which a smaller number of precursors can successfully annotate.

Figure 23A:
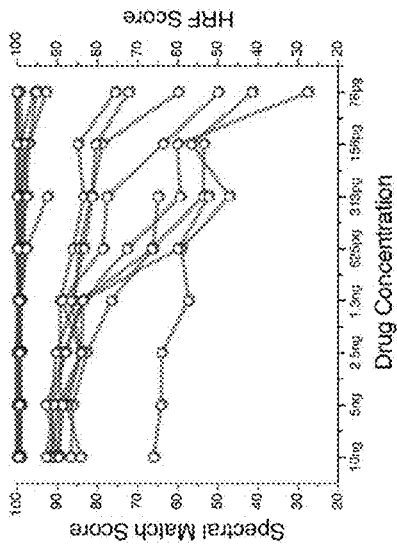
FIGS. 23A-23D show analysis of drugs spiked into human urine at variable concentration.

The present Example also tests performance of the algorithm when applied to spectra collected under suboptimal conditions. As a proof-of-concept, twelve drugs were spiked into human urine at eight concentrations (10 ng/µL to ~78 pg/µL) and extracted prior to GC/MS analysis (FIG. 23A). Of these twelve drugs we report results for nine. Chromatographic resolution was insufficient to successfully separate Benadryl and ketamine, and high background levels of caffeine diminished the ability to analyze the compound through a range of concentrations. As such, further analysis was not carried out.

Figure 23B:
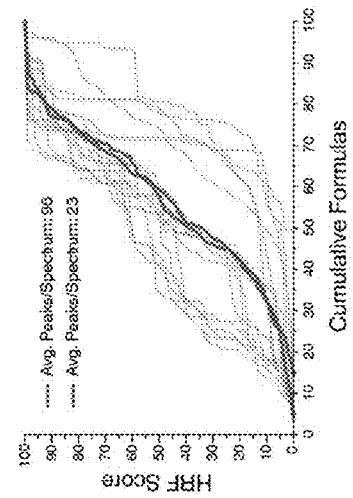
Figure 23C:
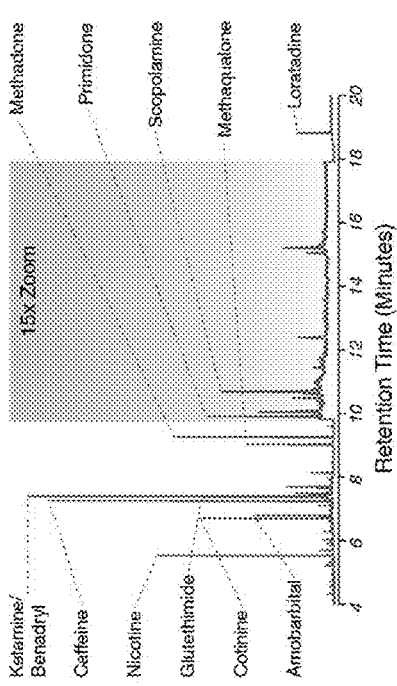

The analysis of compounds in a complex background matrix provides an added challenge to spectral deconvolution (FIG. 23B). Use of conservative criteria in this process diminishes the likelihood that spurious fragments will be included in an extracted spectrum, but may also result in real fragments being excluded. All compounds reported generated a spectrum having 10+ peaks and a spectral match to the true parent within the top 40 returned hits. Associated spectral match and HRF scores are shown (FIGS. 23C, 24A-24I and FIG. 31 (Supplementary Table 3)). We note that spectral match score decreases with diminishing analyte abundance. This is logical as the loss of low abundance peaks at decreased concentrations will contribute negatively to spectral match score. We also note that the associated HRF score remains high (92+) for all observed spectra. This suggests that mass accuracy is highly conserved and that the HRF metric is robust in times of reduced S/N.

FIG. 31 (Supplementary Table 3) provides the associated spectral match score, HRF score, and peak count for all extracted spectra in the drug spike-in dataset. All spectra considered contained at least 10 peaks.

Figure 23D:
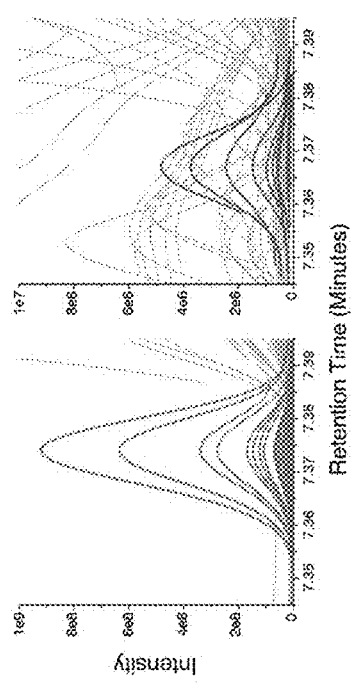
Figures 25A, 25B:
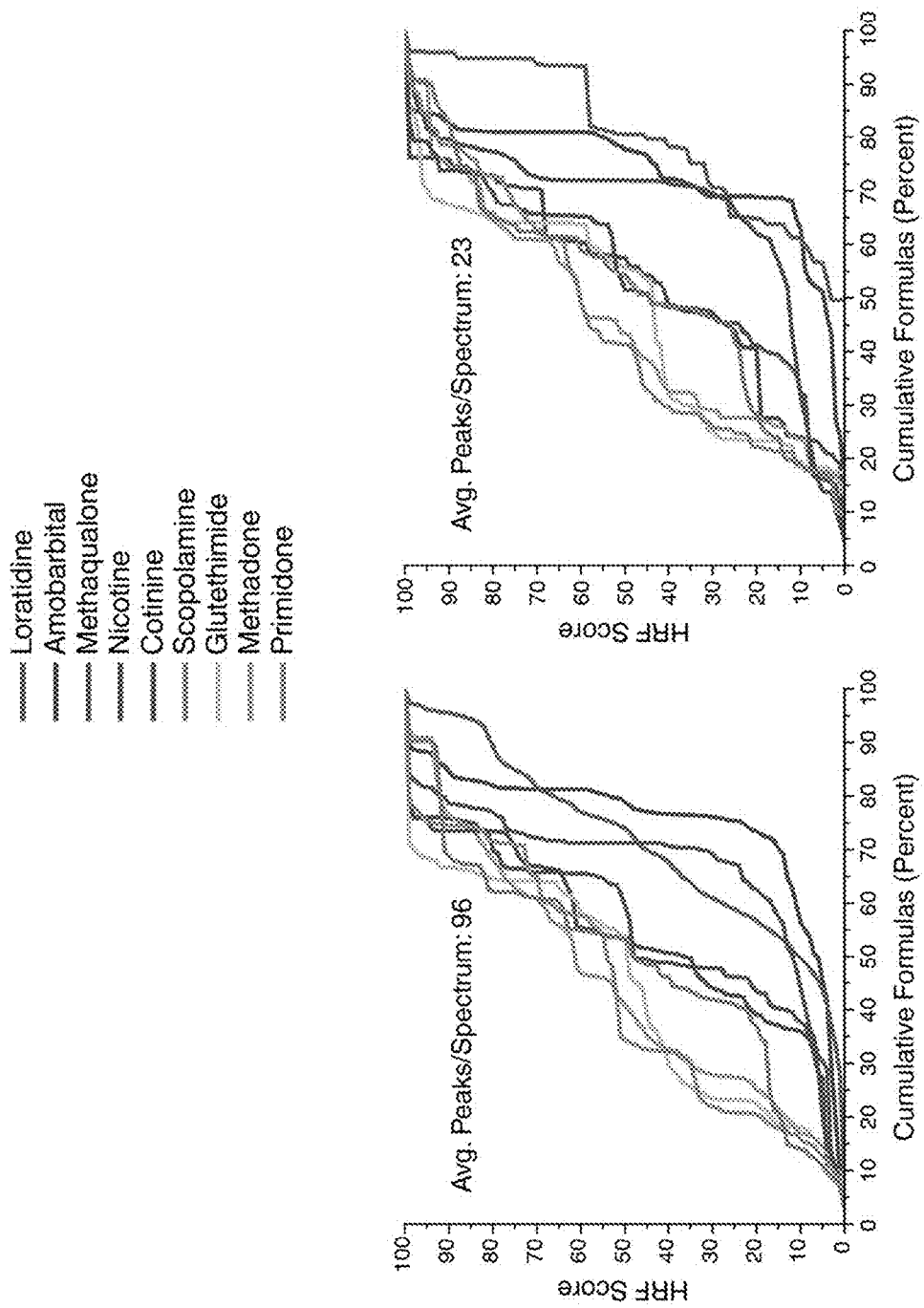
FIGS. 25A-25B show method specificity with regards to peak depleted spectra. Two spectra for each of the drugs analyzed were extracted, one at the highest measured concentration (FIG. 25A) and one at the lowest (FIG. 25B). This data is the same as that in FIG. 23D, but is color-coded here for clarity. An HRF score was calculated using 55,229 unique formulas from the NIST database ranging from 0-500 Da in size. Given that these drugs are relatively small these formulas were assumed to more accurately reflect a pool of potential candidate molecules. Cumulative distributions showing the percentage of formulas that can achieve a certain HRF score are shown. For example, in the case of Amobarbital we find that ~70% of considered formulas return a HRF score ≤10. The specificity of the method does not appear to change whether a "peak-rich" or a "peak-depleted" spectrum is considered as similar cumulative curves are generated for each drug. This data suggests that even spectra collected at diminished concentrations will contain sufficient information for the method to maintain specificity.

The specificity of the method was also evaluated when analyzing spectra containing a reduced number of peaks. To fully interrogate this possibility a HRF score was calculated from 55,290 unique formulas in NIST (0-500 Da) using two spectra for each drug analyzed (one corresponding to the most concentrated data point, the other to the least) (FIGS. 23D and 25A-25B). There is a notable decrease in average peak count (96 v. 23) between the two sets of spectra. However, the cumulative distributions indicate no appreciable differences in the efficacy of the HRF method. It appears that the accurate mass information present in these peak-depleted spectra is sufficient for discrimination between precursors. These data suggest that the proposed method works well even when applied to spectra collected at diminished concentrations.

Here we describe an approach for providing high-res GC-MS users with complementary information further increasing confidence in small molecule identifications. The described approach can be used in conjunction with traditional spectral matching and effectively extends the utility of currently available unit-resolution reference libraries. Moreover, information provided by this approach is completely orthogonal to traditional spectral matching and retention indexing. In fact, it is the only piece of information available to users analyzing novel compounds where a suitable reference spectrum is unavailable. The HRF approach facilitates rapid annotation of spectra, may be extended to LC-MS/MS applications, and may prove useful for automated false-discovery rate calculations which have been largely evasive in small molecule analyses to date.[20]

Methods

Materials and Reagents.

Unless otherwise specified all standard reference materials were purchased from Sigma-Aldrich (St. Louis, Miss.) with the exception of the 37 pesticide reference standards analyzed which were contained in the Organonitrogen Pesticide Mix #1—EPA Method 525.2 and purchased from Restek (Bellefonte, Pa.). Methanol, ethyl acetate, acetone, hexane, dichloromethane, and isopropyl alcohol reagents were also purchased from Sigma-Aldrich. The N-methyl-N-trimethylsilytrifluoroacetamide with 1% trimethylchlorosilane derivatization reagent (MSTFA+1% TMCS) was purchased from Pierce Biotechnology (Rockford, Ill.). Compressed gases (methane, helium, and nitrogen) were ultrahigh purity grade and purchased from Airgas (Madison, Wis.). 200 mg Clean Screen® Extraction Columns were purchased from United Chemical Technologies (Bristol, Pa.).

Sample Preparation and GC/MS Acquisition.

GC/MS analyses were performed on a Trace GC Ultra gas chromatograph (Thermo Fisher Scientific, Milan, Italy) equipped with a GC PAL autosampler (CTC Analytics, Zwingen, Switzerland). Compounds were separated on a 20 m×0.18 mm (i.d.)×0.18 µm ($d_f$) Crossbond 5% diphenyl/95% dimethyl polysiloxane column (Restek Rxi-5Sil MS, Bellefonte, Pa.) with helium carrier gas. The GC was connected to the Q-Exactive instrument (Thermo Fisher Scientific, Bremen, Germany) via a heated transfer line. All MS experiments utilized Automatic Gain Control (AGC)[21-23] and all data was acquired in profile mode.

Urine Drug Testing.

Stock solutions of all drugs analyzed were first prepared at 1 mg/mL in methanol. All drugs reported were combined and diluted (again in methanol) to appropriate concentrations. Stock solutions were kept at 4° C. when not in use. For each gradient data point, 100 µL of the drug mixture was added to raw urine prior to extraction using the 200 mg Clean Screen extraction columns. Acidic and basic drug/metabolite fractions were extracted according to manufacturer protocols.[24] These fractions were subsequently dried down under nitrogen, reconstituted in 50 µL ethyl acetate, and then recombined. For each concentration data point, a 1 µL aliquot was injected (splitless) and separated at 1.2 mL/min He. The following GC gradient was used: 2.5 min isothermal at 60° C., ramp to 210° C. at 40° C./min, ramp to 267° C. at 5° C./min, ramp to 310° C. at 40° C./min, then 6.2 min isothermal at 310° C. The MS transfer line and source temperatures were held at 280° C. and 200° C., respectively. The mass range from 50-500 m/z was analyzed using a resolution of 30,000 (m/Δm), relative to 200 m/z. The AGC target was set to 1e6, and electron ionization (70 eV) was used. Lock mass calibration was employed during acquisition of these data. An unanticipated error occurred in calculation of the necessary mass correction, and many scans acquired during these experiments defaulted to extreme values (~25 ppm). Large distortions in mass accuracy largely inhibit the described HRF approach. As such, during data processing each spectrum was restored to its native-state by removing the applied mass correction as reported in each scan header. Subsequent analyses did not employ this lock-mass correction and mass accuracy was unaffected.

Pesticide Analysis.

The mixture containing 37 EPA 525.2 pesticides was diluted from 500 µg/mL to a working concentration of 3 ng/µL in acetone. A 1 µL aliquot was injected using a 1:10 split at a temperature of 275° C. and separated at 1.2 mL/min He. The following GC oven gradient was used: isothermal at 100° C. for 1 min, 8° C./min to 320° C., and isothermal at 320° C. for 3 min. Transfer line and source temperatures were maintained at 275° C. and 225° C., respectively. In each MS scan, the range from 50-650 m/z was analyzed using a resolution of 17,500 (m/Δm), relative to 200 m/z. Maximum injection times of 100 ms were allowed at an AGC target of 1e6. Electron ionization (EI) at 70 eV was used.

Additional Reference Standard Analysis.

Stock solutions for all other reported standards were prepared individually at a concentration of 1 mg/mL in appropriate solvents. Mixtures containing ~5-10 reference standards were prepared by combining 20 µL aliquots of each standard using no specific organizational scheme. These mixtures were dried down under nitrogen, resuspended in 100 µL of the MSTFA+1% TMCS derivatization reagent, capped, vortexed, and heated at 60° C. for 15 minutes. 100 µL of ethyl acetate was then added to each mixture before being transferred to an autosampler vial. The same GC oven gradient and MS parameters as described in *Urine Drug Testing* were also used here.

Spectral Deconvolution.

Following data collection raw EI-GC/MS spectral data was deconvolved into 'features' and then grouped into individual spectra containing only product ions stemming from a singular parent. This step was critical as the inclusion of extraneous fragment ions in a spectrum can diminish the ability of the algorithm to annotate all observed peaks with exact chemical formulas constrained by the atom set of the parent. Every peak in the raw data file was considered. Peaks observed in at least five consecutive scans having m/z values within +/−10 ppm of one another were grouped together as a data feature. After aggregation of peaks into features, smoothed intensity profiles were created for each. Spurious features arising from noise were eliminated from consideration by requiring that each feature exhibit a "peak-like" shape. All features were required to rise to an apex having at least twice the intensity of the first and last peaks included. Any features arising from fragments common to closely eluting precursors were split into separate features at significant local minima. Features reaching an elution apex at approximately the same time were grouped together. Features were first sorted based on apex intensity. Starting with the most intense fragment a discrete time window around the apex was created. All features having an apex within this window were then grouped together. This width of this window was set to include all peaks having an intensity 96% of the apex peak's intensity. More conservative criteria was used for the extraction of spectra in the urine drug spike-in experiments given the complex background. Here the time window was set to include peaks having an intensity 99% of the apex. Following feature grouping, a new spectrum was created for each group and populated with peaks representing each feature in the group. Peak m/z and intensity values were set equal to the intensity-weighted m/z average of all peaks in the corresponding feature and the intensity at the apex, respectively.

Small Molecule Identification Via Spectral Matching.

Compound identifications for the small molecules analyzed were assigned by comparing deconvolved high-resolution spectra against unit-resolution reference spectra present in the NIST 12 MS/EI Library. All 212,961 unit-resolution reference spectra in the library were extracted to a .JDX file through the NIST MS Search 2.0 program and converted to a format suitable for matching against acquired GC-Orbitrap spectra. A pseudo-unit resolution copy of each high-resolution spectrum was created by combining the intensities of peaks falling within the same nominal mass range. The nominal mass value was reported as peak m/z and all intensity values were normalized relative to the spectrum's base peak (set to 999). To calculate spectral similarity between experimental and reference spectra a weighted dot product calculation was used. First, all peaks in a spectrum were scaled using the following normalization factors reported in the literature[25]:

$$m/z_{normalized} = m/z_{measured} \times 1.3$$

$$intensity_{normalized} = intensity_{measured}^{0.53}$$

The same normalizations were applied to all reference spectra. The following dot product equation was used to measure spectral similarity:

$$100 \times \frac{\sum (m/z[Intensity_{experimental} * Intensity_{reference}]^{0.5})^2}{\sum (Intensity_{experimental} * m/z) \sum (Intensity_{reference} * m/z)}$$

Although simplistic, this approach was more than adequate for retrieving candidate compounds having similar fragmentation patterns to experimentally derived spectra. To increase search space as much as possible all reference spectra were matched against each unit resolution copy of a GC-Orbitrap spectrum acquired during runtime. All compounds reported yielded a confident spectral match with a reference spectrum in the NIST database. Some compounds analyzed did not yield a confident match either as a result of absence of a reference spectrum the database, or the compound in question not returning a correct match in the top 40 hits.

Theoretical Fragment Generation.

A set of theoretical fragments for each candidate compound was produced by generating all non-repeating combinations of atoms from the set contained in the parent chemical formula. The most abundant isotope for each atom was used with the exception of bromine and chlorine. $^{79}$Br and $^{81}$Br have natural isotopic abundances of 0.5069 and 0.4931, respectively. Similarly, $^{35}$Cl and $^{37}$Cl have natural abundances of 0.7576 and 0.2424. For each fragment containing either a bromine or chlorine an additional variant was generated where a heavier isotope was exchanged for its lighter counterpart. This process was repeated in a combinatorial manner for those fragments containing multiple Br and/or Cl atoms. Generation of additional isotopic fragments for those candidates containing atoms in the set $\{^{12}C, ^{32}S, ^{28}Si\}$ was done on a case-by-case basis during the fragment/peak matching process.

Fragment/Peak Matching.

It is assumed that all fragment peaks in an EI-GC/MS spectrum are radical cations. Accordingly, the mass of an electron was subtracted from the monoisotopic mass of each fragment in the set of candidates. Starting with the least massive peak in the GC-Orbitrap spectrum fragments falling within a +/−10 ppm tolerance centered around the peak's measured m/z were found. If no fragments were present within this range, the algorithm moved to the next most massive peak and repeated the process. If a single fragment was found within this range isotopic variants containing substituted $^{13}$C, $^{33}$S, $^{34}$S, $^{29}$Si, or $^{30}$Si atoms were generated where appropriate and added to the list of candidate fragments. If multiple fragments were found within the allowed tolerance each fragment was independently evaluated to determine how many additional peaks/signal could be matched. The fragment resulting in the largest amount of additional matched signal was assumed to be correct and substituted isotopic fragments were added to the list of candidate fragments. All peaks which had matching fragments were stored. After all peaks were considered the total ion current that was matched to a fragment was as calculated by $$\Sigma(mz*intensity)_{annotated} / \Sigma(mz*intensity)_{observed}$$

was returned. This scoring calculation was deemed appropriate as it gives additional weight to larger ions which are inherently more diagnostic of a given precursor than less massive ions. Conceptually, there are fewer molecules in existence which can theoretically produce a fragment at 300 m/z than there are which can produce a fragment at 200 m/z.

REFERENCES

1. Westerhoff, P. & Yoon, Y. Fate of endocrine-disruptor, pharmaceutical, and personal care product chemicals during simulated drinking water treatment processes. *Environ. Sci. Technol.* 39, 6649-6663 (2005).
2. Tareke, E. & Rydberg, P. Analysis of acrylamide, a carcinogen formed in heated foodstuffs. *J. Agric. Food Chem.* 4998-5006 (2002). at <http://pubs.acs.org/doi/abs/10.1021/jf020302f>
3. Kataoka, H., Lord, H. L. & Pawliszyn, J. Applications of solid-phase microextraction in food analysis. *J. Chromatogr. A* 880, 35-62 (2000).
4. Yang, C. et al. Comprehensive mass spectrometric mapping of the hydroxylated amino acid residues of the a1 (V) collagen chain. *J. Biol. Chem.* 287, 40598-610 (2012).
5. Fiehn, O., Kopka, J. & Dormann, P. Metabolite profiling for plant functional genomics. *Nat. Biotechnol.* 1157-1161 (2000).
6. Goodacre, R., Vaidyanathan, S., Dunn, W. B., Harrigan, G. G. & Kell, D. B. Metabolomics by numbers: acquiring and understanding global metabolite data. *Trends Biotechnol.* 22, 245-52 (2004).
7. Allen, J. et al. High-throughput classification of yeast mutants for functional genomics using metabolic footprinting. *Nat. Biotechnol.* 21, 692-6 (2003).
8. Stein, S. An integrated method for spectrum extraction and compound identification from gas chromatography/mass spectrometry data. *J. Am. Soc. Mass Spectrom.* 0305, (1999).
9. Fiehn, O. Extending the breadth of metabolite profiling by gas chromatography coupled to mass spectrometry. *Trends Analyt. Chem.* 27, 261-269 (2008).
10. Fiehn, O., Kopka, J., Trethewey, R. N. & Willmitzer, L. Identification of Uncommon Plant Metabolites Based on Calculation of Elemental Compositions Using Gas Chromatography and Quadrupole Mass Spectrometry. *Anal. Chem.* 72, 3573-3580 (2000).
11. NIST Mass Spectral Library. (2012).
12. Wiley Registry of Mass Spectral Data. (2010).
13. Lewis, S., Kenyon, C. N., Meili, J. & Burlingame, a. L. High resolution gas chromatographic/real-time high resolution mass spectrometric identification of organic acids in human urine. *Anal. Chem.* 51, 1275-1285 (1979).
14. Peterson, A. C., Balloon, A. J., Westphall, M. S. & Coon, J. J. Development of a GC/Quadrupole-Orbitrap mass spectrometer, part II: new approaches for discovery metabolomics. *Anal. Chem.* 86, 10044-51 (2014).
15. Peterson, A. C. et al. Development of a GC/Quadrupole-Orbitrap mass spectrometer, part I: design and characterization. *Anal. Chem.* 86, 10036-43 (2014).
16. Peterson, A. C., McAlister, G. C., Quarmby, S. T., Griep-Raming, J. & Coon, J. J. Development and characterization of a GC-enabled QLT-Orbitrap for high-resolution and high-mass accuracy GC/MS. *Anal. Chem.* 82, 8618-28 (2010).
17. Wolf, S., Schmidt, S., Müller-Hannemann, M. & Neumann, S. In silico fragmentation for computer assisted identification of metabolite mass spectra. *BMC Bioinformatics* 11, 148 (2010).
18. Hill, D. W., Kertesz, T. M., Fontaine, D., Friedman, R. & Grant, D. F. Mass spectral metabonomics beyond elemental formula: chemical database querying by matching experimental with computational fragmentation spectra. *Anal. Chem.* 80, 5574-82 (2008).
19. Kerber, A., Laue, R., Meringer, M. & Varmuza, K. MOLGEN-MS: Evaluation of low resolution electron impact mass spectra with MS classification and exhaustive structure generation. *Adv. Mass Spectrom* 15, 939-940 (2001).
20. Matsuda, F. et al. Assessment of metabolome annotation quality: a method for evaluating the false discovery rate of elemental composition searches. *PLoS One* 4, e7490 (2009).
21. Michalski, A. et al. Mass spectrometry-based proteomics using Q Exactive, a high-performance benchtop quadrupole Orbitrap mass spectrometer. *Mol. Cell. Proteomics* 10, M111.011015 (2011).
22. Olsen, J. V et al. A dual pressure linear ion trap Orbitrap instrument with very high sequencing speed. *Mol. Cell. Proteomics* 8, 2759-69 (2009).
23. Second, T. P. et al. Dual-pressure linear ion trap mass spectrometer improving the analysis of complex protein mixtures. *Anal. Chem.* 81, 7757-65 (2009).
24. Solid Phase Extraction Applications Manual. 42-44 (2008). at
25. Kim, S., Koo, I., Wei, X. & Zhang, X. A method of finding optimal weight factors for compound identification in gas chromatography-mass spectrometry. *Bioinformatics* 28, 1158-63 (2012).

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method of analyzing an analyte in a sample using mass spectrometry, said method comprising:
    (a) providing said sample;
    (b) generating fragment ions from said sample;
    (c) measuring a fragmentation spectrum for said analyte using a mass spectrometry technique; wherein said fragmentation spectrum comprises a plurality of peaks corresponding to measured mass-to-charge ratios of said fragment ions from said sample; wherein said fragmentation spectrum is characterized by a signal parameter corresponding to said peaks of said fragmentation spectrum;
    (d) providing a candidate molecule having a molecular formula for analysis of said fragmentation spectrum of said analyte, wherein said candidate molecule has a molecular formula;
    (e) and determining putative fragment masses for non-repeating combinations of atoms from the molecular formula of the candidate molecule; and
    (f) comparing the putative fragment masses of said candidate molecule to the measured mass-to-charge ratios from said fragmentation spectrum to determine a signal parameter similarity of the fragmentation spectrum that matches the putative fragment masses of said candidate molecule, thereby analyzing said analyte using mass spectrometry,
    wherein the signal parameter is total ion current (TIC) corresponding to the sum of said peaks of said fragmentation spectrum, and the signal parameter similarity is the percentage of the TIC corresponding to peaks of the fragmentation spectrum that match the putative fragment masses of said candidate molecule.

2. The method of claim 1, wherein putative fragment masses are determined for all possible fragment ions or all non-repeating combinations of atoms of the molecular formula from said candidate molecule and compared to said measured mass-to-charge ratios.

3. The method of claim 1, wherein said percentage of the TIC that matches the putative fragment masses corresponds to peaks of said fragmentation spectrum that match a putative fragment mass to within 30 ppm.

4. The method of claim 1, wherein said candidate molecule is determined via matching said fragmentation spectrum with one or more reference spectra in a reference spectra database, or wherein said candidate molecule corresponds to a target compound for analysis in said sample, or wherein said candidate molecule corresponds to one or more candidate chemical formulas.

5. The method of claim 1, further comprising calculating a spectral overlap between the fragmentation spectrum of said analyte and a reference spectrum of said candidate molecule.

6. The method of claim 5, wherein calculating the spectral overlap comprises using a dot product calculation.

7. The method of claim 5, wherein calculating the spectral overlap comprises rounding all peak m/z values of said fragmentation spectrum to the nearest integer value.

8. The method of claim 5, wherein calculating said spectral overlap between the fragmentation spectrum of said analyte and said reference spectra of said candidate molecule generates a spectral overlap score.

9. The method of claim 8, wherein the spectral overlap score and percentage of TIC of the fragmentation spectrum that matches the putative fragment masses are combined to generate a high-resolution filtered score for said candidate molecule.

10. The method of claim 1 further comprising the step of providing a plurality of different candidate molecules for analysis of said fragmentation spectrum of said analyte, wherein putative fragment masses are independently determined for each of said candidate molecules and independently compared to said measured mass-to-charge ratios from said fragmentation spectrum, thereby determining signal parameter similarity of the fragmentation spectrum that matches the putative fragment masses for each of said candidate molecules.

11. The method of claim 10, wherein said plurality of different candidate molecules are determined by making a comparison of said peaks of said fragmentation spectrum to a plurality of reference spectra of a reference spectra database.

12. The method of claim 10, wherein each of said plurality of different candidate molecules are characterized by a spectral overlap score greater than or equal to a threshold value.

13. The method of claim 10 further comprising, for each of said candidate molecules, independently determining the signal parameter similarity of the fragmentation spectrum that matches the putative fragment masses of the candidate molecule.

14. The method of claim 13, wherein the signal parameter similarity of the fragmentation spectrum that matches the putative fragment masses for each given candidate molecule are used to identify which of the candidate molecules have a composition corresponding to the analyte.

15. The method of claim 14, further comprising, for each of said candidate molecules, independently calculating a spectral overlap between the fragmentation spectrum of said analyte and a reference spectra for said candidate molecule, thereby generating a spectral overlap score for each of said candidate molecules.

16. The method of claim 15, wherein, for each of said candidate molecules, the spectral overlap score and the percentage of the TIC of the fragmentation spectrum that matches the putative fragment masses are combined, thereby generating a high-resolution filtered score for each of said candidate molecules.

17. The method of claim 16, further comprising identifying the candidate molecule having the largest high-resolution filtered score as having the same composition of said analyte.

18. The method of claim 1, further comprising purifying said sample having said analyte prior to measuring said fragmentation spectrum.

19. The method of claim 1 further comprising generating said fragment ions using one or more ionization or dissociation methods.

20. The method of claim 19, wherein said one or more ionization or dissociation methods are selected from the group consisting of electron ionization (EI), chemical ionization (CI), electrospray ionization (ESI), atmospheric pressure chemical ionization (APCI), and matrix-assisted laser desorption ionization (MALDI).

21. The method of claim 19, wherein said one or more ionization or dissociation methods are selected from the group consisting of collision induced dissociation (CID), surface induced dissociation (SID), laser induced dissociation (LID), neutral reaction dissociation, ion reaction dissociation, electron capture dissociation (ECD), and electron transfer dissociation (ETD).

22. The method of claim 1 wherein said fragmentation spectrum is generated using a GC-MS method with electron ionization (EI) or a LC-MS method with electron ionization (EI).

23. The method of claim 1, wherein said fragmentation spectrum is generated using a multistage mass spectrometry method.

24. The method of claim 1 further comprising the step of measuring an intact mass value for a precursor ion derived from said analyte, and evaluating whether said candidate molecule has a molecular mass within a preselected range of said intact mass value.

25. The method of claim 1, wherein step (a) comprises a deconvolution step comprising:
1) performing two or more EI fragmentation scans of said analyte;
2) grouping together fragment peaks which have similar m/z values observed in consecutive EI fragmentation scans, thereby generating a data feature, wherein peaks which do not have similar m/z value observed in consecutive scans are grouped in separate data features; and
3) grouping together data features having peaks which elute within the same time period, thereby generating a set of fragment peaks originating from the analyte.

26. A method of identifying the composition of an analyte in a sample using mass spectrometry, said method comprising:
(a) providing said sample;
(b) generating fragment ions from said sample;
(c) measuring a fragmentation spectrum for said analyte using a mass spectrometry technique; wherein said fragmentation spectrum comprises a plurality of peaks corresponding to measured mass-to-charge ratios of said fragment ions from said sample;
(d) providing a plurality of different candidate molecules for analysis of said fragmentation spectrum of said analyte, wherein each candidate molecule has a molecular formula;
(e) independently determining an atomic composition from the molecular formulas for each of said candidate molecules and determining putative fragment masses for every combination of atoms containing one or more atoms from said atomic composition for each of said candidate molecules;
(f) comparing the measured mass-to-charge ratio of each peak from said fragmentation spectrum to the putative fragment masses for each of said candidate molecules, and determining if the measured mass-to-charge ratio of each peak matches at least one putative fragment mass for each of said candidate molecules; and
(g) determining which candidate molecule is able to produce putative fragment masses that match the mass-to-charge ratios of a greater number of peaks from said fragmentation spectrum, thereby identifying the composition of said analyte.

27. The method of claim 26, further comprising, for each of said candidate molecules, independently calculating a spectral overlap between the fragmentation spectrum of said analyte and a reference spectra for said candidate molecule, thereby generating a spectral overlap score for each of said candidate molecules.

28. The method of claim 27, wherein, for each of said candidate molecules, the spectral overlap score and percentage of total ion current (TIC) of the fragmentation spectrum corresponding to peaks that match the putative fragment masses are combined, thereby generating a high-resolution filtered score for each of said candidate molecules.

29. The method of claim 28, further comprising identifying the candidate molecule having the largest high-resolution filtered score as having the composition of said analyte.

30. The method of claim 26, wherein said plurality of different candidate molecules are determined by making a comparison of said peaks of said fragmentation spectrum to a plurality of reference spectra of a reference spectra database.

* * * * *